(12) United States Patent
Hazari et al.

(10) Patent No.: US 12,071,445 B2
(45) Date of Patent: Aug. 27, 2024

(54) PRECATALYST SCAFFOLDS FOR CROSS-COUPLING REACTIONS, AND METHODS OF MAKING AND USING SAME

(71) Applicant: YALE UNIVERSITY, New Haven, CT (US)

(72) Inventors: Nilay Hazari, New Haven, CT (US); Patrick Melvin, New Haven, CT (US); Damian Hruszkewycz, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 18/175,357

(22) Filed: Feb. 27, 2023

(65) Prior Publication Data

US 2023/0203077 A1    Jun. 29, 2023

Related U.S. Application Data

(62) Division of application No. 17/094,384, filed on Nov. 10, 2020, now Pat. No. 11,603,381, which is a division of application No. 15/516,827, filed as application No. PCT/US2015/054368 on Oct. 7, 2015, now Pat. No. 10,894,802.

(51) Int. Cl.
   *C07F 17/02* (2006.01)
(52) U.S. Cl.
   CPC .......... *C07F 17/02* (2013.01); *C07C 2602/10* (2017.05)
(58) Field of Classification Search
   None
   See application file for complete search history.

(56) References Cited

U.S. PATENT DOCUMENTS

2009/0093657 A1    4/2009   Buchanan et al.
2009/0264608 A1   10/2009   Wakatsuki et al.

FOREIGN PATENT DOCUMENTS

WO        2006064814 A1    6/2006

OTHER PUBLICATIONS

Chen et al. Can. J. Chem., 2009, 87, 280-287 (Year: 2009).*
Extended European Search Report for European Patent Application No. 15848587.0 issued Apr. 23, 2018.
PCT International Search Report and Written Opinion issued for PCT International Application No. PCT/US2015/054368 issued Feb. 16, 2016.
Chemical Abstract Service, RN: 1605321-50-3 CA network version-STN database, May 2014.
Alias , et al., "Synthesis and reactivity studies of Pd(II) complexes of the bulky CH(SiMe3)2 group. X ray structure of the indenyl derivative (η-Ind)Pd[CH(SiMe3)2](PMe3)", Journal of Organometallic Chemistry 577(2):, Apr. 1999 , 316-322.

(Continued)

*Primary Examiner* — Yun Qian
(74) *Attorney, Agent, or Firm* — Saul Ewing LLP; Kathryn Doyle; Domingos J. Silva

(57) ABSTRACT

The present invention provides novel transition-metal precatalysts that are useful in preparing active coupling catalysts. In certain embodiments, the precatalysts of the invention are air-stable and moisture-stable. The present invention further provides methods of making and using the precatalysts of the invention.

7 Claims, 10 Drawing Sheets

Mingos/Hartwig

Buchwald

Organ

Nolan

(56) References Cited

OTHER PUBLICATIONS

Bielinski, et al., "Synthesis, Properties, and Reactivity of Palladium and Nickel NHC Complexes Supported by Combinations of Allyl, Cyclopentadienyl, and Indenyl Ligands", Organometallics 32 (15), 2013, 4025-4037.
Bruno, et al., "Buchwald Ligands and Precatalysts", Strem Chemicals, Inc., 2015, 1-61.
Castonguay, et al., "Chloro[n5-1-(dimethylaminoethyl_indenyl]-(triphenylphosphine)nickel(II) diethyl ether hemisolvate", Acta Crystallographica, Section E: Structure Reports Online, vol. 61 (8), 2005, m1512-m1513.
Chen, et al., "Phenylsilane dehydrocoupling and addition to styrene catalyzed b (R-indenyl)ni(phosphine)(methyl) complexes", Canadian Journal of Chemistry, 2009, 87, 2009, 280-287.
Fiato, et al., "Intramolecular Cyclization of $\pi$-1-Chloro-3-phenylallylpalladium(II) Complexes. A Novel Route to Stable Indenyl Complexes of Palladium(II)", J.C.S. Chem. Comm, 1975, 869-871.
Fontaine, et al., "Hydrosilylation of alkenes and ketones catalyzed by nickel(II) idenyl complexes", Canadian Journal of Chemistry, 81, 2003, 1299-1306.
Fontaine, et al., "Me2AICH2PMe2: a new, bifunctional cocatalyst for the Ni(II)-catalyzed oligomerization of PhSiH3", J. Am. Chem. Soc. 126(28), 2004, 8786-8794.
Fontaine, et al., "Solid State Structures and Phosphine Exchange Reactions of (1-Me-Indenyl)(PR3)Ni—Cl", Organometallics 20(24), 2001, 5156-5161 (Abstract Only).
Gareau, et al., "Idenyl-Nickel Complexes Bearing a Pendant, Hemilabile Olefin Ligand: Preparation, Characterization, and Catalytic Activities", Organometallics 24(16), 2005, 4003-4013.
Hintermann, et al., "Interactions of Cationic Palladium(II)- and Platinum(II)-$\eta$-Allyl Complexes with Fluoride: Is Asymmetric Allylic Fluorination a Viable Reaction?", European Journal of Inorganic Chemistry 2006(7), Apr. 2006, 1397-1412 (Abstract Only).
Jimenez Tenorio, et al., "Structural characterisation of cationic methylallyl, methylindenyl and pentamethylcyclopentadienyl nickel complexes containing the bulky phosphine 1,2-bis(diisopropylphosphino)ethane", J Chem Soc., Dalton Trans., 2001, 653-657.
Jimenez-Tenorio, et al., "Cationic Nickel Complexes Containing Bulky Phosphine Ligands: Catalyst Precursors for Styrene Polymerization", Organometallics 23(13), 2004, 3139-3146.
Karlsson, et al., "Mechanism of the palladium-catalyzed carbohydroxylation of allene-substituted conjugated dienes: rationalization of the recently observed nucleophilic attack by water on a (pi-allyl)palladium intermediate", Chemistry 14(30), 2008, 9175-9180.
Kinzel, et al., "A new palladium precatalyst allows for the fast Suzuki-Miyaura coupling reactions of unstable polyfluorophenyl and 2-heteroaryl boronic acids", J. Am. Chem. Soc. 132(40), 2010, 14073-14075.
Marion, et al., "Modified (NHC)Pd(allyl)Cl (NHC=N-Heterocyclic Carbene) Complexes for Room-Temperature Suzuki-Miyaura and Buchwald-Hartwig Reactions", J. Am. Chem. Soc. 128(12), 2006, 4101-4111.
Nakasuji, et al., "Coordination of polycyclic conjugated hydrocarbons to palladium. Syntheses, characterization, and molecular orbital study of Pd(.eta.3-phenalenyl)(acac) and [Pd(.eta.3-indenyl)Cl]2", Organometallics 3(8), 1984, 1257-1260.
Ritleng, et al., "Half-sandwich NHC-nickel(II) complexes as precatalysts for the fast Suzuki coupling of aryl halides: a comparative study", Dalton Transactions, 2010, 39, 2010, 8153-8160.
Sui-Seng, et al., "Catalytic reactivities of indenyl-nickel, indenyl-palladium, and PCsp3P-nickel complexes", Topics In Catalysis 37(2-4), Apr. 2006, 81-90.
Sui-Seng, et al., "New palladium(II)-(eta(3/5)- or eta1-indenyl) and dipalladium(I)-(mu,eta3-indenyl) complexes", J Am Chem Soc. 128(19), 2006, 6508-6519.
Sui-Seng, et al., "New Routes to eta1-and (eta3-eta5)-Idenylpalladium Complexes: Synthesis, Characterization, and Reactivities", Organometallics 23(6), 2004, 1236-1246.
Sui-Seng, et al., "Synthesis and Reactivities of Neutral and Cationic Idenyl-Palladium Complexes", Organometallics 25(3), 2006, 571-579.
Sun, et al., "Idenylnickel(II) Halides for the Polymerization of Styrene in the Presence of NaBPh4/PPh3", Chinese Journal of Chemistry 24, 2006, 409-413.
Viciu, et al., "Well-Defined, Air-Stable (NHC)Pd(Allyl)Cl (NHC=N-Heterocyclic Carbene) Catalysts for the Arylation of Ketones", Org. Lett. 4 (23), 2002, 4053-4056.
Vollmerhaus, et al., "Preparation and Characterization of Cationic Nickel Idenyl Complexes [(1-methylindenyl) MiLL]+", Organometallics 16(22), 1997, 4762-4764.
Wang, et al., "Preparation, Characterization, and reactivities of thienyl nickel complexes bearing idenyl ligands", Journal of Organometallic Chemistry 660, 2002, 98-107.
Xie, et al., "Synthesis and Structure of indenylnickel(II) chlorides bearing free N-heterocyclic carbine ligands and their catalysis for styrene polymerization", Polyhedron 28(13), 2009, 2585-2590.

\* cited by examiner

Fig. 1
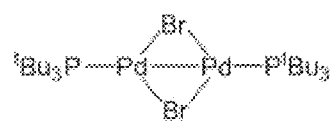
Mingos/Hartwig
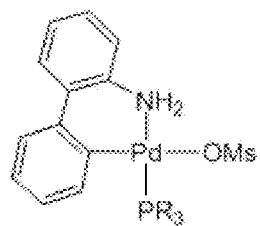
Buchwald
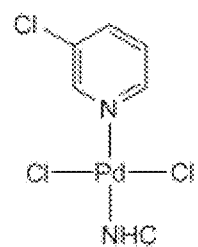
Organ
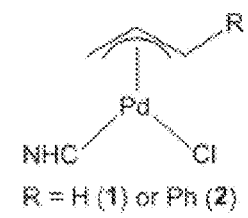
Nolan

Fig. 2

*i) Buchwald-Hartwig Reaction*

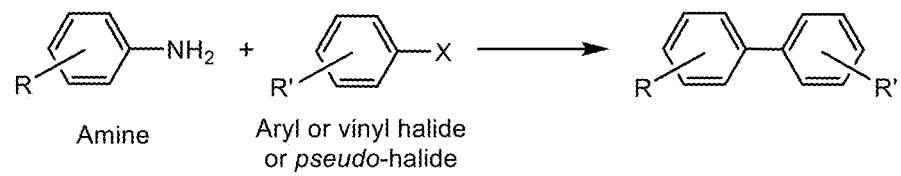

Amine | Aryl or vinyl halide or *pseudo*-halide

*ii) Negishi Reaction*

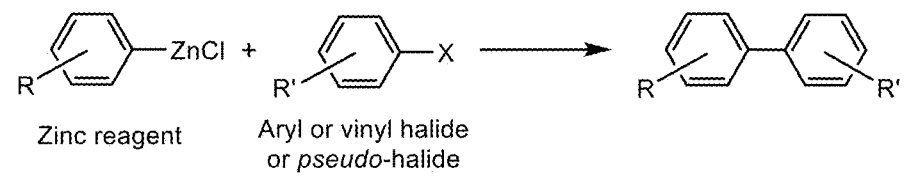

Zinc reagent | Aryl or vinyl halide or *pseudo*-halide

*iii) Kumada Reaction*

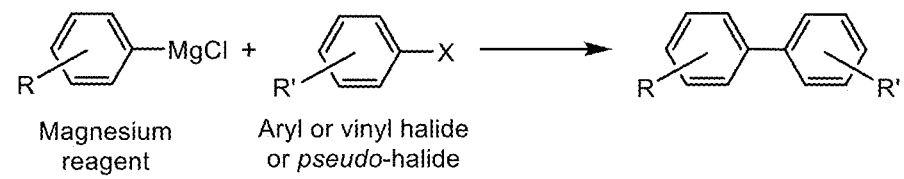

Magnesium reagent | Aryl or vinyl halide or *pseudo*-halide

*iv) Stille Reaction*

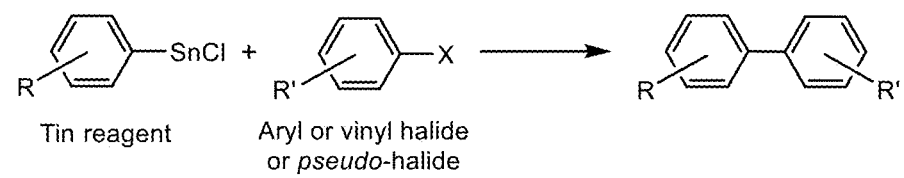

Tin reagent | Aryl or vinyl halide or *pseudo*-halide

*v) α-Arylation*

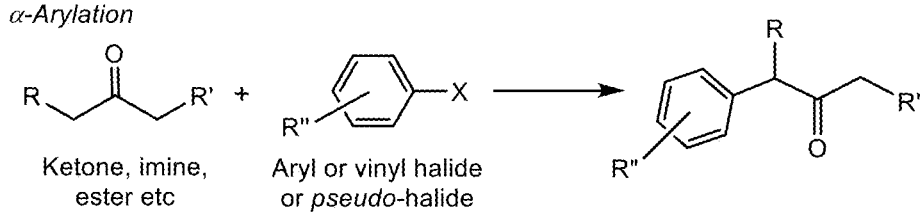

Ketone, imine, ester etc | Aryl or vinyl halide or *pseudo*-halide

*vi) C-S or C-O Bond Formation*

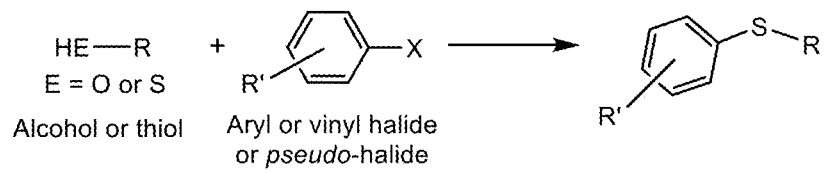

Alcohol or thiol | Aryl or vinyl halide or *pseudo*-halide

E = O or S

*vii) Anaerobic alcohol oxidation*

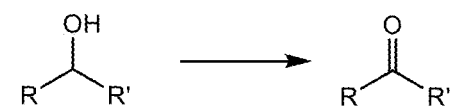

*viii) Suzuki-Miyaura Reaction*

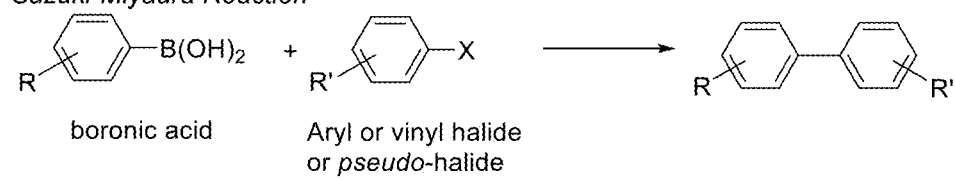

boronic acid | Aryl or vinyl halide or *pseudo*-halide

PRECATALYST SCAFFOLDS FOR CROSS-COUPLING REACTIONS, AND METHODS OF MAKING AND USING SAME

CROSS-REFERENCE TO RELATED APPLICATIONS

The present application is a divisional of, and claims priority to, U.S. application Ser. No. 17/094,384, filed Nov. 10, 2020, now allowed, which is a divisional of, and claims priority to, U.S. application Ser. No. 15/516,827, filed Apr. 4, 2017, now U.S. Pat. No. 10,894,802, issued Jan. 19, 2021, which is a 35 U.S.C. § 371 national phase application from, and claims priority to, International Application No. PCT/US2015/054368, filed Oct. 7, 2015, and published under PCT Article 21(2) in English, which claims priority under 35 U.S.C. § 119(e) to U.S. Provisional Application No. 62/061,319, filed Oct. 8, 2014, all of which applications are incorporated herein by reference in their entireties.

STATEMENT REGARDING FEDERALLY SPONSORED RESEARCH OR DEVELOPMENT

This invention was made with government support under 1122492 awarded by National Science Foundation. The government has certain rights in the invention.

BACKGROUND OF THE INVENTION

Transition metal-catalyzed cross-coupling has found applications in diverse areas of chemistry, such as total synthesis, materials and bioorganic chemistry. In fact, cross-coupling is one of the most powerful and general synthetic methods. In particular, the active pharmaceutical ingredients of drugs such as losartan ((2-butyl-4-chloro-1-{[2'-(1H-tetrazol-5-yl)biphenyl-4-yl]methyl}-1H-imidazol-5-yl) methanol), used to treat high blood pressure, and atazanavir (methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl] carbamoyl}-2,2-dimethylpropyl]carbamate), used to treat HIV, are synthesized using cross-coupling.

The most effective cross-coupling catalysts utilize Pd and feature sterically demanding, electron-rich phosphine or N-heterocyclic carbene (NHC) ancillary ligands. The active species in catalysis, commonly monoligated Pd(0), is often generated through the addition of excess ligand to a Pd(0) source. However, the specialized ligands utilized in most cross-coupling reactions are often as expensive as the Pd(0) source, and the use of excess ligand is not economically feasible. Instead, a variety of well-defined Pd(I) and Pd(II) precatalysts, which feature a 1:1 Pd:ligand ratio, have been developed.

There is still a need in the art for novel precatalysts, which can be efficiently converted to an active catalytic species. The present invention addresses and meets this need.

BRIEF SUMMARY OF THE INVENTION

The invention provides a precatalyst of formula (I), or a salt or solvate thereof:

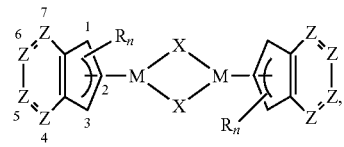

(I)

wherein in (I) each occurrence of M is independently a transition metal; each occurrence of X is independently a ligand; each occurrence of R is independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, with the proviso that each of the 5-membered rings is substituted with at least one independently selected R; Z is CH, CR or N, with the proviso that 0-2 Z groups are N; or the Z groups at the 5- and 6-positions are null and the Z groups at the 4- and 7-positions are independently R; and, n is 1, 2, 3, or 4.

The invention further provides a precatalyst of formula (II), or a salt or solvate thereof:

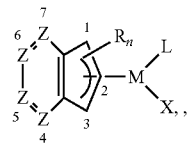

(II)

(II), wherein in (II) M is a transition metal; X is a ligand; each occurrence of R is independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, with the proviso that the 5-membered ring is substituted with at least one R; Z is CH, CR or N, with the proviso that 0-2 Z groups are N; or the Z groups at the 5- and 6-positions are null and the Z groups at the 4- and 7-positions are independently R; L is a monodentate or bidentate ligand; and n is 1, 2, 3, or 4.

The invention further provides a method of preparing the precatalyst of formula (I). In certain embodiments, the method comprises contacting a mixed alkaline/transition metal or alkaline-earth/transition metal salt with the following ligand

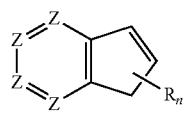

in the presence of a base in an organic solvent to form a reaction mixture.

The invention further provides a method of preparing a precatalyst of formula (II). In certain embodiments, the method comprises contacting a catalyst of formula (I) with a ligand contemplated within the invention.

The invention further provides a method of promoting a reaction between a first reagent and a second reagent. In certain embodiments, the method comprises contacting the first reagent and the second reagent in the presence of at least one selected from the group consisting of (a) a precatalyst of formula (I) and a ligand; and (b) a precatalyst of formula (II).

The invention further provides a method of promoting anaerobic oxidation of a primary or secondary alcohol. In certain embodiments, the method comprises contacting the primary or secondary alcohol with at least one selected from the group consisting of (a) the precatalyst of formula (I) and a ligand; and (b) the precatalyst of formula (II).

In certain embodiments, each occurrence of M in (I) is independently selected from the group consisting of Pd, Ni and Pt. In other embodiments, M in (II) is selected from the group consisting of Pd, Ni and Pt. In yet other embodiments, the two occurrences of M in (I) are identical. In yet other embodiments, the two occurrences of M in (I) are Pd. In yet other embodiments, M in (II) is Pd.

In certain embodiments, the two occurrences of X in (I) are identical. In other embodiments, each of the two occurrences of X in (I) is independently a weakly coordinating ligand. In yet other embodiments, each of the two occurrences of X in (I) is independently selected from the group consisting of halide, trifluoromethanesulfonate (triflate), tosylate, mesylate, tetrafluoroborate, tetraphenylborate, hexafluorophosphine, acetate, trifluoroacetate, acetonitrile, tetrahydrofuran, dichloromethane and water. In yet other embodiments, each of the two occurrences of X in (I) is an anion. In yet other embodiments, X in (II) is selected from the group consisting of halide, trifluoromethanesulfonate (triflate), tosylate, mesylate, tetrafluoroborate, tetraphenylborate, hexafluorophosphine, acetate, trifluoroacetate, acetonitrile, tetrahydrofuran, dichloromethane and water. In yet other embodiments, X in (II) is an anion.

In certain embodiments, the two ligands comprising 5-membered rings are identical. In other embodiments, each of the 5-membered rings is substituted with at least one R selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl. In yet other embodiments, each of the 5-membered rings is substituted with at least one R selected from the group consisting of methyl, isopropyl and tert-butyl. In yet other embodiments, the 1- or 3-position of each of the 5-membered rings is substituted with R. In yet other embodiments, the 2-position of each of the 5-membered rings is substituted with R. In yet other embodiments, each occurrence of Z is independently selected from the group consisting of CH and CR.

In certain embodiments, the 5-membered ring is substituted with at least one R selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl. In yet other embodiments, the 5-membered ring is substituted with at least one R selected from the group consisting of methyl, isopropyl and tert-butyl. In yet other embodiments, the 1- or 3-position of the 5-membered rings is substituted with R. In yet other embodiments, the 2-position of the 5-membered rings is substituted with R. In yet other embodiments, each occurrence of Z is independently selected from the group consisting of CH and CR.

In certain embodiments, L is a bidentate ligand, and X is present and coordinates to M. In other embodiments, L is a bidentate ligand, and X is absent or does not coordinate to M. In yet other embodiments, X is a weakly coordinating ligand. In yet other embodiments, L is selected from the group consisting of 1,3-bis(2,6-diisopropyl phenyl)-1,3-dihydro-2H-imidazol-2-ylidene and 1,3-bis(2,6-bis-(diphenylmethyl)-4-methoxyphenyl) imidazol-2-ylidene.

In certain embodiments, L is a monodentate phosphine ligand. In other embodiments, L is a bidentate phosphine ligand.

In certain embodiments, L is at least one selected from the group consisting of AmPhos (di-t-butylphosphino-4-dimethylaminobenzene), DavePhos (2-dicyclohexyl phosphino-2'-(N,N-dimethylamino)biphenyl), $^{tBu}$DavePhos (2-Di-tert-butylphosphino-2'-(N,N-dimethylamino)biphenyl), QPhos (1,2,3,4,5-pentaphenyl-1'-(di-tert-butylphosphino) ferrocene), RuPhos (2-dicyclohexylphosphino-2',6'-diisopropoxybiphenyl), SPhos (2-dicyclohexylphosphino-2',6'-dimethoxybiphenyl), XPhos (2-dicyclohexylphosphino-2',4',6'-triisopropylbiphenyl), $^{tBu}$XPhos (2-Di-tert-butylphosphino-2',4',6'-triisopropylbiphenyl), $^{Me4tBu}$XPhos (2-Di-tert-butylphosphino-3,4,5,6-tetramethyl-2',4',6'-triisopropyl-1,1'-biphenyl), BrettPhos (2-(Dicyclohexylphosphino)3,6-dimethoxy-2',4',6'-triisopropyl-1,1'-biphenyl), $^{tBu}$BrettPhos (2-(Di-tert-butylphosphino)-2',4',6'-triisopropyl-3,6-dimethoxy-1,1'-biphenyl), $^{Ad}$BrettPhos (2-(Diadamantylphosphino)-2',4',6'-triisopropyl-3,6-dimethoxy-1,1'-biphenyl), Me-DalPhos (2-(Di-1-adamantylphosphino) phenylpiperidine), Mor-DalPhos (Di(1-adamantyl)-2-morpholinophenylphosphine), Di(1-adamantyl)-1-piperidinylphenylphosphine, triphenylphosphine, tri(o-tolyl) phosphine, tricyclohexylphosphine and tri(t-butyl)phosphine.

In certain embodiments, L is selected from the group consisting of 1,1'-bis(diphenylphosphino)ferrocene (DPPF), 4,5-bis(diphenylphosphino)-9,9-dimethylxanthene (XantPhos), 4,6-bis (diphenylphosphanyl)-10H-phenoxazine (NiXantPhos), 1,2-bis(diphenylphosphino)ethane (dppe), 1,1-bis(diphenylphosphino)methane (dppm), 1,3-bis(diphenylphosphino)propane (dppp), 1,4-bis(diphenylphosphino) butane (dppb), 2,2'-bis(diphenylphosphino)-1,1'-binaphthyl (BINAP), bis[(2-diphenylphosphino) phenyl] ether (DPEPhos), 1,2-bis(dichlorophosphino) ethane, and 1,2-bis (dicyclohexylphosphino)-ethane (dcpe).

In certain embodiments, the base comprises sodium carbonate. In other embodiments, the organic solvent comprises methanol. In yet other embodiments, the precatalyst precipitates from the reaction mixture. In yet other embodiments, the mixed salt comprises [E]MX$_2$, wherein [E] is Na$_2$, K$_2$, Ca or Mg. In yet other embodiments, the mixed salt comprises Na$_2$PdCl$_2$. In yet other embodiments, the mixed alkaline/transition metal salt or a mixed alkaline-earth/transition metal salt is prepared by contacting MX$_2$ with an alkaline or alkaline-earth salt in solution.

In certain embodiments, the ligand contemplated within the invention is an N-heterocyclic carbene.

In certain embodiments, the first reagent is an aromatic or heteroaromatic boronic acid or ester, and the second reagent is an aromatic or heteroaromatic halide, tosylate, triflate, mesylate, sulfamate or carbamate. In other embodiments, the first reagent is an aromatic or heteroaromatic amine, and the second reagent is an aromatic, heteroaromatic or vinylic halide, tosylate, triflate, mesylate, sulfamate or carbamate.

In yet other embodiments, the first reagent is an aromatic or heteroaromatic zinc halide, and the second reagent is an aromatic, heteroaromatic or vinylic halide, tosylate, triflate, mesylate, sulfamate or carbamate. In yet other embodiments, the first reagent is an aromatic or heteroaromatic magnesium halide, and the second reagent is an aromatic, heteroaromatic or vinylic halide, tosylate, triflate, mesylate, sulfamate or carbamate.

In yet other embodiments, the first reagent is an aromatic or heteroaromatic tin halide, and the second reagent is an aromatic, heteroaromatic or vinylic halide, tosylate, triflate, mesylate, sulfamate or carbamate. In yet other embodiments, the first reagent is a ketone, aldehyde, imine, amide or ester, and the second reagent is an aromatic, heteroaromatic or vinylic halide, tosylate, triflate, mesylate, sulfamate or carbamate. In yet other embodiments, the first reagent is an alcohol or thiol, and the second reagent is an aromatic, heteroaromatic or vinylic halide, tosylate, triflate, mesylate, sulfamate or carbamate. In yet other embodiments, the first reagent is an aromatic or heteroaromatic silanol, siloxane or silane, and the second reagent is an aromatic, heteroaromatic or vinylic halide, tosylate, triflate, mesylate, sulfamate or carbamate.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a set of molecular structures illustrating commercially available precatalysts with a 1:1 Pd-to-ligand ratio, including precatalysts (1) and (2).

FIG. 2 is a set of exemplary reaction schemes that can be performed using the precatalysts of the invention.

DETAILED DESCRIPTION OF THE INVENTION

Figure 3:
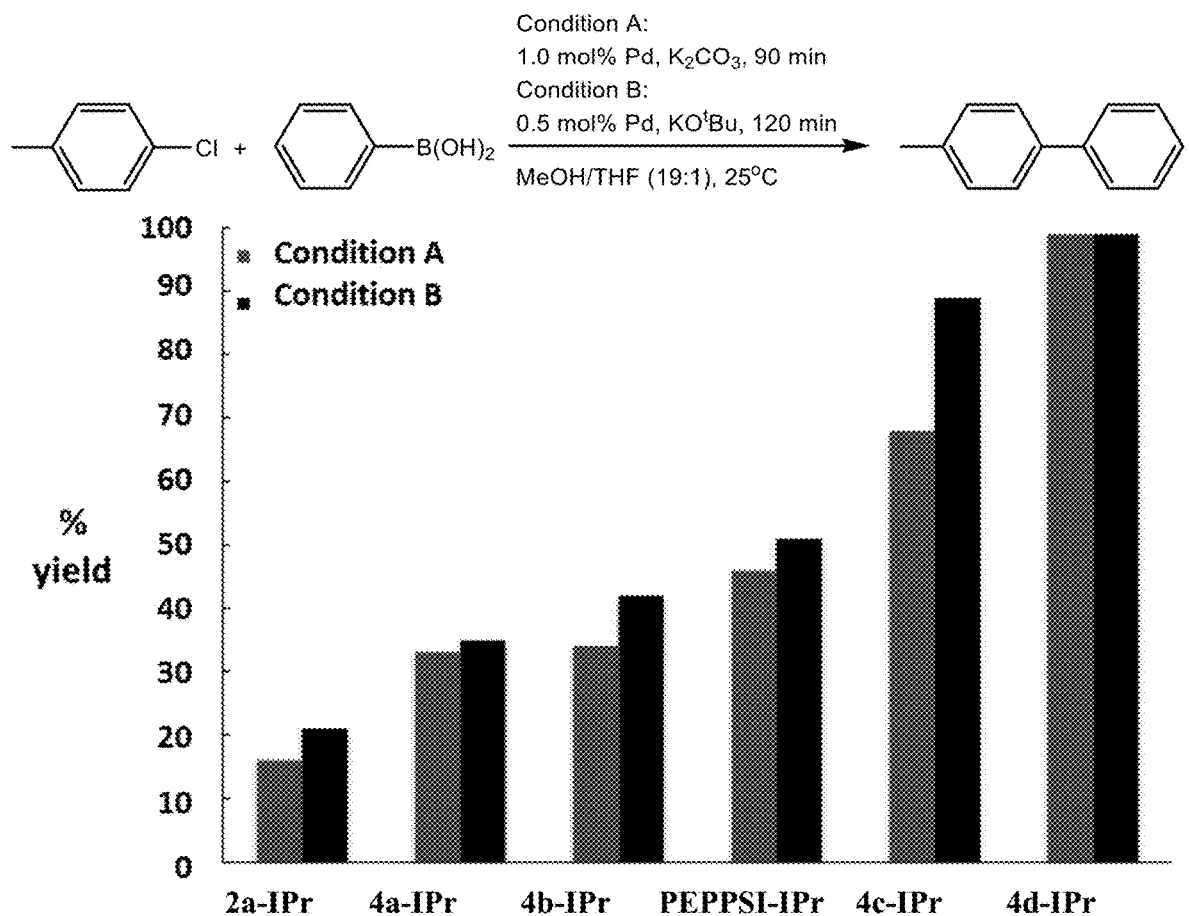
FIG. 3 is a graph illustrating yields (as determined by gas chromatography, or GC) for Suzuki-Miyaura reactions catalyzed by distinct precatalysts.

The present invention relates to the unexpected discovery of novel transition-metal precatalysts that are useful in preparing active coupling catalysts. In certain embodiments, the precatalysts of the invention are air-stable and moisture-stable. In other embodiments, the precatalysts of the invention comprise a dimeric precatalyst of formula (I) or a monomeric precatalyst of formula (II). The present invention further provides methods of making and using the precatalysts of the invention.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. A specific example is ($C_1$-$C_3$)alkoxy, such as, but not limited to, ethoxy and methoxy.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. A selected example is ($C_1$-$C_6$)alkyl, such as, but not limited to, ethyl, methyl, isopropyl, isobutyl, n-pentyl, n-hexyl and cyclopropylmethyl.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR', wherein each occurrence of R' is independently H, alkyl, substituted alkyl, alkenyl or substituted alkenyl, with the proviso that at least one R' group is not hydrogen. The term "substituted homopropargylic" refers to a group exemplified by —$CR'_2CR'_2$—C≡CR', wherein each occurrence of R' is independently H, alkyl, substituted alkyl, alkenyl or substituted alkenyl, with the proviso that at least one R' group is not hydrogen.

As used herein, the term "AmPhos" refers to di-t-butylphosphino-4-dimethylaminobenzene.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl.

As used herein, the term "aryl-($C_1$-$C_3$)alkyl" refers to a functional group wherein a one to three carbon alkylene chain is attached to an aryl group, e.g., —$CH_2CH_2$-phenyl or —$CH_2$-phenyl (benzyl). Specific examples are aryl-$CH_2$— and aryl-CH($CH_3$)—. The term "substituted aryl-($C_1$-$C_3$) alkyl" refers to an aryl-($C_1$-$C_3$)alkyl functional group in which the aryl group is substituted. A specific example is substituted aryl($CH_2$)—. Similarly, the term "heteroaryl-($C_1$-$C_3$)alkyl" refers to a functional group wherein a one to three carbon alkylene chain is attached to a heteroaryl group, e.g., —$CH_2CH_2$-pyridyl. A specific example is heteroaryl-($CH_2$)—. The term "substituted heteroaryl-($C_1$-$C_3$)alkyl" refers to a heteroaryl-($C_1$-$C_3$)alkyl functional group in which the heteroaryl group is substituted. A specific example is substituted heteroaryl-($CH_2$)—.

As used herein, the term "cycloalkyl," by itself or as part of another substituent refers to, unless otherwise stated, a cyclic chain hydrocarbon having the number of carbon atoms designated (i.e., $C_3$-$C_6$ refers to a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Other examples are ($C_3$-$C_6$)cycloalkyl, such as, but not limited to, cyclopropyl, cyclobutyl, cyclopentyl and cyclohexyl.

As used herein, the term "DavePhos" refers to 2-dicyclohexylphosphino-2'-(N,N-dimethylamino)biphenyl.

As used herein, the term "dvds" refers to 1,3-divinyl-1, 1,3,3-tetramethyl disiloxane.

As used herein, the term "halide" refers to a halogen atom bearing a negative charge. The halide anions are fluoride ($F^-$), chloride ($Cl^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "IPr" refers to 1,3-bis(2,6-diisopropylphenyl)-1,3-dihydro-2H-imidazol-2-ylidene.

As used herein, the term "IPr*OMe" refers to 1,3-bis(2,6-bis-(diphenylmethyl)-4-methoxyphenyl)imidazol-2-ylidene.

As used herein, the term "ligand" refers to any organic or inorganic molecule or ion that is capable of coordinating to a metal center. In certain embodiments, the ligand comprises one or more lone electron pairs that can coordinate with a metal center.

As used herein, the term "precatalyst" refers to a transition-metal-containing complex that, under specific reaction conditions, is converted to an active cross-coupling catalyst. In certain embodiments, the precatalyst is dimeric, i.e., contains two transition metals per molecule. In other embodiments, the precatalyst is monomeric, i.e., contains one transition metal per molecule. In yet other embodiments, conversion of the precatalyst to the active cross-coupling catalyst comprises contacting the precatalyst with a selected ligand.

As used herein, the term "QPhos" refers to 1,2,3,4,5-pentaphenyl-1'-(di-tert-butylphosphino)ferrocene.

As used herein, the term "RuPhos" refers to 2-dicyclohexylphosphino-2',6'-diisopropoxybiphenyl.

As used herein, the term "SPhos" refers to 2-dicyclohexylphosphino-2',6'-dimethoxybiphenyl.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined above, substituted by one, two or three substituents selected from the group consisting of halogen, —OH, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

For aryl, aryl-(C$_1$-C$_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In another embodiment, the substituents vary in number between one and three. In yet another embodiment, the substituents vary in number between one and two. In yet another embodiment, the substituents are independently selected from the group consisting of C$_{1-6}$ alkyl, —OH, C$_{1-6}$ alkoxy, halo, amino, acetamido and nitro. As used herein, where a substituent is an alkyl or alkoxy group, the carbon chain may be branched, straight or cyclic.

As used herein, the term "XPhos" refers to 2-dicyclohexylphosphino-2',4',6'-triisopropylbiphenyl.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

DESCRIPTION

The present invention relates to the unexpected discovery of novel transition-metal precatalysts that are useful in preparing active coupling catalysts. In certain embodiments, the precatalysts of the invention are air-stable and moisture-stable. The present invention provides methods of making and using the precatalysts of the invention.

Figure 4:
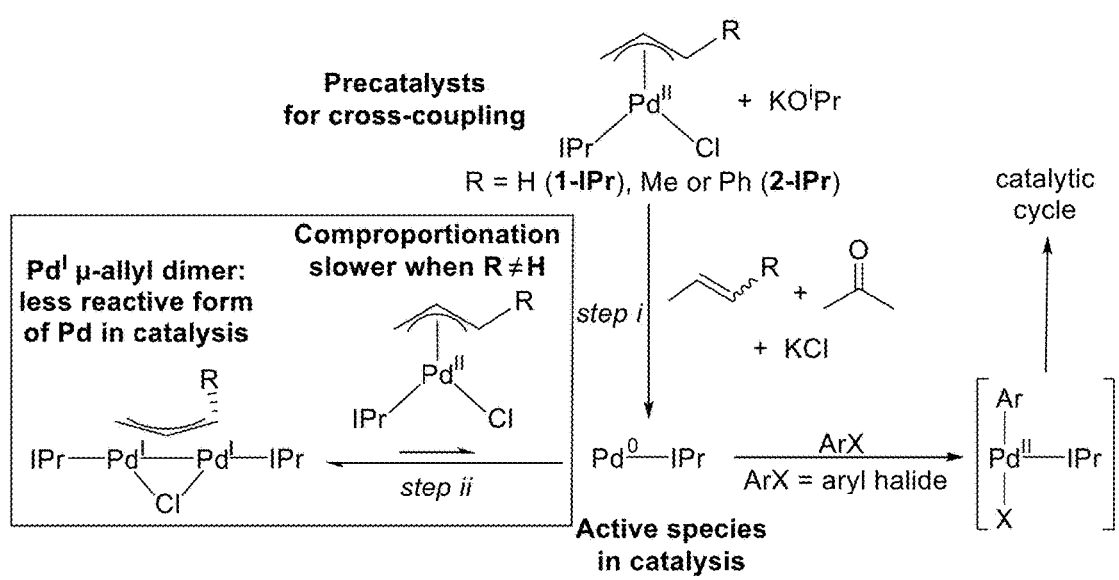
FIG. 4 is a scheme illustrating a pathway for activation of precatalysts of the type $(\eta^3\text{-allyl})Pd(IPr)(Cl)$ with $KO^iPr$ (generated from $KO^tBu$ in $^iPrOH$). Both the rate of activation to Pd(0) (step i) and comproportionation to Pd(I) (step ii) affect catalytic activity.

In one aspect, a key feature in the effectiveness of the Pd(II) precatalysts is the rate and efficiency of their conversion into the monoligated L-Pd(0) active species under the reaction conditions. For example, the efficiency of Nolan type (η$^3$-allyl)Pd(NHC)(Cl) precatalysts relates to two factors: (i) the rate of activation of the ligated precatalyst scaffold to form the catalytically active L-Pd(0) species and (ii) comproportionation between L-Pd(0) and the starting precatalyst, which forms a Pd(I) μ-allyl dimer of the form (μ-allyl)(μ-Cl)Pd$_2$(L)$_2$ and removes the L-Pd(0) from the reaction mixture (FIG. 4). In certain embodiments, monomeric precatalysts with substituents in the 1-position of the allyl ligand are active because they are less likely to comproportionate with monoligated L-Pd(0) to form Pd(I) dimers. As a result, the active L-Pd(0) preferably undergoes oxidative addition with the substrate, rather than be sequestered into the less reactive dimeric form. However, even in the case of the most active 1-substituted precatalysts some Pd (~35%) may be trapped in the form of the Pd(I) dimer.

As demonstrated herein, improved precatalysts can be designed by further increasing the barrier to comproportionation. In certain embodiments, the speed at which the Pd(II) precatalyst is converted into Pd(0) is increased, so that the conversion of Pd(II) to Pd(0) is significantly faster than deleterious comproportionation between Pd(II) and Pd(0) to form Pd(I). In certain embodiments, the precatalysts of the invention take part in catalysis without forming significant amounts of inactive Pd(I) dimers. In other embodiments, the precatalysts of the invention are compatible with phosphine or N-heterocyclic carbene (NHC) ligands.

The present disclosure provides the first comprehensive insight into the conversion of Pd(II) to Pd(0) for precatalysts of the type ($\eta^3$-allyl)Pd(IPr)(Cl) under conditions that are typically used for the Suzuki-Miyaura reaction. The present disclosure further provides the new precatalyst ($\eta^3$-1-$^t$Bu-indenyl)Pd(IPr)(Cl), which is significantly more efficient than ($\eta^3$-cinnamyl)Pd(IPr)(Cl) for the Suzuki-Miyaura reaction with both weak and strong base. In certain embodiments, the dimeric compound ($\eta^3$-1-$^t$Bu-indenyl)$_2$($\mu$-Cl)$_2$Pd$_2$ is used as a precatalyst in combination with an appropriate ligand, and is also superior to its dimeric analogue ($\eta^3$-cinnamyl)$_2$($\mu$-Cl)$_2$Pd$_2$.

In certain embodiments, the novel precatalyst scaffold of the invention can be used at least in the following reactions: Suzuki-Miyaura, Buchwald-Hartwig, Kumada, Sonogashira, Heck, C—S and C—O bond formation, α-arylation of aldehydes, α-arylation of ketones, α-arylation of amides, α-arylation of heterocycles, and anaerobic oxidation of alcohols.

Synthesis of Pd(II) Indenyl Complexes

The current synthesis of the indenyl dimer ($\eta^3$-indenyl)$_2$($\mu$-Cl)$_2$Pd$_2$ (3a), which can be converted into the monomeric compound ($\eta^3$-indenyl)Pd(IPr)(Cl) (4a-IPr) through reaction with the appropriate free ligand, requires three steps and utilizes air-sensitive reagents.

Figure 5:
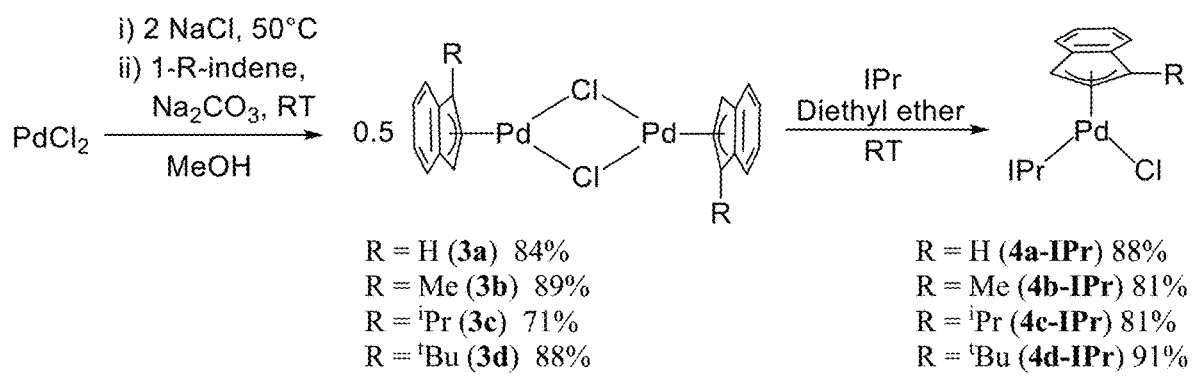
FIG. 5 is a scheme illustrating the synthesis of the indenyl precatalyst scaffold and IPr supported precatalysts.

As demonstrated herein, this reaction may be performed as a one-pot synthesis under aerobic conditions, without the use of air sensitive reagents (FIG. 5). In the synthesis of the invention, one equivalent of Na$_2$PdCl$_4$ (generated in situ from PdCl$_2$ and two equivalents of NaCl) was treated with indene and Na$_2$CO$_3$ in MeOH. The mixture was stirred for two hours at room temperature. During this time, a brown solid precipitated out of solution, which was then filtered and washed successively with water and diethyl ether to give 3a in high yield (84%) and purity. This method was also used to prepare three related substituted indenyl dimers, ($\mu^3$-1-R-indenyl)$_2$($\mu$-Cl)$_2$Pd$_2$ (R=Me (3b), $^i$Pr (3c) or $^t$Bu (3d)), in good yield (>70% in all cases), by starting with the appropriately substituted indene. Alternatively NaHCO$_3$ can be used as the base in the synthesis of 3d, with no decrease in yield.

Subsequently, the dimeric complexes were treated with two equivalents of IPr to generate the monomeric complexes ($\eta^3$-1-R-indenyl)Pd(IPr)(Cl) (R=H (4a-IPr), Me (4b-IPr), Pr (4c-IPr) or $^t$Bu (4d-IPr)) in high yield (~80%). The new complexes 4b-IPr, 4c-IPr and 4d-IPr were fully characterized. Overall, the novel two-step synthesis of 4a-IPr is a significant improvement on the earlier reported synthesis.

Activation of Pd(II) to Pd(0)

In certain embodiments, the rate determining step in the formation of Pd(0) from a ($\eta^3$-allyl)Pd(IPr)(Cl) involves the transformation of the $\eta^3$-allyl type ligand into an $\eta^1$-allyl ligand. In other embodiments, the transformation is easier for 1-substituted species due to steric factors. In yet other embodiments, the transformation proceeds at a higher rate for 1,3-disubstituted $\eta^3$-allyl ligands, such as $\eta^3$-indenyl ligands.

The rates of activation of complexes containing $\eta^3$-allyl, $\eta^3$-cinnamyl and $\eta^3$-indenyl ligands were compared, and the results obtained allowed for the elucidation of the mechanism for the conversion of Pd(II) into Pd(0). The rates of conversion of the Pd(II) complexes 1-IPr, 2-IPr, 4a-IPr and 4d-IPr into Pd(0) were studied by treating these compounds with base in the presence of ten equivalents of 1,3-divinyl-1,1,3,3-tetramethyldisiloxane (dvds) (Table 1). In all cases, the product of these reactions are the Pd(0) complex (IPr)Pd(dvds), along with various different organic by-products (Table 2). These reactions model the initial reduction from Pd(II) to Pd(0) in catalysis, where oxidative addition to the unstable monoligated Pd(0) complex subsequently occurs to start the catalytic process.

Three different types of reaction conditions, which are relevant to catalysis, were examined. The first set of conditions involved KO$^t$Bu as the base and d$_8$-$^i$PrOH as the solvent (a small amount of d$_8$-THF was also added to ensure homogenous reaction conditions). The second set of conditions involved K$_2$CO$_3$ and d$_4$-MeOH as the solvent. Under these conditions, K$_2$CO$_3$ was not soluble and 1,4,7,10,13,16-hexaoxacyclooctadecane (18-crown-6) was used as a solubilizing agent. The third set of conditions involved KO$^t$Bu as the base and d$_4$-MeOH as the solvent.

TABLE 1

Rates of activation of 1-IPr, 2-IPr, 4a-IPr or 4d-IPr in the presence of dvds.[a]

1-IPr, 2-IPr, 4a-IPr or 4d-IPr + 10 eq base + 10 eq 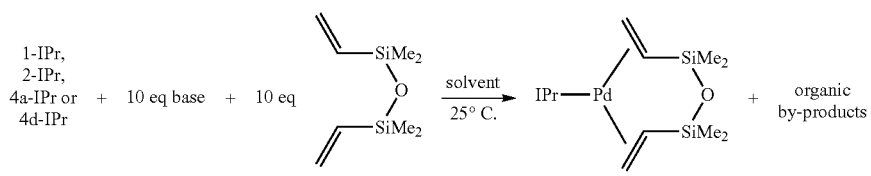 $\xrightarrow{\text{solvent}}$ IPr—Pd + organic by-products
25° C.

PhB(OH)$_2$ | Rate of activation $k_{obs}$ (s$^{-1}$)[e]

| Base | Solvent | present | 1-IPr | 2-IPr | 4a-IPr | 4d-IPr |
|------|---------|---------|-------|-------|--------|--------|
| KO$^t$Bu | d$_8$-$^i$PrOH[b] | No | 5.6 ± 0.1 * 10$^{-4}$ | 3.80 ± 0.03 * 10$^{-3}$ | >7.7 * 10$^{-3}$ (4.8 ± 0.1 * 10$^{-3}$)[f] | >7.7 * 10$^{-3}$ (5.3 ± 0.2 * 10$^{-3}$)[f] |

TABLE 1-continued

Rates of activation of 1-IPr, 2-IPr, 4a-IPr or 4d-IPr in the presence of dvds.[a]

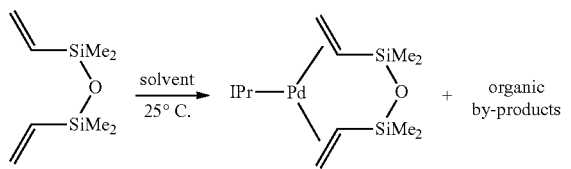

| Base | Solvent | PhB(OH)$_2$ present | Rate of activation $k_{obs}$ (s$^{-1}$)[e] | | | |
|------|---------|---------|------|------|------|------|
| | | | 1-IPr | 2-IPr | 4a-IPr | 4d-IPr |
| KO$^t$Bu | d$_4$-MeOH | No | 1.80 ± 0.02 * 10$^{-3}$ | 5.1 ± 0.1 * 10$^{-4}$ | >7.7 * 10$^{-3}$ (5.3 ± 0.2 * 10$^{-3}$)[f] | >7.7 * 10$^{-3}$ (5.7 ± 0.1 * 10$^{-3}$)[f] |
| K$_2$CO$_3$ | d$_4$-MeOH[c] | No | 9.6 ± 0.2 * 10$^{-4}$ | 4.2 ± 0.1 * 10$^{-4}$ | >7.7 * 10$^{-3}$ (4.7 ± 0.1 * 10$^{-3}$)[f] | >7.7 * 10$^{-3}$ (5.0 ± 0.2 * 10$^{-3}$)[f] |
| K$_2$CO$_3$ | d$_4$-MeOH[c] | Yes[d] | 2.4 ± 0.1 * 10$^{-4}$ | 1.4 ± 0.2 * 10$^{-4}$ | 7.2 ± 0.1 * 10$^{-4}$ | 7.6 ± 0.1 * 10$^{-4}$ |

[a]Reaction conditions: 0.0087 mmol 1-IPr, 2-IPr, 4a-IPr or 4d-IPr 0.087 mmol of base, 0.087 mmol of dvds in 500 µL of solvent.
[b]100 µL of d$_8$-THF was added along with only 400 µL of $^i$PrOH.
[c]Two equivalents of 18-crown-6 (compared to K$_2$CO$_3$) were added to solubilize K$_2$CO$_3$.
[d]0.0087 mmol precatalyst, 0.087 mmol phenylboronic acid, 0.096 mmol base, 0.087 mmol dvds in 500 µL d$_4$-MeOH.
[e]All rates are the average of at least two runs.
[f]Experiments performed at 0° C.

TABLE 2

By-products from activation of 1-IPr, 2-IPr, 4a-IPr or 4d-IPr in the presence of dvds.[a]

| Base | Solvent | PhB(OH)$_2$ present | By-products from activation | | | |
|------|---------|---------|------|------|------|------|
| | | | 1-IPr | 2-IPr | 4a-IPr | 4a-IPr |
| KO$^t$Bu | d$_8$-$^i$PrOH | No | propene, acetone | allylbenzene, acetone | indene, acetone | 1-$^t$Bu-indene, acetone |
| KO$^t$Bu | d$_4$-MeOH | No | propene, formaldehyde | allylbenzene, formaldehyde | indene, formaldehyde | 1-$^t$Bu-indene, formaldehyde |
| K$_2$CO$_3$ | d$_4$-MeOH | No | propene, formaldehyde | allylbenzene, formaldehyde | indene, formaldehyde | 1-$^t$Bu-indene, formaldehyde |
| K$_2$CO$_3$ | d$_4$-MeOH | Yes | propene, formaldehyde | allylbenzene, formaldehyde | indene, formaldehyde | 1-$^t$Bu-indene, formaldehyde |

[a]The same reaction conditions described in Table 1 were utilized, with the exception that protio rather than deuterated solvents were utilized to determine the organic by-products originating from the solvent.

The indenyl complexes 4a-IPr and 4d-IPr were activated the fastest in all cases. In many instances, the activation was so fast that only a minimum rate could be estimated at 25° C. using $^1$H NMR spectroscopy. A series of reactions analogous to those described in Table 1 at 0° C., allowed us to establish that 4d-IPr activates slightly faster than 4a-IPr. As expected, using the traditional cross-coupling conditions for the Suzuki-Miyaura reaction of KO$^t$Bu in d$_8$-$^i$PrOH, the cinnamyl species 2-IPr underwent significantly faster activation than the unsubstituted species 1-IPr. However, under the conditions developed for cross-coupling with weak base (K$_2$CO$_3$ in d$_4$-MeOH), 1-IPr underwent more rapid activation than 2-IPr. When the base was changed from K$_2$CO$_3$ to KO$^t$Bu in d$_4$-MeOH, slightly faster activation was observed for both 1-IPr and 2-IPr, and the rate for the unsubstituted species 1-IPr was again faster than for 2-IPr.

The organic byproducts of activation were identified and quantified using either H or $^{13}$C NMR spectroscopy. Under all conditions, propene, allylbenzene, indene and 1-$^t$Bu-indene were observed as by-products in activation studies using 1-IPr, 2-IPr, 4a-IPr and 4d-IPr, respectively, in >95% yield. In addition, for all reactions performed in $^i$PrOH, acetone was formed in high yield as determined using $^{13}$C NMR spectroscopy. Without wishing to be limited by any theory, in reactions performed in MeOH formaldehyde may be a byproduct.

Figure 6:
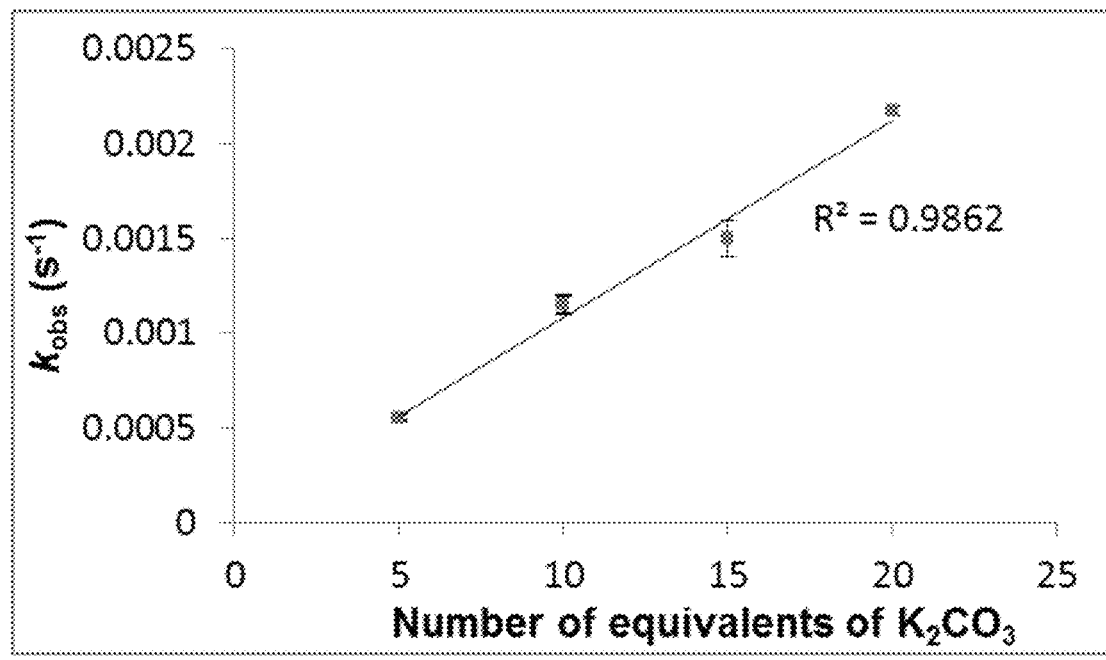
FIG. 6 is a graph of the observed rate constant vs. number of equivalents of base for the activation of 1 in $d_4$-MeOH with $K_2CO_3$ in the presence of 1,3-divinyl-1,1,3,3-tetramethyldisiloxane (dvds).

In certain embodiments, the appearance of related byproducts in the activation of 1-IPr, 2-IPr, 4a-IPr and 4d-IPr suggests that the reactions follow a similar mechanism. Consistent with this observation, all reactions were first order in Pd. A series of experiments using 1-IPr as a representative compound indicated that, regardless of the solvent and choice of base, the activation of 1-IPr was 1$^{st}$ order in base (FIG. 6). In agreement with the concentration of base effecting the rate of activation, when experiments were performed in the presence of ten equivalents of phenylboronic acid (a coupling partner in the Suzuki-Miyaura reaction), slower rates were observed. However, the reaction byproducts were still the same, indicating that a pathway for activation that involves initial transmetalation of the boronic acid, followed by reductive elimination, does not occur. Without wishing to be limited by any theory, the boronic acid reduces the effective concentration of the base, rather than playing a direct role in activation.

In the absence of dvds, the Pd containing products of the activation of 1-IPr, 2-IPr and 4a-IPr were Pd(I) dimers with bridging allyl or indenyl ligands, while the organic byproducts were the same as those observed with dvds. However, the Pd(I) dimers were not soluble under the reaction conditions, which precluded careful kinetic analysis of the data. Nevertheless, qualitative analysis indicated that activation experiments performed in the absence of dvds gave the same trends as those in the presence of dvds, with the indenyl complex 4a-IPr activating significantly faster than either 1-IPr or 2-IPr (Table 3). Without wishing to be limited by any theory, conclusions made about the rate of activation in the presence of dvds are relevant to the catalytic system which does not contain dvds.

TABLE 3

Rates of activation of 1-IPr, 2-IPr or 4a-IPr in the absence of dvds.[a]

| | | Time to completion (minutes)[e] | | |
|---|---|---|---|---|
| Base | Solvent | 1-IPr | 2-IPr | 4a-IPr |
| KO$^t$Bu | d$_8$-$^i$PrOH[b] | 150 | 90 | 40 |
| KO$^t$Bu | d$_4$-MeOH | 120 | 150 | 30 |
| K$_2$CO$_3$[c] | d$_4$-MeOH | 160 | 180 | 40 |

[a]Reaction conditions: 0.0087 mmol 1-IPr, 2-IPr or 4a-IPr, 0.087 mmol of base in 500 μL of solvent.
[b]100 μL of d$_8$-THF was added along with only 400 μL of $^i$PrOH.
[c]Two equivalents of 18-crown-6 (compared to K$_2$CO$_3$) were added to solubilize the K$_2$CO$_3$.
[d]0.0087 mmol precatalyst, 0.087 mmol phenylboronic acid, 0.096 mmol base in 500 μL d$_4$-MeOH.
[e]All times to complexes are the average of at least two runs.

Catalytic Experiments and Pd(I) Dimer Formation

As demonstrated herein, the indenyl systems 4a-IPr and 4d-IPr were reduced faster from Pd(II) to Pd(0) than the cinnamyl system 2-IPr, under varying conditions. In certain embodiments, 4a-IPr and 4d-IPr are better precatalysts for the Suzuki-Miyaura reaction if deleterious side reactions that remove Pd(0) from the catalytic mixture are minimized. 2-IPr and the family of indenyl complexes 4a-IPr-4d-IPr were tested as precatalysts for a Suzuki-Miyaura reaction involving an aryl chloride using both weak (K$_2$CO$_3$) and strong (KO$^t$Bu) bases (FIG. 3). The results show that the indenyl-supported precatalysts were more active than the cinnamyl supported species under both sets of conditions, which is consistent with faster reduction from Pd(II) to Pd(0) under the catalytic conditions. Furthermore, as the size of the substituent on the η$^3$-indenyl ligand was increased the precatalysts became more active, with 4d-IPr being the most efficient precatalyst.

FIG. 3 illustrates the % yield obtained using the indenyl complexes 4a-IPr, 4b-IPr, 4c-IPr and 4d-IPr as precatalysts for the Suzuki-Miyaura reaction of 4-chlorotoluene with phenylboronic acid, using both weak (K$_2$CO$_3$) and strong (KO$^t$Bu) base in a 19:1 MeOH:THF mixture (Conditions A and B, respectively). For comparison, both Nolan's (η$^3$-cinnamyl)Pd(Cl)(IPr) (also known as 2a-IPr) and Organ's (3-chloropyridine)Pd(Cl)$_2$(IPr) (also known as PEPPSI-IPr) precatalysts were included. The same trends in precatalyst performance were observed under both sets of reaction conditions. All of the indenyl supported precatalysts were more active than 2a-IPr, and both 4c-IPr and 4d-IPr were also significantly more active than PEPPSI-IPr. The indenyl-supported precatalysts become more active as the size of the substituent on the indenyl ligand was increased, with 4d-IPr being the most efficient system.

In the case of η$^3$-allyl systems, the tendency of the precatalyst and monoligated Pd(0) to comproportionate to generate a Pd(I) dimer, a less reactive form during catalysis, decreased as the steric bulk on the η$^3$-allyl ligand increased (FIG. 4). In order to probe if a similar effect was occurring in indenyl systems, the tendency of the least sterically bulky (4a-IPr) and most sterically bulky (4d-IPr) precatalysts to dimerize was examined.

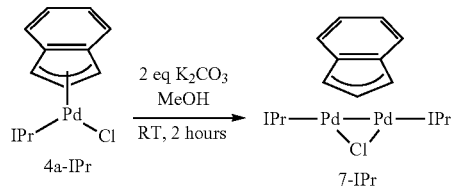

(Eq 1)

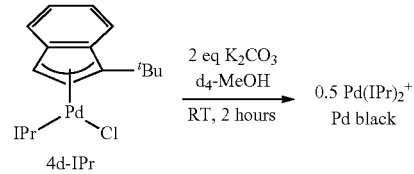

(Eq 2)

The unsubstituted indenyl dimer 7-IPr was prepared in 85% yield through the treatment of 4a-IPr with K$_2$CO$_3$ in EtOH (Eq 1). Compound 7-IPr was fully characterized, including by X-ray crystallography. In contrast to complex 4a-IPr, no dimer formation was observed when 4d-IPr was treated with K$_2$CO$_3$ (Eq 2). Instead, only Pd(0) products were observed in the reaction mixture. This observation suggests that Pd(I) dimer formation via comproportionation is more difficult for indenyl systems with greater steric bulk.

Catalysis

In order to confirm that indenyl-based systems were superior to the cinnamyl precatalyst 2-IPr, a head to head comparison was performed between 4d-IPr and 2-IPr using a range of different substrates for the Suzuki-Miyaura reaction using both a weak and strong base (Table 4). In all cases 4d-IPr was a significantly better precatalyst than 2-IPr and was able to couple a variety of different aryl chloride substrates at room temperature. This included substrates with deactivating electron donating groups and substituents in the ortho positions. The improvement from 2-IPr to 4d-IPr was most pronounced using weak base compared to strong base and occurred regardless of the catalyst loading. Nolan type precatalysts had not been shown to afford full conversion for Suzuki-Miyaura reactions with weak base, so the quantitative yields obtained with 4d-IPr represent a significant improvement and could expand the range of viable substrates with this catalytic system.

TABLE 4

Yields[a] of product for Suzuki-Miyaura reactions[b] catalyzed by 2-IPr and 4d-IPr.

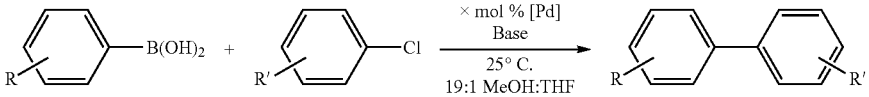

|  |  | Cat. Loading | Time | % Yield for Precatalysts | |
|---|---|---|---|---|---|
| Product | Base | (mol %) | (min) | 2 | 4d-IPr |
| 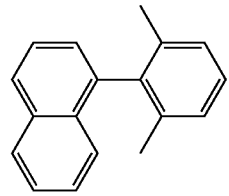 [SMILES: Cc1cccc(C)c1-c1cccc2ccccc12] | KO$^t$Bu<br>K$_2$CO$_3$ | 0.5<br>1.0 | 120<br>45 | 21<br>29 | >99<br>>99 |
| 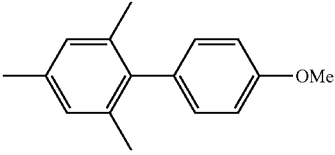 | KO$^t$Bu<br>K$_2$CO$_3$ | 0.5<br>1.0 | 120<br>120 | 46<br>15 | >99<br>>99 |
| 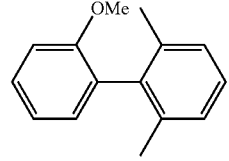 [SMILES: COc1ccccc1-c1c(C)cccc1C] | KO$^t$Bu<br>K$_2$CO$_3$ | 0.5<br>1.0 | 45<br>30 | 25<br>18 | >99<br>>99 |
| 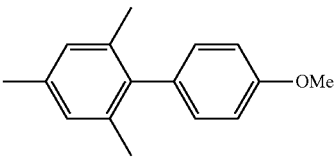 [SMILES: COc1ccc(-c2c(C)cc(C)cc2C)cc1] | KO$^t$Bu<br>K$_2$CO$_3$ | 0.1<br>0.2 | 30<br>60 | 54<br>21 | >99<br>>99 |
| 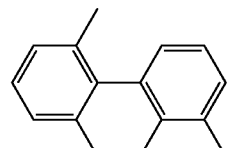 | KO$^t$Bu<br>K$_2$CO$_3$ | 0.1<br>0.2 | 120<br>60 | 25<br>21 | >99<br>>99 |
| 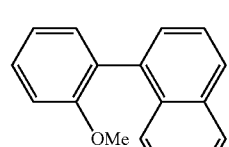 | KO$^t$Bu<br>K$_2$CO$_3$ | 0.5<br>1.0 | 120<br>120 | 41<br>22 | >99<br>>99 |
|  | KO$^t$Bu<br>K$_2$CO$_3$ | 0.1<br>0.2 | 60<br>120 | 43<br>35 | >99<br>>99 |

[a]Yields were calculated using gas chromatography with naphthalene as an internal standard and are the average of two runs.
[b]Reaction conditions KO$^t$Bu: Methanol solution containing 0.5263M aryl chloride, 0.5526M boronic acid, 0.5789M KO$^t$Bu and 0.2632M naphthalene (950 μL), THF solution containing 0.05M [Pd] (50 μL). Reaction conditions using K$_2$CO$_3$: Methanol solution containing 0.5263M aryl chloride, 0.5526M boronic acid and 0.2632M naphthalene (950 μL), THF solution containing 0.1M [Pd] (50 μL), 104 mg K$_2$CO$_3$ added to each reaction.

In Nolan's cinnamyl system, the ligand free precursor, ($\eta^3$-cinnamyl)$_2$($\mu$-Cl)$_2$Pd$_2$ may be converted into the ligated precatalyst in situ. This allows for a variety of different ligands to be rapidly screened for a reaction, without the need for the synthesis or isolation of a family of well-defined precatalysts.

The catalytic activity of an in situ generated solution of ($\eta^3$-cinnamyl)$_2$($\mu$-Cl)$_2$Pd$_2$ and two equivalents of IPr was compared with an in situ generated solution of ($\eta^3$-1-$^t$Bu-indenyl)$_2$($\mu$-Cl)$_2$Pd$_2$ (3d) and two equivalents of IPr using both weak and strong bases (Table 5). The indenyl scaffold performed significantly better than Nolan's system. This suggests that not only does do $\eta^3$-indenyl systems give more efficient isolated precatalysts but that they are a better scaffold for the screening of new ligands in situ than the traditional cinnamyl system.

Without wishing to being bound to any theory, the increased activity of precatalysts with more sterically demanding substituents on the indenyl ligand is due to the fact that Pd(I) dimers with bridging indenyl ligands are less likely to form in these cases.

Catalytic Reactions with Phosphine Supported Complexes

Figure 8:
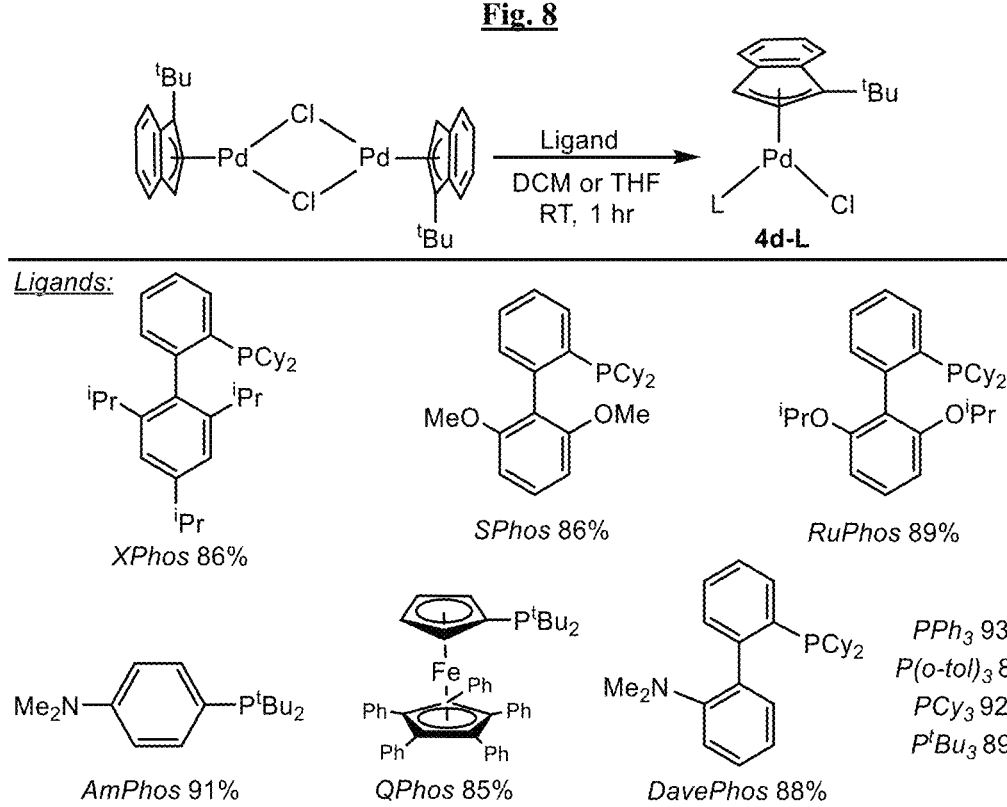
FIG. 8 illustrates preparation and yields of phosphine supported precatalysts.

Experiments were run to explore the scope of phosphines as ligands. To this end, a family of phosphine ligated complexes with the general structure ($\eta^3$-$^t$Bu-indenyl)Pd(L)(Cl) were synthesized (FIG. 8). Coordination was achieved through the addition of two equivalents of ligand to the dimeric precursor, 3d, to afford a variety of precatalysts with excellent yields. A number of state of the art ligands, including several Buchwald-type phosphines, were successfully coordinated to the dimeric scaffold.

With these complexes in hand, the phosphine supported systems were screened for currently challenging cross-coupling reactions. Heterocycles are commonly found in pharmaceuticals and natural products but traditionally represent difficult substrates for cross-coupling. For example, Suzuki-Miyaura reactions that employ boronic acids in the 2-position of 5-membered heterocycles are particularly challenging due to their tendency to undergo rapid protodeboronation. Therefore, a rapid and efficient precatalyst must be used to afford full conversion to product. Using ($\eta^3$-1-$^t$Bu-indenyl)Pd(XPhos)(Cl) (4d-XPhos) as the precatalyst, a range of 2-heterocyclic boronic acids were successfully

TABLE 5

Yields[a] of product for the Suzuki-Miyaura reaction[b] catalyzed by an in situ generated solution of ($\eta^3$-cinnamyl)$_2$($\mu$-Cl)$_2$Pd$_2$ and IPr and an in situ generated solution of ($\eta^3$-1-$^t$Bu-indenyl)$_2$($\mu$-Cl)$_2$Pd$_2$ and IPr.

PhB(OH)$_2$ + 4-Cl-C$_6$H$_4$-Me → biaryl product
× mol % [Pd] + 2× mol % IPr, Base, 25° C., 19:1 MeOH:THF

| | | % Yields for Precatalysts | |
|---|---|---|---|
| Base | Time (min) | ($\mu$-Cl)$_2$Pd$_2$($\eta^3$-cinnamyl)$_2$ | ($\mu$-Cl)$_2$Pd$_2$($\eta^3$-1-$^t$Bu-indenyl)$_2$ |
| KO$^t$Bu | 15 | <1 | 7 |
| | 30 | <1 | 30 |
| | 45 | 3 | 58 |
| | 60 | 5 | 76 |
| | 120 | 8 | >99 |
| K$_2$CO$_3$ | 30 | <1 | 37 |
| | 60 | 3 | 79 |
| | 90 | 5 | >99 |

[a]Yields were calculated using gas chromatography with naphthalene as an internal standard and are the average of two runs.
[b]Reaction conditions KO$^t$Bu: Methanol solution containing 0.5263M aryl chloride, 0.5526M boronic acid, 0.5789M KO$^t$Bu and 0.2632M naphthalene (950 µL), THF solution containing 0.05M [Pd]$_{Tot}$ 0.05M IPr (solution allowed to stir for one hour prior to use, 50 µL). Reaction conditions using K$_2$CO$_3$: Methanol solution containing 0.5263M aryl chloride, 0.5526M boronic acid and 0.2632M naphthalene (950 µL), THF solution containing 0.1M [Pd]$_{Tot}$ 0.1M IPr (solution allowed to stir for one hour prior to use, 50 µL), 104 mg K$_2$CO$_3$ added to each reaction.

Figure 7:
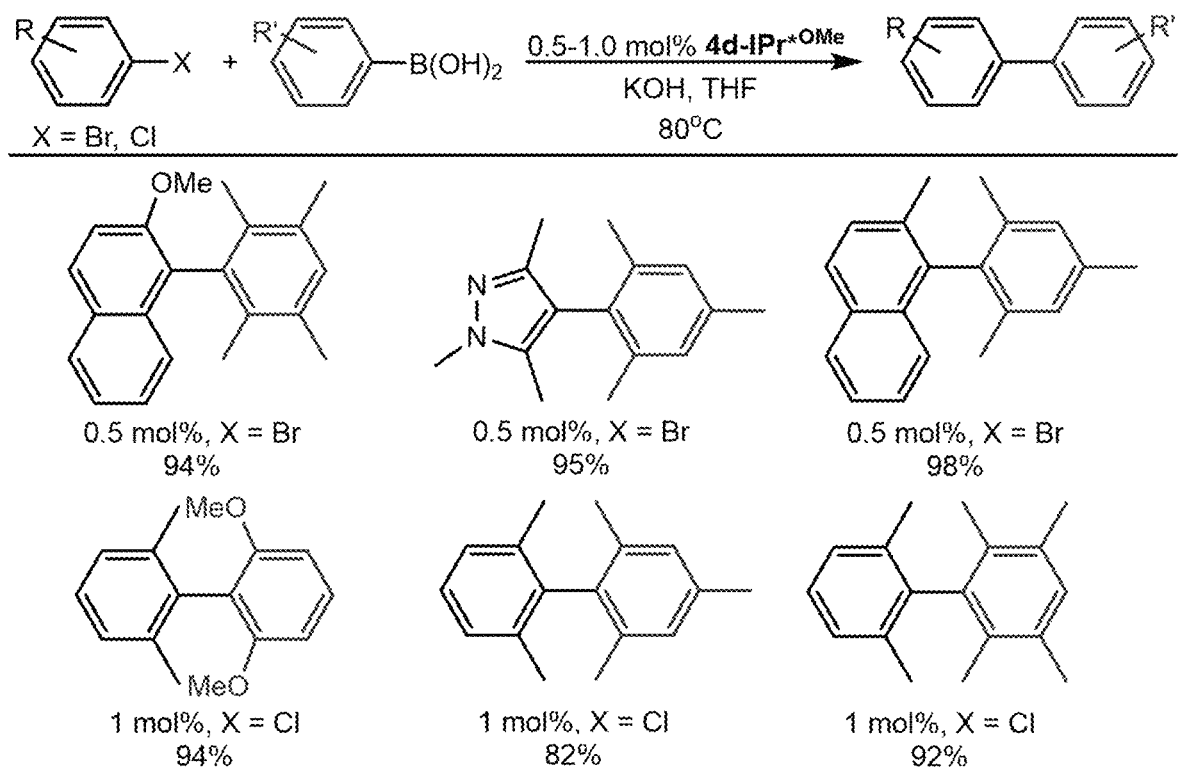
FIG. 7 illustrates product yields for a series of Suzuki-Miyaura reactions to generate tetra-ortho-substituted biaryl products catalyzed by 4d-IPr*OMe. ArX (0.50 mmol), ArB(OH)$_2$ (0.75 mmol), KOH (1.0 mmol), 4d-IPr*OMe (0.5 or 1.0 mol %), THF (1.0 mL); isolated yields average of two runs.
Figure 9:
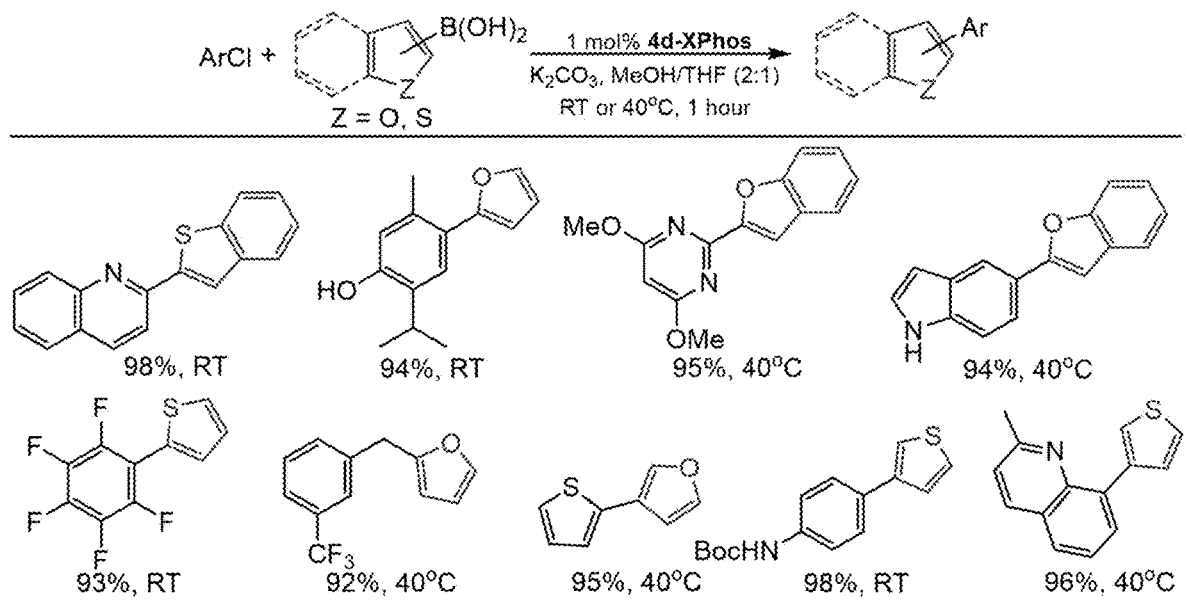
FIG. 9 illustrates yields of products for Suzuki-Miyaura reactions involving 2-heterocyclic boronic acids. ArCl (1.0 mmol), ArB(OH)$_2$ (1.5 mmol), K$_2$CO$_3$ (2.0 mmol), 4d-XPhos (1.0 mol %), MeOH (4 mL), THF (2 mL); isolated yields average of two runs.

To demonstrate that the present precatalyst scaffold is compatible with state of the art NHC ligands, Suzuki-Miyaura reactions that generate tetra-ortho-substituted biaryl products were performed (FIG. 7). For this type of challenging reaction, the sterically hindered ancillary ligand IPr*$^{OMe}$ (IPr*$^{OMe}$=1,3-bis(2,6-bis-(diphenylmethyl)-4-methoxyphenyl)imidazol-2-ylidene) is required. The complex ($\eta^3$-1-$^t$Bu-indenyl)Pd(IPr*$^{OMe}$)(Cl) or 4d-IPr*$^{OMe}$ was prepared through the reaction of IPr*$^{OMe}$ with 3d. Using 4d-IPr*$^{OMe}$ as a precatalyst, a number of tetra-ortho-substituted products were prepared in high yield. When aryl bromides were used as substrates, reactions took place at lower temperature (80° C.), compared to cinnamyl systems supported by IPr*$^{OMe}$. Furthermore, by increasing the catalyst loading to 1.0 mol %, aryl chlorides were used as substrates under the same reaction conditions. In certain embodiments, this method utilizes the mildest conditions reported to produce tetra-ortho-substituted products in high yields using aryl chlorides.

coupled to produce biaryl products in excellent yields under mild reaction conditions (FIG. 9). The present precatalysts, which give comparable or superior performance to the best known systems for this reaction, are also tolerant to a wide range of functional groups on the aryl chloride, including phenols, Boc-protected anilines and free amines.

Figure 10:
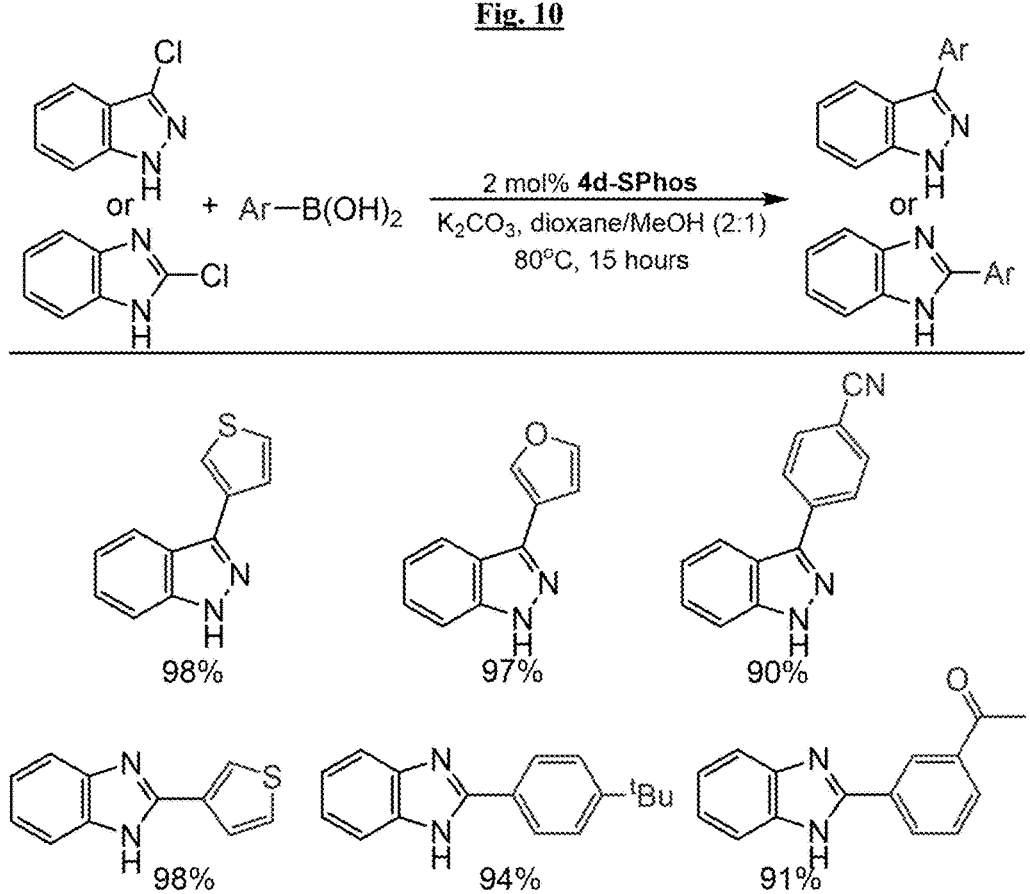
FIG. 10 illustrates yields of products for Suzuki-Miyaura reactions involving unprotected indazoles or benzimidazoles. ArCl (1.0 mmol), ArB(OH)$_2$ (2.0 mmol), K$_2$CO$_3$ (2.0 mmol), 4d-SPhos (2.0 mol %), 1,4-dioxane (4 mL), MeOH (2 mL); isolated yields average of two runs.

The compatibility of Pd-catalyzed cross-coupling methodology with substrates containing acidic, free N—H moieties is a common synthetic problem. Employing ($\eta^3$-1-$^t$Bu-indenyl)Pd(SPhos)(Cl) (4d-SPhos), yields of greater than 90% for reactions were obtained where the aryl chloride was either indazole or benzimidazole (FIG. 10). With the present catalyst system, the temperature could be lowered slightly (80° C.), with excellent yields obtained in 15 hours. In certain embodiments, this methodology supports the use of heteroaromatic boronic acids.

Figure 11:
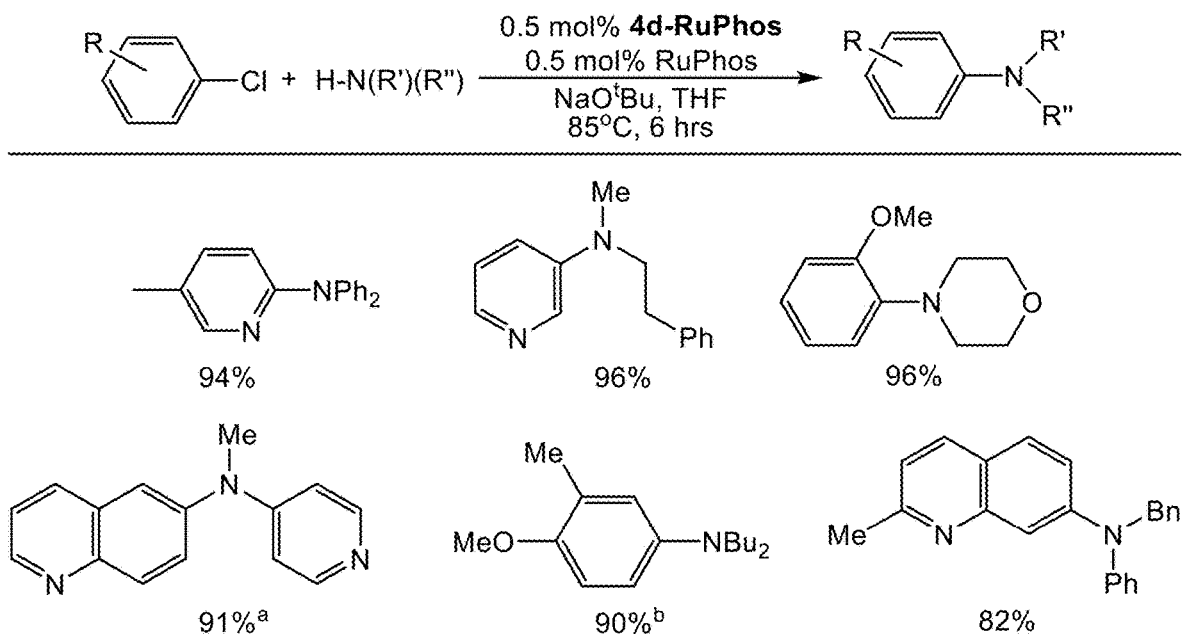
FIG. 11 illustrates yields of products for Buchwald-Hartwig reactions involving secondary amines. ArCl (1.0 mmol), Amine (1.2 mmol), NaO$^t$Bu (1.2 mmol), 4d-RuPhos (0.5 mol %), RuPhos (0.5 mol %), THF (1 mL); isolated yields average of two runs. $^a$ Used 4d-XPhos. $^b$ Used ArBr.

After the Suzuki-Miyaura reaction, the Buchwald-Hartwig coupling is the next most commonly performed cross-coupling reaction in the synthesis of pharmaceuticals. ($\eta^3$-1-$^t$Bu-indenyl)Pd(RuPhos)(Cl) (4d-RuPhos) successfully generated a selection of symmetrical and unsymmetrical tertiary amines in good to excellent yield (FIG. 11). Various aryl chlorides containing heteroatoms and ortho-substituents were compatible with the present system.

Figure 12:
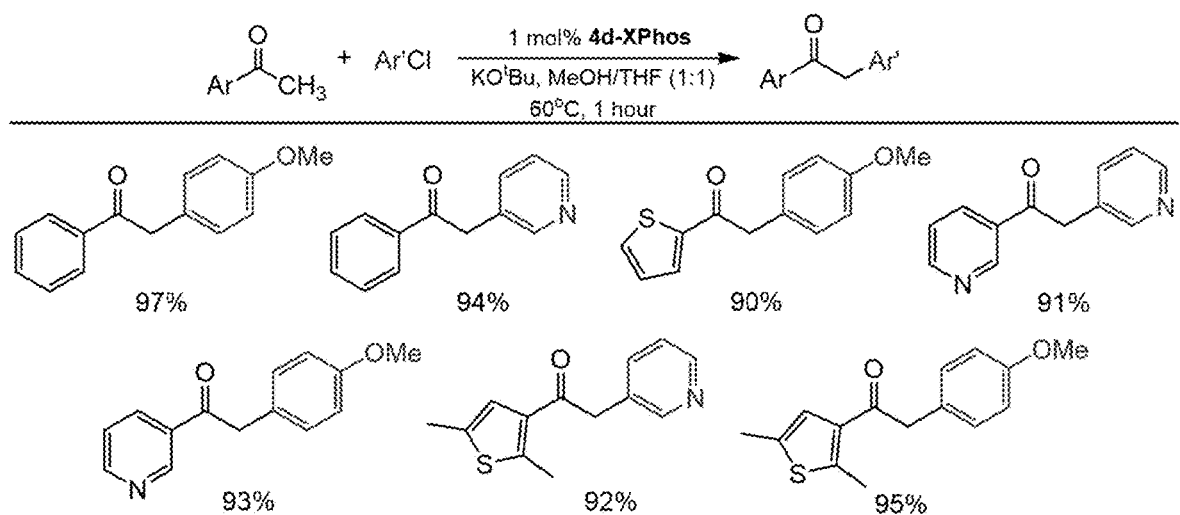
FIG. 12 illustrates yields of products from α-arylation of aryl methyl ketones. ArCl (0.53 mmol), Ketone (0.5 mmol), KO$^t$Bu (1.2 mmol), 4d-XPhos (1.0 mol %), THF (4 mL), MeOH (1 mL); isolated yields average of two runs.

The monoarylation of aryl methyl ketones is important due to the prevalence of α-aryl carbonyl moieties in organic compounds with interesting pharmacological and biological properties. However, this is a challenging reaction due to the possibility for diarylation of the ketone. Using ($\eta^3$-1-$^t$Bu-indenyl)Pd(XPhos)(Cl) (4d-XPhos) excellent results were observed for the monoarylation of a variety of methyl ketones under moderate conditions (FIG. 12). Using a 1:1 THF/MeOH mixture and KO$^t$Bu as base, heterocyclic moieties in both the aryl chloride and aryl methyl ketone were tolerated with yields greater than 90% in each case. In fact, in two cases, the products contained heterocyclic fragments in both coupling partners.

Figure 13:
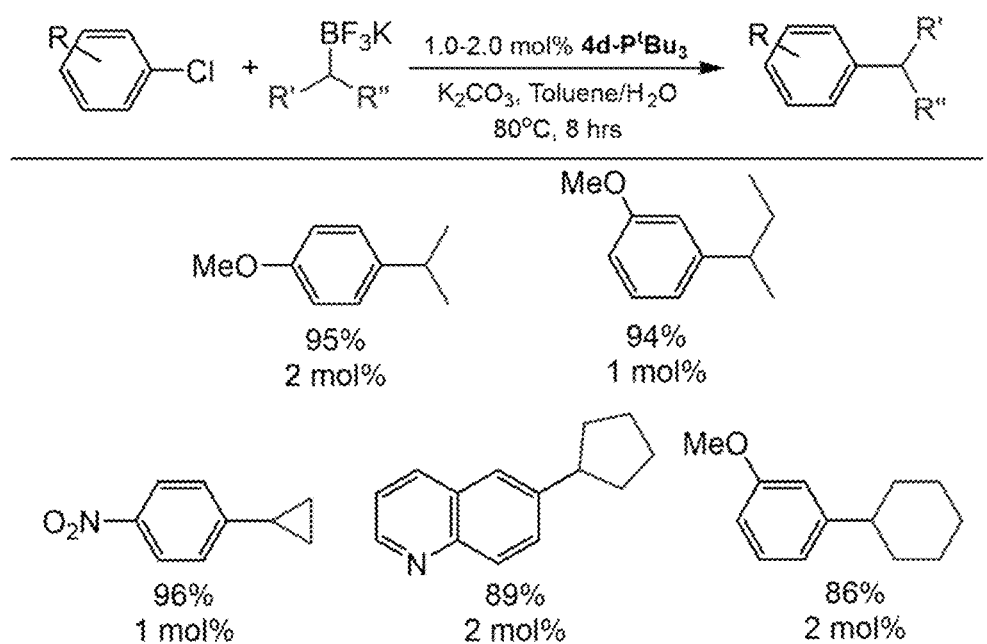
FIG. 13 illustrates yields of products for Suzuki-Miyaura reactions involving alkyl trifluoroboronates. ArCl (0.5 mmol), R'R"CH—BF$_3$K (0.75 mmol), K$_2$CO$_3$ (1.5 mmol), 4d-P$^t$Bu$_3$ (1.0-2.0 mol %), Toluene (1.0 mL), H$_2$O (0.5 mL); isolated yields average of two runs.
Figure 14A:
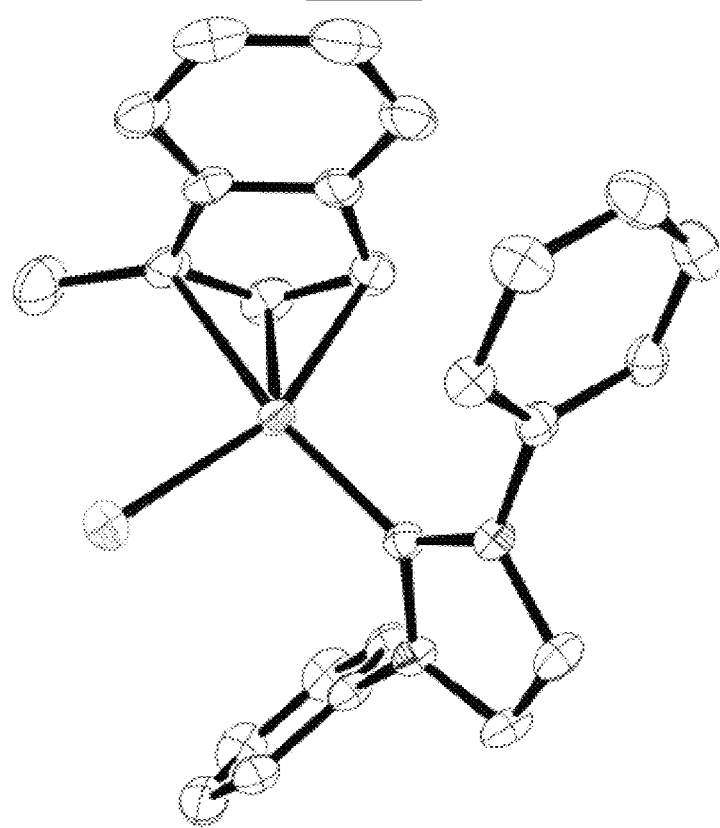
FIGS. 14A-14D comprise exemplary ORTEPs of 4b-IPr (FIG. 14A), 4c-IPr (FIG. 14B), 4d-IPr (FIG. 14C) and 4d-BrettPhos (FIG. 14D). Ellipsoids shown at 30% probability. $^i$Pr groups of IPr and hydrogen atoms are omitted for clarity.
Figure 14B:
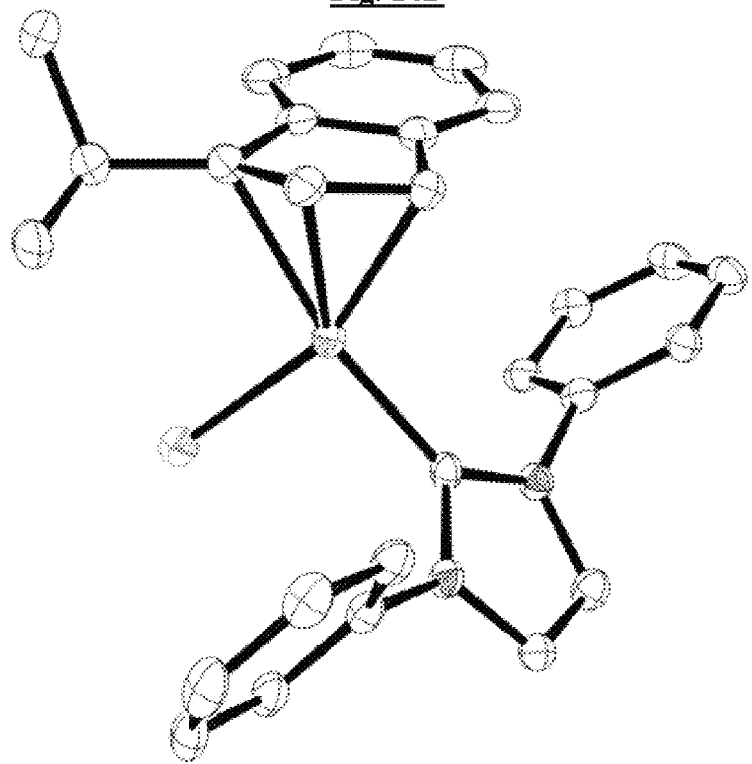
Figure 14C:
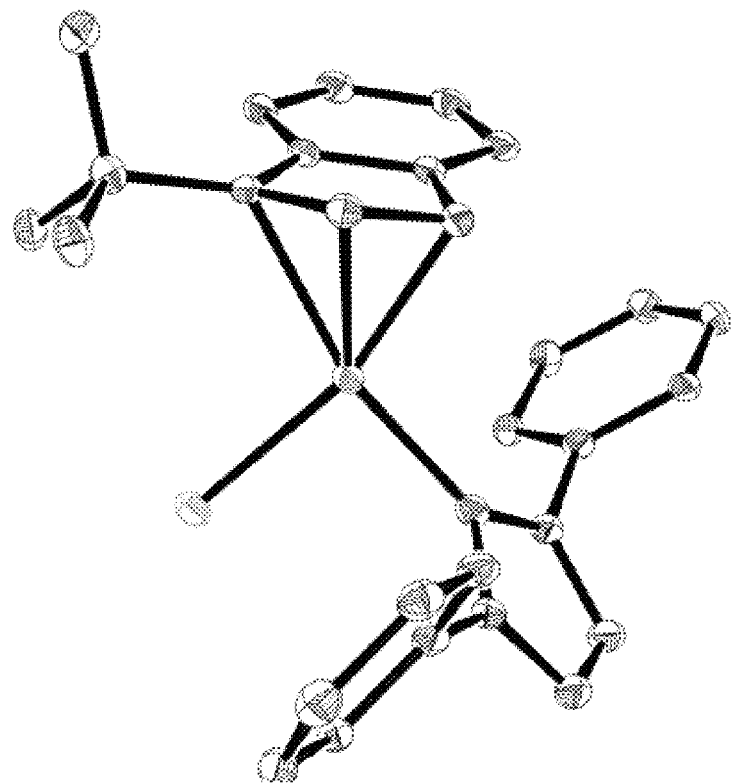
Figure 14D:
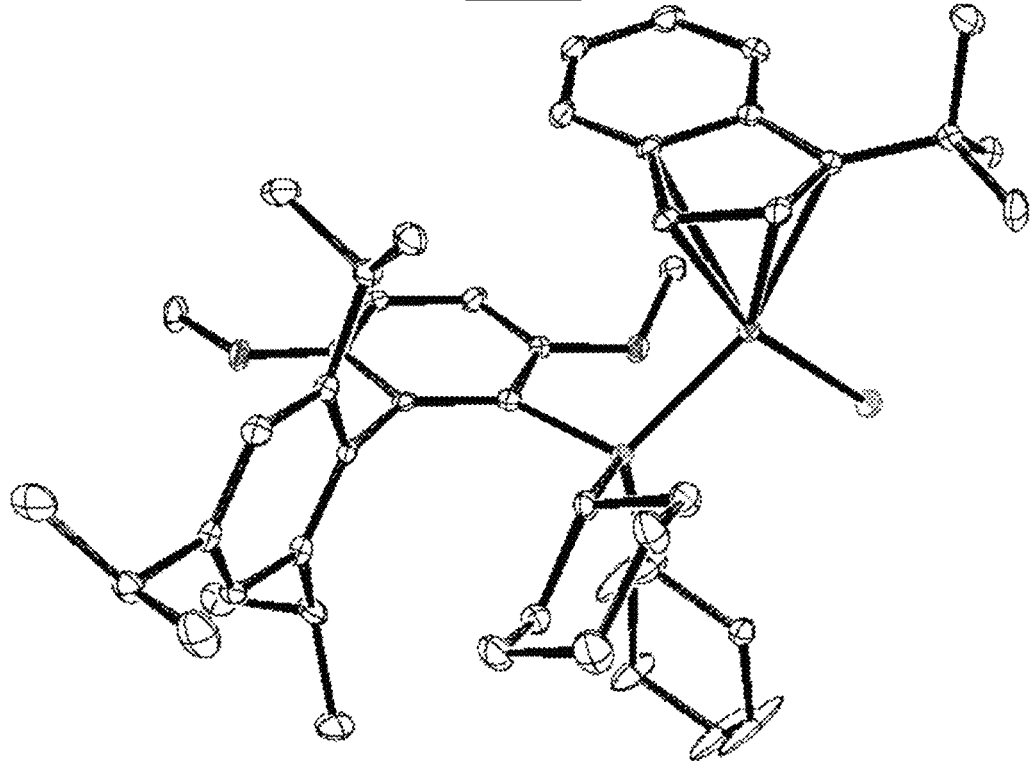

The precatalysts of the invention were used in cross-coupling of unactivated alkyl coupling partners. Using the literature systems, the Suzuki-Miyaura of alkyl trifluoroboronates (as boronic acid mimics) with aryl chlorides generally requires high catalyst loadings (5-10 mol %), high temperatures (110° C.) and long reaction times (24-48 hours). By using ($\mu^3$-1-$^t$Bu-indenyl)Pd(P$^t$Bu$_3$)(Cl) (4d-P$^t$Bu$_3$) as the precatalyst, sizable improvements on the existing protocol were achieved. Specifically, in some cases catalyst loadings could be reduced to 1 mol % and shorter reaction times (8 hours) utilized. By using 4d-P$^t$Bu$_3$, both linear and cyclic alkyl trifluoroboronates salts could be coupled to a variety of aryl chlorides, including one example of a nitrogen containing heterocycle (FIG. 13). In fact, when potassium cyclopropyl trifluoroboronate was used, the temperature could be lowered to 40° C. without any loss in activity (96% yield).

To demonstrate that ($\eta^3$-1-$^t$Bu-indenyl)$_2$($\mu$-Cl)$_2$Pd$_2$ (3d) is suitable for rapid ligand screening, without the need for the isolation of well-defined precatalysts, a series of catalytic reactions were performed using an in situ generated solution of 3d and two equivalents of ligand. When 3d was mixed with the appropriate ligand for 10 minutes at RT excellent activity was observed for all of the reactions described herein with isolated precatalysts. Comparative experiments between systems containing 3d and IPr and Nolan's cinnamyl dimer and IPr, showed that superior catalytic activity was observed with 3d. In fact, a successful reaction was achieved without premixing 3d and ligand; Eq 3 illustrates a one-pot Suzuki-Miyaura reaction where the precatalyst was generated during the reaction. Under these conditions, there was no loss in activity compared to both the in situ generated and isolated versions of 4d-XPhos. In certain embodiments, the present methodology allows access to a variety of general and rapid screening procedures.

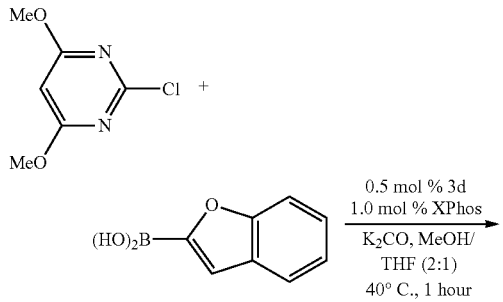

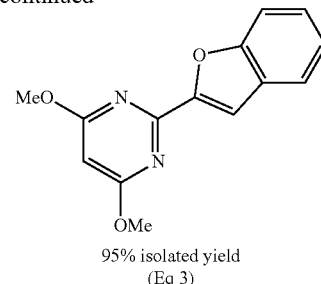

95% isolated yield
(Eq 3)

Precatalysts

In one aspect, the invention provides a precatalyst of formula (I), or a salt or solvate thereof:

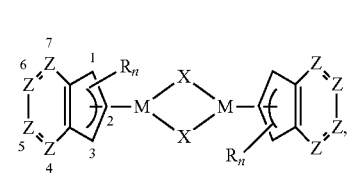

(I)

wherein in (I)
each occurrence of M is independently a transition metal; each occurrence of X is independently a ligand; each occurrence of R is independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, with the proviso that each of the 5-membered rings is substituted with at least one independently selected R; Z is CH, CR or N, with the proviso that 0-2 Z groups are N; or the Z groups at the 5- and 6-positions are null and the Z groups at the 4- and 7-positions are independently R; and n is 1, 2, 3, or 4.

In certain embodiments each occurrence of X is independently selected from the group consisting of halide, trifluoromethanesulfonate (triflate), tosylate, mesylate, tetrafluoroborate ($^-$BF$_4$), tetraphenylborate ($^-$BPh$_4$), hexafluorophosphate ($^-$PF$_6$), acetate, trifluoroacetate (TFA), acetonitrile, tetrahydrofuran (THF), dichloromethane (DCM) and water. In other embodiments, X is an anionic ligand. In yet other embodiments, X is a monocharged anionic ligand.

In certain embodiments, each occurrence of M is independently selected from the group consisting of Pd, Ni and Pt. In other embodiments, the two occurrences of M in (I) are identical. In yet other embodiments, the two occurrences of M in (I) are Pd. In yet other embodiments, the two occurrences of M in (I) are Ni. In yet other embodiments, the two occurrences of M in (I) are Pt.

In certain embodiments, the two occurrences of X in (I) are identical. In other embodiments, the two occurrences of X in (I) are chloride. In another embodiments, the two occurrences of X in (I) are bromide. In yet other embodiments, the two occurrences of X in (I) are fluoride. In yet other embodiments, the two occurrences of X in (I) are iodide. In yet other embodiments, the two occurrences of X in (I) are trifluoromethanesulfonate (triflate). In yet other embodiments, the two occurrences of X in (I) are mesylate.

In yet other embodiments, the two occurrences of X in (I) are tosylate. In yet other embodiments, the two occurrences of X in (I) are identical and selected from the group consisting of tetrafluoroborate (—BF$_4$), tetraphenylborate (—BPh$_4$), hexafluorophosphate (—PF$_6$), acetate, trifluoroacetate (TFA), acetonitrile, tetrahydrofuran (THF), dichloromethane (DCM) and water.

In certain embodiments, the two ligands comprising a 5-membered ring are identical. In other embodiments, the two ligands comprising a 5-membered ring are not identical.

In certain embodiments, each of the 5-membered rings is substituted with at least one R selected from the group consisting of an alkyl and substituted alkyl. In other embodiments, each of the 5-membered rings is substituted with at least one methyl group. In yet other embodiments, each of the 5-membered rings is substituted with at least one isopropyl group. In yet other embodiments, each of the 5-membered rings is substituted with at least one tert-butyl group.

In certain embodiments, the 1- or 3-position of each of the 5-membered rings is substituted with at least one R selected from the group consisting of alkyl and substituted alkyl. In other embodiments, the 1- or 3-position of each of the 5-membered rings is substituted with a methyl group. In yet other embodiments, the 1- or 3-position of each of the 5-membered rings is substituted with an isopropyl group. In yet other embodiments, the 1- or 3-position of each of the 5-membered rings is substituted with a tert-butyl group.

In certain embodiments, the 2-position of each of the 5-membered rings is substituted with at least one R selected from the group consisting of alkyl and substituted alkyl. In other embodiments, the 2-position of each of the 5-membered rings is substituted with a methyl group. In yet other embodiments, the 2-position of each of the 5-membered rings is substituted with an isopropyl group. In yet other embodiments, the 2-position of each of the 5-membered rings is substituted with a tert-butyl group.

In certain embodiments, each occurrence of Z is independently selected from the group consisting of CH and CR, so the precatalyst of formula (I) is a substituted indenyl complex.

In certain embodiments, n is 1. In other embodiments, n is 2. In yet other embodiments, n is 3. In yet other embodiments, n is 4.

In another aspect, the invention provides a precatalyst of formula (II), or a salt or solvate thereof:

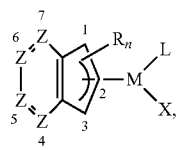

(II)

wherein in (II):
M is a transition metal; X is a ligand; each occurrence of R is independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, with the proviso that at least one R is a substituent in the 5-membered ring; Z is CH, CR or N, with the proviso that 0-2 Z groups are N; or the Z groups at the 5- and 6-positions are null and the Z groups at the 4- and 7-positions are independently R; L is a monodentate or bidentate ligand; and n is 1, 2, 3, or 4.

In certain embodiments, L is a bidentate ligand. In other embodiments, L is a bidentate ligand, and X coordinates to M. In yet other embodiments, L is a bidentate ligand and X is absent or does not coordinate to M (i.e., there is no coordination between X and M). In yet other embodiments, the two coordinating centers in the bidentate ligand L are coordinated with M.

In certain embodiments, each occurrence of X is independently a weakly coordinating ligand. In other embodiments, each occurrence of X is independently selected from the group consisting of halide, trifluoromethanesulfonate (triflate), tosylate, mesylate, tetrafluoroborate (—BF$_4$), tetraphenylborate (—BPh$_4$), hexafluorophosphate (—PF$_6$), acetate, trifluoroacetate (TFA), acetonitrile, tetrahydrofuran (THF), dichloromethane (DCM) and water.

In other embodiments, X is an anionic ligand. In yet other embodiments, X is a monocharged anionic ligand.

In certain embodiments, M is selected from the group consisting of Pd, Ni and Pt. In other embodiments, M is Pd. In yet other embodiments, M is Ni. In yet other embodiments, M is Pt.

In certain embodiments, X is chloride. In other embodiments, X is bromide. In yet other embodiments, X is fluoride. In yet other embodiments, X is iodide. In yet other embodiments, X is triflate. In yet other embodiments, X is mesylate. In yet other embodiments, X is tosylate.

In certain embodiments, L is at least one selected from the group consisting of a phosphine, a N-heterocyclic carbene, a N-containing ligand, an O-containing ligand, and a S-containing ligand.

In certain embodiments, L is selected from the group consisting of optionally substituted 1,3-dihydro-2H-imidazol-2-ylidene, optionally substituted 1,3,4,5-tetrahydro-2H-imidazol-2-ylidene, and optionally substituted 1,2,4-triazol-5-ylidene. In other embodiments, L is 1,3-bis(2,6-diisopropylphenyl)-1,3-dihydro-2H-imidazol-2-ylidene.

In certain embodiments, L is PR'R"R'", wherein R", R" and R'" are independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, wherein two or three R substituents may be optionally covalently linked to form a cyclic structure with P.

In certain embodiments, L is at least one selected from the group consisting of AmPhos (di-t-butylphosphino-4-dimethylaminobenzene), DavePhos (2-dicyclohexylphosphino-2'-(N,N-dimethylamino)biphenyl), $^{tBu}$DavePhos (2-Di-tert-butylphosphino-2'-(N,N-dimethylamino)biphenyl), QPhos (1,2,3,4,5-pentaphenyl-1'-(di-tert-butylphosphino)ferrocene), RuPhos (2-dicyclohexylphosphino-2',6'-diisopropoxybiphenyl), SPhos (2-dicyclohexylphosphino-2',6'-dimethoxybiphenyl), XPhos (2-dicyclohexylphosphino-2',4',6'-triisopropylbiphenyl), $^{tBu}$XPhos (2-Di-tert-butylphosphino-2',4',6'-triisopropylbiphenyl), $^{Me4tBu}$XPhos (2-Di-tert-butylphosphino-3,4,5,6-tetramethyl-2',4',6'-triisopropyl-1,1'-biphenyl), BrettPhos (2-(Dicyclohexylphosphino)3,6-dimethoxy-2',4',6'-triisopropyl-1,1'-biphenyl), $^{tBu}$BrettPhos (2-(Di-tert-butylphosphino)-2',4',6'-triisopropyl-3,6-dimethoxy-1,1'-biphenyl), $^{Ad}$BrettPhos (2-(Diadamantylphosphino)-2',4',6'-triisopropyl-3,6-dimethoxy-1,1'-biphenyl), Me-DalPhos (2-(Di-1- adamantylphosphino) phenylpiperidine), Mor-DalPhos (Di (1-adamantyl)-2-morpholinophenylphosphine), Di(1-adamantyl)-1-piperidinyl-phenylphosphine, triphenylphosphine, tri(o-tolyl) phosphine, tricyclohexylphosphine and tri(t-butyl)phosphine.

In certain embodiments, L is a bidentate phosphine ligand. In other embodiments, L is selected from the group consisting of 1,1'-bis(diphenylphosphino) ferrocene (DPPF), 4,5-bis(diphenylphosphino)-9,9-dimethylxanthene (XantPhos), 4,6-bis (diphenylphosphanyl)-10H-phenoxazine (NiXantPhos), 1,2-bis(diphenylphosphino)ethane (dppe), 1,1-bis(diphenylphosphino)methane (dppm), 1,3-bis(diphenylphosphino)propane (dppp), 1,4-bis(diphenylphosphino)butane (dppb), 2,2'-bis(diphenylphosphino)-1,1'-binaphthyl (BINAP), bis[(2-diphenylphosphino)phenyl] ether (DPEPhos), 1,2-bis(dichlorophosphino) ethane, and 1,2-bis(dicyclohexylphosphino)-ethane (dcpe).

In certain embodiments, L is NR'R"R'", wherein R", R" and R' are independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, wherein two or three R substituents may be optionally covalently linked to form a cyclic structure with N.

In certain embodiments, L is R'OR", wherein R" and R" are independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, wherein R' and R" may be optionally covalently linked to form a cyclic structure with O. In other embodiments, L is an optionally substituted furan or tetrahydrofuran. In yet other embodiments, L is an ester, ketone or aldehyde.

In certain embodiments, L is R'SR", wherein R" and R" are independently selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl, wherein R' and R" may be optionally covalently linked to form a cyclic structure with S. In other embodiments, L is an optionally substituted thiophene or tetrahydrothiophene. In yet other embodiments, L is an thioester, thioketone or thioaldehyde.

In certain embodiments, the 5-membered ring is substituted with at least one R selected from the group consisting of alkyl, substituted alkyl, cycloalkyl, substituted cycloalkyl, alkenyl, substituted alkenyl, alkynyl, substituted alkynyl, phenyl, substituted phenyl, phenylalkyl, substituted phenylalkyl, aryl, substituted aryl, arylalkyl, substituted arylalkyl, heteroarylalkyl, substituted heteroarylalkyl, heteroaryl and substituted heteroaryl. In other embodiments, the 5-membered ring is substituted with at least one R selected from the group consisting of an alkyl and substituted alkyl. In yet other embodiments, the 5-membered ring is substituted with at least one methyl group. In yet other embodiments, the 5-membered ring is substituted with at least one isopropyl group. In yet other embodiments, the 5-membered ring is substituted with at least one tert-butyl group.

In certain embodiments, the 1- or 3-position of the 5-membered ring is substituted with at least one R selected from the group consisting of alkyl and substituted alkyl. In other embodiments, the 1- or 3-position of the 5-membered ring is substituted with a methyl group. In yet other embodiments, the 1- or 3-position of the 5-membered ring is substituted with an isopropyl group. In yet other embodiments, the 1- or 3-position of the 5-membered ring is substituted with a tert-butyl group.

In certain embodiments, the 2-position of the 5-membered ring is substituted with at least one R selected from the group consisting of alkyl and substituted alkyl. In other embodiments, the 2-position of the 5-membered ring is substituted with a methyl group. In yet other embodiments, the 2-position of the 5-membered ring is substituted with an isopropyl group. In yet other embodiments, the 2-position of the 5-membered ring is substituted with a tert-butyl group.

In certain embodiments, each occurrence of Z is independently selected from the group consisting of CH and CR, so the precatalyst of formula (II) is a substituted indenyl complex.

In certain embodiments, n is 1. In other embodiments, n is 2. In yet other embodiments, n is 3. In yet other embodiments, n is 4.

One of ordinary skill in the art will contemplate from formula (I) and formula (II) that a R can be a substituent on the six-membered ring and/or the five-membered ring, at any proper position. For example, when the coordination ligand is indene, as depicted in formula (III), a R can be a substituent on positions 1, 2, 3, 4, 5, 6, and/or 7. In certain embodiments, a R is attached to the 1- or 3-position of the five-membered ring. In other embodiments, a R is attached to the 2-position of the five-membered ring.

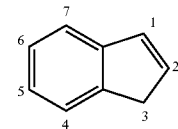

(III)

The precatalysts of the invention may possess one or more stereocenters, and each stereocenter may exist independently in either the (R) or (S) configuration. In certain embodiments, precatalysts described herein are present in optically active or racemic forms. The precatalysts described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase.

In certain embodiments, the precatalysts of the invention exist as tautomers. All tautomers are included within the scope of the precatalysts recited herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, substitution with heavier isotopes such as deuterium affords greater chemical stability. Isotopically-labeled compounds are prepared by any suitable method or by processes using an appropriate isotopically-labeled reagent in place of the non-labeled reagent otherwise employed.

In certain embodiments, the precatalysts described herein are labeled by other means, including, but not limited to, the use of chromophores or fluorescent moieties, bioluminescent labels, or chemiluminescent labels.

Synthesis

The precatalysts described herein, and other related precatalysts having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure).

Precatalysts described herein are synthesized using any suitable procedures starting from compounds that are available from commercial sources, or are prepared using procedures described herein. Modifications of these procedures are known to those skilled in the art. The scheme included herein are intended to illustrate but not limit the chemistry and methodologies that one skilled in the art may use to make precatalysts of the invention.

In certain embodiments, the synthesis of the precatalyst of formula (I) is conducted in one step and can be performed under aerobic conditions, without the use of air sensitive reagents.

In certain embodiments, a transition metal salt (such as, but not limited to, a halide, triflate, mesylate or tosylate is reacted with an alkaline or alkaline-earth salt to yield a mixed salt, such as but not limited to Na$_2$PdCl$_4$. The mixed salt may be reacted with a substituted indene and a base (such as, but not limited to, cesium, potassium or sodium carbonate in an organic solvent (such as, but not limited to, methanol, ethanol, isopropanol, tetrahydrofuran, and/or 1,4-dioxane. The mixture is stirred at a temperature ranging from about −20° C. to about 80° C. In certain embodiments, the precatalyst precipitates out of solution, and is isolated and optionally purified by washing, recrystallization and/or extraction. In other embodiments, the precatalyst is isolated from solution using a method such as chromatography, precipitation, crystallization and/or extraction.

In certain embodiments, the synthesis of the precatalyst of formula (II) comprises reacting a precatalyst of formula (I) with an appropriate ligand L, such as but not limited to IPr (1,3-bis(2,6-diisopropylphenyl)-1,3-dihydro-2H-imidazol-2-ylidene), in an organic solvent such as, but not limited to, diethyl ether, tetrahydrofuran, and/or 1,4-dioxane.

Methods

The precatalyst of formula (I) or formula (II) can be used in coupling reactions to promote formation of a carbon-carbon, carbon-oxygen, carbon-nitrogen, and/or carbon-sulfur bond(s). In certain embodiments, the precatalyst of formula (I) or formula (II) can be used to promote the reactions depicted in FIG. 2.

In certain embodiments, the precatalyst of formula (I) or formula (II) is used to promote the coupling of an aromatic or heteroaromatic boronic acid or ester with an aromatic or heteroaromatic halide, tosylate, triflate, mesylate, sulfamate or carbamate (Suzuki-Miyaura reaction).

In certain embodiments, the precatalyst of formula (I) or formula (II) is used to promote the coupling of an aromatic or heteroaromatic amine with an aromatic, heteroaromatic or vinylic halide, tosylate, triflate, mesylate, sulfamate or carbamate (Buchwald-Hartwig reaction).

In certain embodiments, the precatalyst of formula (I) or formula (II) is used to promote the coupling of an aromatic or heteroaromatic zinc halide with an aromatic, heteroaromatic or vinylic halide, tosylate, triflate, mesylate, sulfamate or carbamate (Negishi reaction).

In certain embodiments, the precatalyst of formula (I) or formula (II) is used to promote the coupling of an aromatic or heteroaromatic magnesium halide with an aromatic, heteroaromatic or vinylic halide, tosylate, triflate, mesylate, sulfamate or carbamate (Kumada reaction).

In certain embodiments, the precatalyst of formula (I) or formula (II) is used to promote the coupling of an aromatic or heteroaromatic tin halide with an aromatic, heteroaromatic or vinylic halide, tosylate, triflate, mesylate, sulfamate or carbamate (Stille reaction).

In certain embodiments, the precatalyst of formula (I) or formula (II) is used to promote the α-arylation of a ketone, aldehyde, imine, amide or ester with an aromatic, heteroaromatic or vinylic halide, tosylate, triflate, mesylate, sulfamate or carbamate (α-arylation reaction).

In certain embodiments, the precatalyst of formula (I) or formula (II) is used to promote the reaction of an alcohol or thiol with an aromatic, heteroaromatic or vinylic halide, tosylate, triflate, mesylate, sulfamate or carbamate (C—S or C—O bond formation).

In certain embodiments, the precatalyst of formula (I) or formula (II) is used to promote the reaction of an aromatic or heteroaromatic silanol, siloxane or silane with an aromatic, heteroaromatic or vinylic halide, tosylate, triflate or mesylate (Hiyama coupling).

In certain embodiments, the precatalyst of formula (I) or formula (II) is used to promote the anaerobic oxidation of a primary or secondary alcohol.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so on, as well as individual numbers within that range, for example, 1, 2, 2.7, 3, 4, 5, 5.3, and 6. This applies regardless of the breadth of the range.

The following examples further illustrate aspects of the present invention.

However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods:
Materials:

Unless otherwise noted, all starting materials were obtained from commercial suppliers and used without purification.

Pentane, THF, diethyl ether and toluene were dried by passage through a column of activated alumina followed by storage under dinitrogen. All commercial chemicals were used as received except where noted. MeOH (J. T. Baker), $^i$PrOH (Macron Fine Chemicals), and 200 proof EtOH (Decon Laboratories Inc.) were not dried, but were degassed by sparging with dinitrogen for 1 hour and stored under dinitrogen. Ethyl acetate (Fisher Scientific) and hexanes (Macron Fine Chemicals) were used as received. Potassium tert-butoxide (99.99%, sublimed), naphthalene (99%), 4-chlorotoluene (98%) and 4-chloroanisole (99%) were purchased from Aldrich. 2,6-dimethylboronic acid (98%), 1-naphthaleneboronic acid (97%), 1-chloronaphthalene (90+%) and 2-methoxyboronic acid (97%) were purchased from Fisher Scientific. Potassium carbonate was purchased from Mallinckrodt. 1,3-divinyltetramethyldisiloxane and 4-methylbiphenyl were purchased from TCI. Phenylboronic acid (98%) and 2,4,6-trimethylbenzeneboronic acid (97%) were purchased from Alfa Aesar. Potassium carbonate was ground up with a mortar and pestle and stored in an oven at 130° C. prior to use. 4-chlorotoluene, 2-chloro-m-xylene, 1-chloronaphthalene, 4-chloroanisole and 1,3-divinyltetramethyldisiloxane were degassed prior to use through three freeze-pump-thaw cycles.

Deuterated solvents were obtained from Cambridge Isotope Laboratories. $C_6D_6$ was dried over sodium metal and stored under nitrogen, while $d_4$-MeOH, $d_8$-PrOH, and $d_8$-THF were not dried but were degassed prior to use through three freeze-pump-thaw cycles.

Literature procedures were used to prepare the following compounds: IPr (Arduengo, et al., 1999, Tetrahedron 55:14523; Tang, et al., 2011, J. Am. Chem. Soc. 133:11482), ($\eta^3$-allyl)Pd(IPr)(Cl) (1-IPr) (Viciu, et al., 2002, Org. Lett. 4:4053) and ($\eta^3$-cinnamyl)Pd(IPr)(Cl) (2-IPr) (Marion, et al., 2006, J. Am. Chem. Soc. 128:4101).

Methods:

Experiments were performed under a dinitrogen atmosphere in an M-Braun dry box or using standard Schlenk techniques unless otherwise stated. Under standard glovebox conditions purging was not performed between uses of pentane, benzene and toluene; thus when any of these solvents were used, traces of all these solvents were in the atmosphere and could be found intermixed in the solvent bottles. Moisture- and air-sensitive liquids were transferred by stainless steel cannula on a Schlenk line or in a dry box.

Flash chromatography was performed on silica gel 60 (230-400 mesh, Fisher Scientific).

NMR spectra were recorded on Agilent-400, -500 and -600 spectrometers and Varian-300, -500 spectrometers at ambient probe temperatures unless noted. For variable temperature NMR, the sample temperature was calibrated by measuring the distance between the OH and $CH_2$ resonances in ethylene glycol (99%, Aldrich). Chemical shifts are reported with respect to residual internal protio solvent for $^1H$ and $^{13}C\{^1H\}$ NMR spectra.

Gas chromatography analyses (GC) were performed on a Shimadzu GC-2010 Plus apparatus equipped with a flame ionization detector and a Shimadzu SHRXI-5MS column (30 m, 250 µm inner diameter, film: 0.25 µm). The following conditions were utilized for GC analyses: flow rate 1.23 mL/min constant flow, column temperature 50° C. (held for 5 min), 20° C./min increase to 300° C. (held for 5 min), total time 22.5 min.

High resolution mass spectrometry was performed using an ion-cyclotron resonance (ICR) mass spectrometer equipped with a superconducting (7 T) magnet.

X-Ray Crystallography:

X-ray diffraction experiments were carried out on either a Rigaku Mercury 275R CCD (SCX mini) diffractometer using graphite-monochromated Mo Kα radiation ($\lambda$=0.71073 Å) at −50° C. or a Rigaku MicroMax-007HF diffractometer coupled to a Saturn994+ CCD detector with Cu Kα radiation ($\lambda$=1.54178 Å) at −180° C. The crystals were mounted on MiTeGen polyimide loops with immersion oil. The data frames were processed using Rigaku CrystalClear and corrected for Lorentz and polarization effects. Using Olex2, the structure was solved with the XS structure solution program using direct methods and refined with the XL refinement package using least squares minimisation. The non-hydrogen atoms were refined anisotropically. Hydrogen atoms were refined using the riding model.

Example 1: Synthesis and Characterization

Synthetic Procedures for 1-Substituted Indenes:
1-Methylindene:

Lithium indenyl (1.00 g, 8.25 mmol) was added to a 100 mL Schlenk flask in a glovebox and dissolved in 50 mL of diethyl ether. Methyl iodide (0.62 mL, 9.9 mmol) was added to the Schlenk flask via syringe. The reaction mixture was stirred for two hours at room temperature. After this time, the mixture was poured into a separatory funnel and washed three times with water. The organic layer was dried over $MgSO_4$, filtered, and the volatiles removed under reduced pressure to yield the product as a pale yellow oil. Yield: 0.70 g, 65%. $^1H$ NMR data was consistent with that previously reported in Villasenor, et al., 2013, Eur. J. Inorg. Chem. 2013:1184-1196.

1-Iso-Propylindene:

This compound was synthesized using the procedure reported by Someya, et al., 2010, Tetrahedron 66:5993-5999.

1-Tert-Butylindene:

Lithium indenyl (20.0 g, 0.164 mol) was added to a 500 mL Schlenk flask in a glovebox and 200 mL of diethyl ether was added to dissolve the complex. Silver bromide (0.3 g, 1.59 mmol) was added to the solution; the flask was removed from the glovebox and stirred in a −78° C. bath.

Upon cooling, a yellow precipitate appeared (lithium indenyl is not soluble in diethyl ether at this temperature). 2-bromo-2-methylpropane (22.1 mL, 0.18 mol) was added slowly via syringe. The reaction mixture was warmed to room temperature and stirred for 12 hours. A homogenous solution resulted upon warming to room temperature. After this time, the flask was opened to air and the product was extracted into 300 mL of ethyl acetate and washed with an aqueous solution of ammonium chloride. The aqueous layer was extracted twice (2×200 mL) with ethyl acetate. The organic layers were combined, dried over $MgSO_4$, filtered and the volatiles were removed. The resulting oil was dissolved in hexanes and passed through a pad of silica gel. The solvent was removed via rotary evaporator to yield a yellow oil. Yield: 22.7 g, 80%. $^1$H NMR data was consistent with that previously reported in Someya, et al., 2010, Tetrahedron 66:5993-5999.

Synthetic Procedures for Complexes:

($\eta^3$-Indenyl)$_2$($\mu$-Cl)$_2$Pd$_2$ (3a):

$PdCl_2$ (1.00 g, 5.64 mmol) and NaCl (0.658 g, 11.3 mmol) were added to a 250 mL round bottom flask. MeOH (70 mL) was added and the reaction mixture heated at 50° C. for 30 minutes, at which time it became homogeneous. The solution was allowed to cool to room temperature. Indene (0.650 g, 5.64 mmol) was added, followed by $Na_2CO_3$ (0.888 g, 8.46 mmol) and the reaction stirred for 2 hours at room temperature. The reaction mixture was filtered and the resulting brown solid washed with water and diethyl ether. The product was dried under vacuum to yield 3a as a brown solid. Yield: 1.22 g, 84%. The $^1$H NMR data was consistent with that published in the literature (Sui-Seng, et al., 2004, Organomet. 23:1236)

($\eta^3$-1-Me-Indenyl)$_2$($\mu$-Cl)$_2$Pd$_2$ (3b):

$PdCl_2$ (0.885 g, 5.0 mmol) and NaCl (0.585 g, 10.0 mmol) were added to a 100 mL round bottom flask. MeOH (50 mL) was added and the reaction mixture heated at 50° C. for 30 minutes, at which time it became homogeneous. The solution was allowed to cool to room temperature. 1-Methyl-indene (0.650 g, 5.00 mmol) was added, followed by $Na_2CO_3$ (1.06 g, 10.0 mmol) and the reaction stirred for 2 hours at room temperature. The reaction mixture was filtered and the resulting brown solid washed with water and diethyl ether. The product was dried under vacuum to yield 3b as a brown solid. Yield: 1.20 g, 89%.

$^1$H NMR (CDCl$_3$, 600 MHz): 6.77-6.85 (m, C$_6$H$_4$, 8H), 6.64 (br, MeC$_5$H$_2$, 2H), 5.66 (br, MeC$_5$H$_2$, 2H), 1.16 (s, Me-Ind, 6H). $^{13}$C{$^1$H} NMR (CDCl$_3$, 150 MHz): 141.9, 140.7, 128.2, 127.7, 118.3, 117.1, 110.0, 96.2, 74.8, 13.5.

($\eta^3$-1-$^i$Pr-Indenyl)$_2$($\mu$-Cl)$_2$Pd$_2$ (3c):

$PdCl_2$ (0.337 g, 1.89 mmol) and NaCl (0.220 g, 3.78 mmol) were added to a 100 mL round bottom flask. MeOH (30 mL) was added and the reaction mixture heated at 50° C. for 30 minutes, at which time it became homogeneous. The solution was allowed to cool to room temperature. 1-Isopropyl-indene (0.300 g, 1.89 mmol) was added, followed by $Na_2CO_3$ (0.300 g, 2.84 mmol) and the reaction was for 2 hours at room temperature. The reaction mixture was filtered and the resulting brown solid washed with water and diethyl ether. The product was dried under vacuum to yield 3c as a brown solid. Yield: 0.400 g, 71%.

$^1$H NMR (CDCl$_3$, 600 MHz): 6.75-6.90 (m, C$_6$H$_4$, 8H), 6.58 (br, $^i$PrC$_5$H$_2$, 2H), 5.64 (br, $^i$PrC$_5$H$_2$, 2H), 2.11 (sept, J=6.7 Hz, (CH$_3$)$_2$CH, 2H), 1.21 (d, J=6.9 Hz, (CH$_3$)$_2$CH, 6H), 1.18 (d, J=6.9 Hz, (CH$_3$)$_2$CH, 6H). $^{13}$C{$^1$H} NMR (CDCl$_3$, 150 MHz): 140.9, 140.7, 128.0, 127.6, 118.5, 117.7, 117.6, 105.6, 75.2, 27.0, 20.6, 20.3.

($\eta^3$-1-$^t$Bu-Indenyl)$_2$($\mu$-Cl)$_2$Pd$_2$ (3d):

$PdCl_2$ (0.412 g, 2.32 mmol) and NaCl (0.269 g, 4.64 mmol) were added to a 100 mL round bottom flask. MeOH (40 mL) was added and the reaction mixture heated at 50° C. for 30 minutes, at which time it became homogeneous. The solution was allowed to cool to room temperature. 1-t-Butyl-indene (0.400 g, 2.32 mmol) was added, followed by $Na_2CO_3$ (0.369 g, 3.48 mmol) and the reaction stirred for 2 hours at room temperature. The reaction mixture was filtered and the resulting brown solid washed with water and diethyl ether. The product was dried under vacuum to yield 3d as a brown solid. Yield: 0.550 g, 77%.

$^1$H NMR (CDCl$_3$, 600 MHz): 7.11 (br, $^t$BuC$_5$H$_2$, 2H), 6.65-6.80 (m, C$_6$H$_4$, 8H), 5.50 (d, J=2.7 Hz, $^t$BuC$_5$H$_2$, 2H), 1.29 (s, (CH$_3$)$_3$C, 18H). $^{13}$C{$^1$H} NMR (CDCl$_3$, 150 MHz): 142.1, 140.9, 127.7, 127.4, 120.3, 120.2, 118.9, 118.8, 107.7, 107.6, 73.4, 34.4, 28.9.

($\eta^3$-Indenyl)Pd(IPr)(Cl) (4a-IPr):

($\eta^3$-indenyl)$_2$($\mu$-Cl)$_2$Pd$_2$ (3a) (0.600 g, 1.17 mmol) and IPr (0.900 g, 2.34 mmol) were added to a 100 mL Schlenk flask. Diethyl ether (40 mL) was added to the flask via cannula. The resulting solution was stirred for 90 minutes, during which time the reaction mixture became homogeneous. The solution was passed through a pad of silica gel, followed by the removal of solvent using a rotary evaporator to give 4a-IPr as an orange powder. Yield: 1.33 g, 88%. The $^1$H NMR data was consistent with that published in the literature (Bielinski, et al., 2013, Organomet. 32:4025).

($\eta^3$-1-Me-Indenyl)Pd(IPr)(Cl) (4b-IPr):

($\eta^3$-1-Me-indenyl)$_2$($\mu$-Cl)$_2$Pd$_2$ (3b) (0.300 g, 0.502 mmol) and IPr (0.390 g, 1.00 mmol) were added to a 100 mL Schlenk flask. Diethyl ether (30 mL) was added to the flask via cannula. The resulting solution was stirred for 90 minutes, during which time the reaction mixture became homogeneous. The solution was passed through a pad of silica gel, followed by the removal of solvent using a rotary evaporator to give 4b-IPr as an orange powder. Yield: 0.550 g, 81%. X-ray quality crystals were grown by slow evaporation from a saturated pentane solution.

$^1$H NMR (C$_6$D$_6$, 600 MHz): 7.22 (t J=7.6 Hz, 2H, para-H Ar$_{IPr}$), 7.11 (d, J=6.5 Hz, 2H, meta-H Ar$_{IPr}$), 7.07 (d, J=7.3 Hz, 2H, meta-H Ar$_{IPr}$), 6.81 (t, J=8.0 Hz, 1H, Ind), 6.77 (t, J=7.7 Hz, 1H, Ind), 6.41 (t, J=8.1 Hz, 1H, Ind), 6.03 (br, 1H, Ind) 5.87 (d, J=7.1 Hz, 1H, Ind), 5.21 (br, 1H, Ind), 3.39 (sept, J=6.8 Hz, 2H, (CH$_3$)$_2$CH), 2.83 (sept, J=6.8 Hz, 2H, (CH$_3$)$_2$CH), 1.58 (s, 3H, CH$_3$—Ind), 1.48 (d, J=6.6 Hz, 6H, (CH$_3$)$_2$CH), 1.19 (d, J=6.6 Hz, 6H, (CH$_3$)$_2$CH), 1.06 (d, J=6.7 Hz, 6H, (CH$_3$)$_2$CH), 0.93 (d, J=6.7 Hz, 6H, (CH$_3$)$_2$CH). $^{13}$C{$^1$H}NMR (C$_6$D$_6$, 150 MHz): 179.9, 146.6, 140.0, 138.4, 137.1, 130.5, 125.5, 124.9, 124.8, 124.6, 117.0, 116.1, 110.1, 101.0, 66.1, 29.1, 29.0, 26.7, 26.0, 24.1, 22.9, 12.4. Anal. Calcd for C$_{37}$H$_{45}$ClN$_2$Pd: C, 67.37; H, 6.88; N, 4.25. Found: C, 67.15; H, 7.00; N, 4.27.

($\eta^3$-1-$^i$Pr-Indenyl)Pd(IPr)(Cl) (4c-IPr):

($\eta^3$-1-$^i$Pr-indenyl)$_2$($\mu$-Cl)$_2$Pd$_2$ (3c) (0.300 g, 0.502 mmol) and IPr (0.390 g, 1.00 mmol) were added to a 100 mL Schlenk flask. Diethyl ether (30 mL) was added to the flask via cannula. The resulting solution was stirred for 90 minutes, during which time the reaction mixture became homogeneous. The solution was passed through a pad of silica gel, followed by the removal of solvent using a rotary evaporator to give 4c-IPr as an orange powder. Yield: 0.550 g, 81%. X-ray quality crystals were grown by slow evaporation from a saturated pentane solution.

$^1$H NMR (C$_6$D$_6$, 600 MHz): 7.25 (t, J=7.7 Hz, 2H, para-H Ar$_{IPr}$), 7.15 (obscured by solvent, 2H, meta-H Arrpr), 7.09 (dd, J=1.4, 6.3 Hz, 2H, meta-H Ar$_{IPr}$), 6.89 (d, J=7.4 Hz, 1H, Ind), 6.83 (t, J=8.4 Hz, 1H, Ind), 6.55 (s, 2H, HCCH), 6.42

(t, J=7.4 Hz, 1H, Ind), 6.05 (d, J=2.7 Hz, 1H, Ind), 5.89 (d, J=7.4 Hz, 1H, Ind), 5.29 (d, J=2.8 Hz, 1H, Ind) 3.36 (sept, J=6.8 Hz, 2H, $(CH_3)_2CH$), 2.86 (sept, J=6.8 Hz, 1H, $(CH_3)_2CH$-Ind), 2.82 (sept, J=6.8 Hz, 2H, $(CH_3)_2CH$), 1.48 (d, J=6.7 Hz, 2H, $(CH_3)_2CH$), 1.19 (d, J=6.9 Hz, 6H, $(CH_3)_2CH$), 1.18 (d, J=5.2 Hz, 3H, $(CH_3)_2CH$-Ind), 1.16 (d, J=4.5 Hz, 3H, $(CH_3)_2CH$-Ind), 1.06 (d, J=6.8 Hz, 6H, $(CH_3)_2CH$), 0.93 (d, J=6.8 Hz, 6H, $(CH_3)_2CH$). $^{13}C\{^1H\}$ NMR ($C_6D_6$, 150 MHz): 179.6, 146.8, 146.7, 138.1, 137.2, 137.0, 130.3, 125.1, 125.0, 124.8, 124.6, 124.5, 117.4, 116.5, 110.5, 105.2, 67.4, 29.2, 29.1, 26.8, 26.0, 24.1, 22.9, 22.1, 21.0. Anal. Calcd for $C_{39}H_{49}ClN_2Pd$: C, 68.11; H, 7.18; N, 4.07. Found: C, 67.89; H, 7.42; N, 4.04.

($\eta^3$-1-$^t$Bu-Indenyl)Pd(IPr)(Cl) (4d-IPr):

($\eta^3$-1-$^t$Bu-indenyl)$_2(\mu$-Cl)$_2$Pd$_2$ (3d) (0.400 g, 0.65 mmol) and IPr (0.505 g, 1.30 mmol) were added to a 100 mL Schlenk flask. Diethyl ether (40 mL) was added to the flask via cannula. The resulting solution was stirred for 90 minutes, during which time the reaction mixture became homogeneous. The solution was passed through a pad of silica gel, followed by the removal of solvent using a rotary evaporator to give 4d-IPr as an orange powder. Yield: 0.705 g, 78%. X-ray quality crystals were grown by slow evaporation from a saturated pentane solution.

$^1$H NMR ($C_6D_6$, 600 MHz): 7.27 (d, J=6.9 Hz, 1H, Ind), 7.26 (t, J=7.4 Hz, 2H, para-H Ar$_{IPr}$), 7.15 (obscured by solvent, 2H, meta-H Ar$_{IPr}$) 7.09 (d, J=7.6 Hz, 2H, meta-H Ar$_{IPr}$), 6.83 (t, J=7.5 Hz, 1H, Ind), 6.54 (s, 2H, HCCH), 6.44 (t, J=7.5 Hz, 1H, Ind), 6.19 (d, J=2.9 Hz, 1H, Ind), 5.83 (d, J=7.4 Hz, 1H, Ind), 5.12 (d, J=2.9 Hz, 1H, Ind), 3.42 (sept, J=6.7 Hz, 2H, $(CH_3)_2CH$), 2.83 (sept, J=6.7 Hz, 2H, $(CH_3)_2CH$), 1.47 (d, J=6.7 Hz, 6H, $(CH_3)_2CH$), 1.45 (s, 9H, $(CH_3)_3C$), 1.18 (d, J=6.7 Hz, 6H, $(CH_3)_2CH$), 1.05 (d, J=6.7 Hz, 6H, $(CH_3)_2CH$), 0.92 (d, J=6.7 Hz, 6H, $(CH_3)_2CH$). $^{13}C\{^1H\}$ NMR ($C_6D_6$, 150 MHz): 178.5, 146.8, 146.7, 139.5, 139.0, 137.1, 130.3, 124.9, 124.8, 124.7, 124.5, 119.7, 117.2, 115.9, 107.5, 64.3, 34.6, 30.2, 29.2, 29.1, 26.9, 26.0, 24.1, 22.9, 1.8.

($\mu$-Indenyl)($\mu$-Cl)Pd$_2$(IPr)$_2$ (7-IPr):

($\eta^3$-indenyl)Pd(IPr)(Cl) (4a-IPr) (0.200 g, 0.31 mmol) and K$_2$CO$_3$ (0.086 g, 0.62 mmol) were added to a 100 mL Schlenk flask. Degassed MeOH (30 mL) was added to the flask via cannula. The reaction mixture was stirred at room temperature for 2 hours. The precipitate was filtered in air and washed with water to remove excess salts. The solid was washed with pentane and dried under vacuum to give 7-IPr as a dark yellow solid. Yield: 0.150 g, 85%. X-ray quality crystals were grown from a saturated toluene solution layered with pentane (V(toluene):V(pentane)=1:2) at −35° C.

$^1$H NMR ($C_6D_6$, 400 MHz): 7.25 (t, J=7.7 Hz, 4H, para-H Ar$_{IPr}$), 7.08-7.14 (m, 8H, meta-H Ar$_{IPr}$), 6.71 (dd, J=2.2 Hz, 2H, Ind), 6.64 (s, 4H, HCCH), 6.37 (dd, J=2.1 Hz, 2H, Ind), 4.87 (d, J=3.9 Hz, 2H, Ind), 3.18 (sept, J=6.9 Hz, 4H, $(CH_3)_2CH$), 3.11 (sept, J=6.9 Hz, 4H, $(CH_3)_2CH$), 3.00 (t, J=3.9 Hz, 1H, Ind) 1.33 (d, J=6.8 Hz, 12H, $(CH_3)_2CH$) 1.14 (d, J=5.8 Hz, 12H, $(CH_3)_2CH$) 1.11 (d, J=6.6 Hz, 12H, $(CH_3)_2CH$) 1.09 (d, J=6.9 Hz, 12H, $(CH_3)_2CH$). $^{13}C\{^1H\}$ NMR ($C_6D_6$, 100 MHz): 188.8, 147.2, 146.8, 146.3, 137.8, 129.7, 124.5, 124.3, 123.4, 122.5, 121.9, 68.6, 45.5, 29.2, 29.1, 26.4, 25.9, 24.0, 23.9. Anal. Calcd for $C_{63}H_{79}ClN_4Pd_2$: C, 66.34; H, 6.98; N, 4.91. Found: C, 66.59; H, 7.03; N, 4.82.

($\eta^3$-1-$^t$Bu-Indenyl)Pd(IPr*$^{OMe}$)(Cl) (4d-IPr*$^{OMe}$):

($\eta^3$-1-$^t$Bu-indenyl)$_2(\mu$-Cl)$_2$Pd$_2$ (3d) (0.165 g, 0.265 mmol) and IPr*$^{OMe}$ (0.500 g, 0.53 mmol) were added to a 100 mL Schlenk flask and placed under an atmosphere of nitrogen. THF (30 mL) was added to the flask via cannula. The resulting solution was stirred for 24 hours, during which time the reaction mixture became homogeneous. The reaction mixture was passed through a pad of silica gel with celite on top. Approximately 90% of the solvent was evaporated under reduced pressure. Pentane was added to precipitate solid from solution. A beige solid was collected via vacuum filtration. Yield: 0.534 g, 80%.

$^1$H NMR ($C_6D_6$, 600 MHz): 7.65 (d, J=5.75 Hz, 4H), 7.47 (d, J=7.67 Hz, 1H), 7.32 (d, J=7.47 Hz, 4H), 7.22 (t, J=7.57 Hz, 4H), 7.13 (t, J=7.44 Hz, 3H), 7.03-6.98 (m, 6H), 6.94 (d, J=2.70 Hz, 2H), 6.91-6.82 (m, 14H), 6.78-6.75 (m, 2H), 6.69 (s, 2H), 6.66-6.63 (m, 3H), 6.20 (t, J=7.46 Hz, 1H), 6.00 (s, 2H), 5.88 (d, J=7.40 Hz, 1H), 5.47 (d, J=2.19 Hz, 1H), 5.13 (s, 2H), 3.15 (s, 6H), 1.65 (s, 9H) ppm. $^{13}C\{^1H\}$ NMR ($C_6D_6$ 150 MHz): 159.93, 144.94, 144.39, 131.34, 131.20, 130.08, 129.88, 128.68, 128.50, 128.30, 128.11, 127.13, 126.89, 126.85, 124.45, 115.74, 115.36, 109.06, 54.69, 52.13, 34.85, 29.96 ppm.

($\eta^3$-1-$^t$Bu-Indenyl)Pd(XPhos)(Cl) (4d-XPhos):

($\eta^3$-1-$^t$Bu-indenyl)$_2(\mu$-Cl)$_2$Pd$_2$ (3d) (0.300 g, 0.48 mmol) and XPhos (0.460 g, 0.98 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.650 g, 86%.

$^1$H NMR (CDCl$_3$, 600 MHz): 7.98-7.93 (m, 1H), 7.46 (d, J=7.6 Hz, 1H), 7.34 (m, 2H), 7.06-7.02 (m, 4H), 6.89-6.83 (m, 2H), 6.42 (s, 1H), 4.79 (s, 1H), 2.94 (sept, J=6.5 Hz, 1H), 2.70 (sept, J=6.6 Hz, 1H), 2.52 (sept, J=6.6 Hz, 1H), 2.22 (d, J=11.1 Hz, 1H), 2.03 (d, J=12.6 Hz, 1H), 1.57-1.37 (m, 21H), 1.32-1.26 (m, 14H), 0.99-0.92 (t, J=7.2 Hz, 12H) ppm. $^{13}C\{^1H\}$ NMR (CDCl$_3$, 150 MHz): 133.78, 128.49, 126.16, 124.76, 121.28, 120.84, 34.62, 31.04, 30.89, 30.00, 29.96, 29.25, 26.16, 24.34, 24.31, 23.01, 22.57 ppm. $^{31}P\{^1H\}$ NMR (CDCl$_3$, 121 MHz): δ9.68 ppm. Anal. Calcd for $C_{46}H_{64}ClPdP$: C, 69.95; H, 8.17; N, 0.00. Found: C, 69.61; H, 8.52; N, less than 0.02.

($\eta^3$-1-$^t$Bu-Indenyl)Pd(RuPhos)(Cl) (4d-RuPhos):

($\eta^3$-1-$^t$Bu-indenyl)$_2(\mu$-Cl)$_2$Pd$_2$ (3d) (0.300 g, 0.48 mmol) and RuPhos (0.448 g, 0.98 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.694 g, 89%.

$^1$H NMR (CDCl$_3$, 600 MHz): 7.65-7.61 (m, 1H), 7.43-7.36 (m, 2H), 7.26 (obscured by solvent, 1H), 7.01 (t, J=7.5 Hz, 1H), 6.89 (d, J=7.4 Hz, 1H), 6.83 (t, J=7.4 Hz, 1H), 6.66-6.58 (m, 4H), 6.40 (s, 1H), 4.66 (d, J=2.5 Hz, 1H), 4.52-4.44 (sept, J=6.1 Hz, 2H), 2.23 (m, 1H), 2.09 (m, 1H), 2.05-1.99 (m, 2H), 1.69-1.62 (m, 5H), 1.56 (s, 9H), 1.49-1.43 (m, 5H), 1.33-1.19 (m, 9H), 1.16-0.92 (m, 11H), 0.54 (d, J=12.2 Hz, 2H) ppm. $^{13}C\{^1H\}$ NMR (CDCl$_3$, 150 MHz): 157.25, 139.13, 137.57, 137.40, 133.08, 129.40, 128.82, 126.03, 125.66, 124.14, 120.81, 118.88, 106.47, 71.42, 71.06, 34.54, 34.51, 30.02, 29.98, 27.55, 27.44, 26.31, 22.51, 22.45, 22.42 ppm. $^{31}P\{^1H\}$ NMR (CDCl$_3$, 121 MHz): δ7.13 ppm. Anal. Calcd for $C_{43}H_{58}ClPdPO_2$: C, 66.23; H, 7.50; N, 0.00. Found: C, 66.00; H, 7.48; N, less than 0.02.

(η³-1-ᵗBu-Indenyl)Pd(SPhos)(Cl) (4d-SPhos):

(η³-1-ᵗBu-indenyl)₂(μ-Cl)₂Pd₂ (3d) (0.300 g, 0.48 mmol) and SPhos (0.395 g, 0.98 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.622 g, 86%.

¹H NMR (CDCl₃, 600 MHz): 7.73-7.68 (m, 1H), 7.45-7.42 (m, 2H), 7.41 (d, J=7.7 Hz, 1H), 7.37 (t, J=8.4 Hz, 1H), 7.03-6.97 (m, 2H), 6.79 (t, J=7.4 Hz, 1H), 6.79-6.62 (m, 3H), 6.44 (d, J=1.7 Hz, 1H), 4.39 (d, J=2.6 Hz, 1H), 3.76 (s, 3H), 3.68 (s, 3H), 2.13-1.98 (m, 4H), 1.74-1.69 (m, 2H), 1.57 (s, 9H), 1.54-1.51 (m, 6H), 1.44-1.42 (m, 2H), 1.36-1.20 (m, 5H), 1.11-0.96 (m, 3H) ppm. ¹³C{¹H} NMR (CDCl₃, 150 MHz): 138.44, 133.06, 129.78, 126.12, 124.23, 120.77, 118.91, 104.01, 103.77, 69.23, 55.62, 29.95, 29.34, 28.46, 27.29, 26.28, 25.96 ppm. ³¹P{¹H} NMR (CDCl₃, 121 MHz): δ7.50 ppm. Anal. Calcd for C₃₉H₅₀ClPdPO₂: C, 64.73; H, 6.96; N, 0.00. Found: C, 66.63; H, 6.80; N, less than 0.02.

(η³-1-ᵗBu-Indenyl)Pd(P{ᵗBu}₃)(Cl) (4d-PᵗBu₃):

(η³-1-ᵗBu-indenyl)₂(μ-Cl)₂Pd₂ (3d) (0.300 g, 0.48 mmol) and PᵗBu₃ (0.448 g, 0.98 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.694 g, 89%.

¹H NMR (CDCl₃, 600 MHz): 7.44 (d, J=7.74 Hz, 1H), 7.00-6.95 (m, 2H), 6.81-6.78 (m, 1H), 6.40 (d, J=2.64 Hz, 1H), 5.75 (s, 1H), 2.15 (s, 36H). ¹³C{¹H} NMR (CDCl₃, 150 MHz): 139.81, 127.24, 124.93, 121.14, 118.68, 107.03, 70.28, 40.65, 35.87, 33.18, 29.61 ppm. ³¹P{¹H} NMR (CDCl₃, 121 MHz): 99.95. Anal. Calcd for C₂₅H₄₀ClPdP: C, 58.48; H, 7.85; N, 0.00. Found: C, 58.59; H, 7.69; N, less than 0.02.

(η³-1-ᵗBu-Indenyl)Pd(PCy₃)(Cl) (4d-PCy₃):

(η³-1-ᵗBu-indenyl)₂(μ-Cl)₂Pd₂ (3d) (0.300 g, 0.48 mmol) and PCy₃ (0.269 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.546 g, 92%.

¹H NMR (CDCl₃, 600 MHz): 7.44 (d, J=7.75 Hz, 1H), 6.98 (t, J=7.53 Hz, 1H), 6.93 (d, J=7.39 Hz, 1H), 6.83 (t, J=7.45 Hz, 1H), 6.49 (d, J=2.56 Hz, 1H), 4.98 (d, J=2.66 Hz, 1H), 2.12-2.05 (m, 3H), 1.92-1.89 (m, 3H), 1.74-1.76 (m, 9H), 1.70-1.67 (m, 3H), 1.55 (s, 9H), 1.31-1.17 (m, 15H) ppm. ¹³C{¹H} NMR (CDCl₃, 150 MHz): 139.21, 138.07, 125.93, 124.41, 120.94, 118.32, 107.82, 64.53, 35.76, 30.31, 29.99, 27.79, 26.57, 22.57, 14.29 ppm. ³¹P{¹H} NMR (CDCl₃, 121 MHz): 48.83 ppm. Anal. Calcd for C₃₁H₄₈ClPdP: C, 62.73; H, 8.15; N, 0.00. Found: C, 62.97; H, 8.30; N, less than 0.02.

(η³-1-ᵗBu-Indenyl)Pd(P{o-tol}₃)(Cl) (4d-P(o-tol)₃):

(η³-1-ᵗBu-indenyl)₂(μ-Cl)₂Pd₂ (3d) (0.300 g, 0.48 mmol) and P(o-tol)₃ (0.262 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.550 g, 89%.

¹H NMR (CDCl₃, 600 MHz): 7.39 (d, J=7.2 Hz, 6H), 7.21 (s, 8H), 6.95 (t, J=7.46, 1H), 6.72 (s, 1H), 6.57 (s, 1H), 4.74 (s, 1H), 2.02 (s, 9H), 1.61 (s, 9H). ¹³C{¹H} NMR (CDCl₃, 150 MHz): 143.42, 139.43, 138.08, 132.31, 130.75, 126.52, 126.39, 126.00, 120.62, 117.75, 108.16, 34.99, 34.95, 30.12, 30.08, 23.16 ppm. ³¹P{¹H} NMR (CDCl₃, 121 MHz): 32.68 ppm. Anal. Calcd for C₃₄H₃₆ClPdP: C, 66.13; H, 5.88; N, 0.00. Found: C, 66.09; H, 5.74; N, less than 0.02.

(η³-1-ᵗBu-Indenyl)Pd(PPh₃)(Cl) (4d-PPhs):

(η³-1-ᵗBu-indenyl)₂(μ-Cl)₂Pd₂ (3d) (0.300 g, 0.48 mmol) and PPh₃ (0.252 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.535 g, 93%.

¹H NMR (CDCl₃, 600 MHz): 7.48-7.52 (m, 6H), 7.35-7.43 (m, 10H), 7.03 (t, J=7.62 Hz, 1H), 6.81 (t, J=7.48 Hz, 1H), 6.52 (d, J=2.71 Hz, 1H), 6.21 (d, J=7.38 Hz, 1H), 4.15 (d, J=2.83 Hz, 1H), 1.59 (s, 9H) ppm. ¹³C{¹H} NMR (CDCl₃, 150 MHz): 143.85, 137.13, 136.27, 133.97, 132.27, 131.85, 130.58, 128.26, 126.15, 125.54, 120.69, 116.47, 107.61, 97.49 ppm. ³¹P{¹H} NMR (CDCl₃, 121 MHz): 29.09 ppm. Anal. Calcd for C₃₁H₃₀ClPdP: C, 64.71; H, 5.26; N, 0.00. Found: C, 64.44; H, 5.16; N, less than 0.02.

(η³-1-ᵗBu-Indenyl)Pd(DavePhos)(Cl) (4d-DavePhos):

(η³-1-ᵗBu-indenyl)₂(μ-Cl)₂Pd₂ (3d) (0.300 g, 0.48 mmol) and DavePhos (0.378 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid, which contained two isomers in an approximately 1:1 ratio, was collected via vacuum filtration. Yield: 0.622 g, 88%.

¹H NMR (CDCl₃, 600 MHz): Isomer A: 7.78-7.74 (m, 1H), 7.48-7.40 (m, 3H), 7.39-7.34 (m, 2H), 7.19 (d, J=7.52 Hz, 1H), 7.08-6.96 (m, 3H), 6.89-6.85 (m, 1H), 6.68 (d, J=7.34 Hz, 1H), 6.33 (d, J=2.82 Hz, 1H), 4.45 (d, J=2.66 Hz 1H), 2.55 (s, 6H), 1.54 (s, 9H), 1.22-0.76 (m, 22H) ppm. Isomer B: 7.70-7.66 (m, 1H), 7.48-7.40 (m, 3H), 7.29-7.27 (m, 2H), 7.17 (d, J=7.58 Hz, 1H), 7.08-6.96 (m, 3H), 6.84-6.81 (m, 1H), 6.75 (d, J=7.31 Hz, 1H), 6.48 (d, J=2.78 Hz, 1H), 4.55 (d, J=2.71 Hz, 1H), 2.62 (s, 6H), 2.29-1.66 (m, 22H), 1.55 (s, 9H) ppm. ¹³C{¹H} NMR (CDCl₃, 150 MHz): 150.96, 150.92, 143.95, 143.63, 139.44, 139.28, 138.18, 138.04, 137.88, 137.77, 133.77, 133.72, 133.53, 133.48, 132.38, 132.26, 128.96, 125.96, 125.89, 125.80, 125.70, 124.16, 123.91, 120.78, 120.71, 120.56, 120.25, 118.23, 118.13, 43.96, 43.67, 34.58, 34.48, 34.34, 34.18, 34.13, 31.75, 31.73, 31.13, 30.39, 30.17, 29.73, 29.70, 29.14, 29.02, 28.17, 27.23, 27.04, 26.93, 26.06, 25.98, 25.78, 25.61 ppm. $^{31}$P{$^1$H} NMR (CDCl$_3$, 121 MHz): δ8.01, 56.37 ppm. Anal. Calcd for C$_{39}$H$_{51}$ClPdPN: C, 66.28; H, 7.27; N, 1.98. Found: C, 66.26; H, 7.51; N, 1.86.

(η$^3$-1-$^t$Bu-Indenyl)Pd(AmPhos)(Cl) (4d-AmPhos):

(η$^3$-1-$^t$Bu-indenyl)$_2$(μ-Cl)$_2$Pd$_2$ (3d) (0.300 g, 0.48 mmol) and AmPhos (0.255 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.526 g, 91%.

$^1$H NMR (CDCl$_3$, 600 MHz): 7.53 (t, 2H), 7.44 (d, 1H), 7.01 (t, 1H), 6.92 (d, 1H), 6.83 (t, 1H), 6.67 (d, 2H), 6.54 (d, 1H), 4.81 (d, 1H), 3.02 (s, 6H), 1.58 (s, 9H), 1.37-1.32 (m, 18H) ppm. $^{13}$C{$^1$H} NMR (CDCl$_3$, 150 MHz): 136.85, 136.76, 126.83, 124.44, 120.99, 119.18, 110.55, 110.47, 108.43, 108.38, 70.05, 70.02, 40.19, 30.48, 30.44, 30.39, 29.69, 29.65 ppm. $^{31}$P{$^1$H} NMR (CDCl$_3$, 121 MHz): 73.34 ppm. Anal. Calcd for C$_{29}$H$_{43}$ClPdPN: C, 60.21; H, 7.49; N, 2.42. Found: C, 59.64; H, 7.51; N, 2.23.

(η$^3$-1-$^t$Bu-Indenyl)Pd(QPhos)(Cl) (4d-QPhos):

(η$^3$-1-$^t$Bu-indenyl)$_2$(μ-Cl)$_2$Pd$_2$ (3d) (0.300 g, 0.48 mmol) and QPhos (0.682 g, 0.96 mmol) were added to a 100 mL Schlenk flask and placed under an atmosphere of nitrogen. THF (20 mL) was added to the flask via cannula. The resulting solution was stirred for 60 minutes, during which time the reaction mixture became homogeneous. The mixture was opened to air and 90% of the solvent was evaporated under reduced pressure. Pentane was added to precipitate solid from solution. A red-orange solid was collected via vacuum filtration. Yield: 0.870 g, 85%.

$^1$H NMR (CDCl$_3$, 600 MHz): 7.48 (d, 1H), 7.14-7.04 (m, 25H), 6.93 (t, 1H), 6.87 (d, 1H), 6.74 (t, 1H), 6.38 (d, 1H), 5.55 (d, 1H), 5.27 (s, 1H), 4.66 (s, 1H), 4.51 (d, 2H), 1.56 (s, 9H), 1.22 (d, 9H), 1.02 (d, 9H) ppm. $^{13}$C{$^1$H} NMR (CDCl$_3$, 150 MHz): 135.21, 132.77, 127.49, 126.88, 126.75, 125.35, 121.34, 118.85, 87.72, 36.08, 36.04, 31.33, 31.29, 30.41, 30.37, 29.56, 29.52 ppm. $^{31}$P{$^1$H} NMR (CDCl$_3$, 121 MHz): 73.68 ppm. Anal. Calcd for C$_{61}$H$_{62}$ClPdP: C, 71.56; H, 6.10; N, 0.00. Found: C, 70.36; H, 6.30; N, less than 0.02.

(η$^3$-1-$^t$Bu-Indenyl)Pd(BrettPhos)(Cl) (4d-BrettPhos):

In a nitrogen filled glovebox, [Pd(1-$^t$Bu-indenyl)Cl]$_2$ (156.1 mg, 0.25 mmol) and BrettPhos (268.1 mg, 0.5 mmol) were added to a 100 mL Schlenk flask equipped with a magnetic stir bar. Anhydrous THF (10 mL) was added to the flask to yield an immediate red solution. The solution was stirred for 20 minutes at room temperature, at which time the solvent was removed on a Schlenk line. Upon removal of the solvent, the flask was opened to air and the red, viscous oil was dissolved in pentane. The solution was passed through a pad of celite, followed by evaporation of the pentane using a rotary evaporator. The red solid (0.386 g, 91%) was used without further purification. X-ray quality crystals were produced by placing a concentrated pentane solution at −10' C.

$^1$H NMR (Methanol-d$_4$, 500 MHz): 7.38 (d, J=7.9 Hz, 2H), 7.35 (t, J=7.2 Hz, 1H), 7.26 (s, 1H), 7.19 (dd, J=5.6, 3.2 Hz, 1H), 7.14 (d, J=9.0 Hz, 1H), 7.05 (t, J=7.3 Hz, 1H), 6.96 (s, 1H), 6.12 (s, 1H), 5.86 (s, 1H), 3.99 (s, 3H), 3.40 (s, 3H), 2.26-2.37 (m, 3H), 2.13-2.20 (m, 1H), 1.92-2.04 (m, 4H), 1.82-1.90 (m, 3H), 1.69 (d, J=6.8 Hz, 4H), 1.38-1.64 (m, 10H), 1.36 (s, 9H), 1.30 (d, J=6.9 Hz, 6H), 1.22 (d, J=6.8 Hz, 3H), 0.98 (d, J=6.8 Hz, 3H), 0.82 (t, J=6.9 Hz, 6H) ppm. $^{31}$P{$^1$H} (Methanol-d$_4$, 121 MHz): δ5.78 ppm.

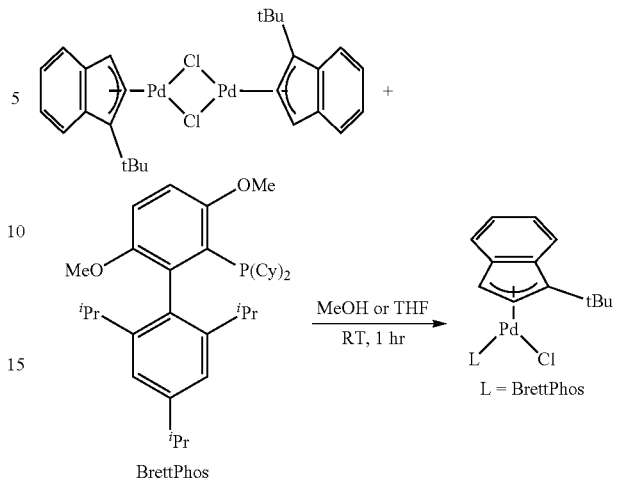

Synthetic Procedures for Large Scale Syntheses of 3d and 4d:

PdCl$_2$ (13.9 g, 78.5 mmol) and NaCl (9.19 g, 157.0 mmol) were added to a 1 L round bottom flask. MeOH (600 mL) was added and the reaction mixture heated at 50° C. for 90 minutes, at which time it became homogeneous. The solution was allowed to cool to room temperature. 1-$^t$Bu-Indene (13.5 g, 78.5 mmol) was added followed by NaHCO$_3$ (9.88 g, 117.75 mmol) and the reaction stirred for 6 hours at room temperature. The reaction mixture was filtered and the resulting black solid washed with MeOH, water and diethyl ether. The solid was dissolved in dichloromethane and the solution passed through a pad of celite. The solvent was removed using a rotary evaporator to yield a brown solid. The product was dried under vacuum to yield 3d as a brown solid. Yield: 21.6 g, 88%.

(η$^3$-1-$^t$Bu-indenyl)$_2$(μ-Cl)$_2$Pd$_2$ (1d) (6.00 g, 9.58 mmol) and IPr (7.44 g, 19.16 mmol) were added to a 500 mL Schlenk flask. Diethyl ether (200 mL) was added to the flask via cannula. The resulting solution was stirred for 120 minutes. The solution was passed through a pad of silica gel, followed by the removal of solvent using a rotary evaporator to give 4d-IPr as an orange powder. Yield: 12.1 g, 91%.

Example 2: Synthesis of [(1-$^t$Bu-Indenyl)Pd (DPPF)]Cl

In a nitrogen filled glove box, [(1-$^t$Bu-Indenyl)Pd(μ-Cl)]$_2$ (100 mg, 0.16 mmol) and 1,1'-bis(diphenylphosphino)ferrocene (DPPF) (177 mg, 0.32 mmol) were added to a 100 mL Schlenk flask. Methanol (20 mL) was added and the mixture was stirred at room temperature for 2 hours. During this time, the mixture became homogenous with a deep red color. The flask was opened to air and the solvent was removed with a rotary evaporator to yield a red oil. Pentane was added, followed by sonication; vacuum filtration produced a red crystalline solid (225 mg, 81%).

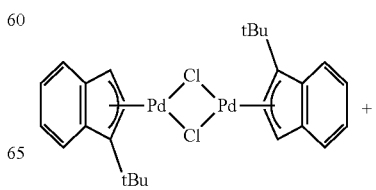

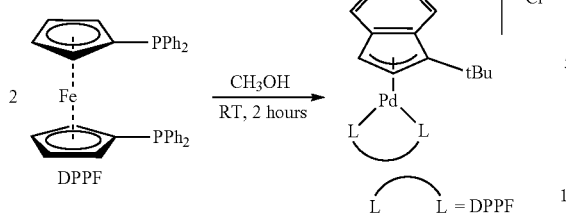

Example 3: Synthesis of [(1-$^t$Bu-Indenyl)Pd (NiXantPhos)]BF$_4$

In a nitrogen filled glove box, [(1-$^t$Bu-Indenyl)Pd(μ-Cl)]$_2$ (57 mg, 0.091 mmol) and silver tetrafluoroborate (42 mg, 0.218 mmol) were added to a 100 mL Schlenk flask. Methanol (10 mL) was added to the flask and the mixture was stirred for one hour. In a second 100 mL Schlenk flask, NiXantPhos (100 mg, 0.182 mmol) was added with methanol (10 mL). The contents of the first Schlenk flask were transferred to the second using a filter cannula, removing the silver chloride byproduct. The second Schlenk flask was stirred for an additional hour at room temperature, during which time the mixture became homogeneous. The solvent was removed under reduced pressure, followed by addition of pentane. After 10 minutes of sonication, vacuum filtration yielded the compound as an orange powder (143 mg, 86%).

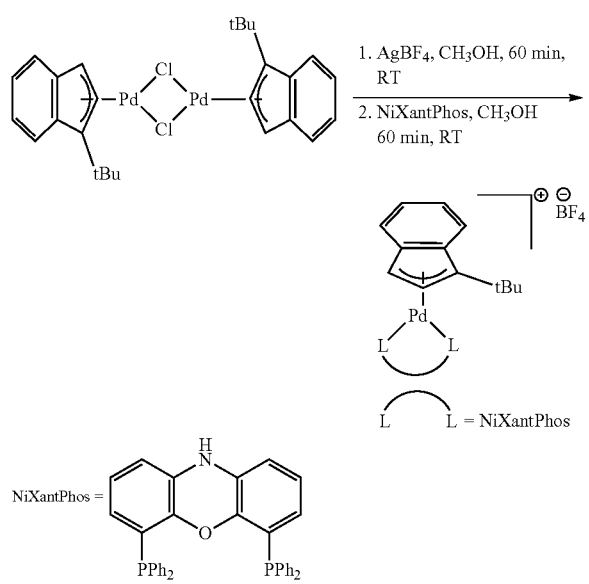

Example 4: Yields of Product for the Suzuki-Miyaura Reaction Catalyzed by Complexes 2-IPr, PEPPSI-IPr, 4a-IPr, 4b-IPr, 4c-IPr and 4d-IPr (FIG. 3)

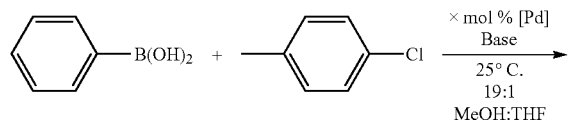

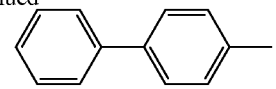

The experiments employing KO$^t$Bu as a base in FIG. 3 used a MeOH solution containing 0.5263 M 4-chlorotoluene, 0.5525 M phenylboronic acid, 0.5789 M K$^t$OBu and 0.2632 M naphthalene. The experiments employing K$_2$CO$_3$ as base in FIG. 3 used a MeOH solution containing 0.5263 M 4-chlorotoluene, 0.5525 M phenylboronic acid and 0.2632 M naphthalene. Details of how the stock solutions were prepared are given below.

KO$^t$Bu Experiments:

KO$^t$Bu (0.650 g, 5.79 mmol), phenylboronic acid (0.674 g, 5.531 mmol) and naphthalene (0.3373 g, 2.632 mmol) were transferred to a 10 mL volumetric flask in a glove box. The volumetric flask was capped with a rubber septum and placed under dinitrogen on a Schlenk line. 4-chlorotoluene (0.6232 mL, 5.268 mmol) was transferred to the volumetric flask using a 1.0 mL glass syringe. The contents were dissolved in MeOH, and the solution was diluted to 10 mL. The solution was then transferred to a flask with a Kontes valve.

K$_2$CO$_3$ Experiments:

Phenylboronic acid (0.674 g, 5.531 mmol) and naphthalene (0.3373 g, 2.632 mmol) were transferred to a 10 mL volumetric flask in a glove box. The volumetric flask was capped with a rubber septum and placed under dinitrogen on a Schlenk line. 4-chlorotoluene (0.6232 mL, 5.268 mmol) was transferred to the volumetric flask using a 1.0 mL glass syringe. The contents were dissolved in MeOH, and the solution was diluted to 10 mL. The solution was then transferred to a flask with a Kontes valve.

The concentration of the precatalyst stock solutions differed depending on the base being used in the experiment.

THF Stock Solutions for 2-IPr, PEPPSI-IPr and 4a-IPr-4d-IPr for KO$^t$Bu Experiments:

0.05 mmol of the precatalyst was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

THF Stock Solutions for 2-IPr, PEPPSI-IPr and 4a-IPr-4d-IPr for K$_2$CO$_3$ Experiments:

The precatalyst (0.1 mmol) was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

Example 5: Experimental Details for Heterogeneous Catalytic Experiments Using $^i$PrOH as Solvent and KO$^t$Bu as Base (Nolan's Original Conditions)

Phenylboronic acid (64.0 mg, 0.525 mmol), 4-chlorotoluene (59 μL, 0.50 mmol), KO$^t$Bu (61.7 mg, 0.55 mmol) and naphthalene (32.1 mg, 0.25 mmol) were added to a 1 dram vial equipped with a flea stir bar. Under an atmosphere of dinitrogen, 1 mL of degassed $^i$PrOH was added via syringe to the mixture and sealed with a septum cap. The vial was then heated using an aluminum block heater set to 25° C. After thermal equilibration, the reaction was initiated via the addition of 50 μL of the appropriate precatalyst solution in PrOH (0.05 M [Pd]). Aliquots (~50-100 μL) were removed at reaction times indicated. The aliquots were purified by filtration through pipet filters containing approximately 1 cm of silica and eluted with 1-1.2 mL of ethyl acetate directly into GC vials. Conversion was determined by comparison of the GC responses of product and the internal naphthalene standard. A comparison of the performance of 2-IPr and 2d-IPr under these conditions is given in Table 6.

Example 7: Substrate Scope Using IPr as Ancillary Ligand

Experimental Details for Table 4: Yields of Product for a Series of Suzuki-Miyaura Reactions Catalyzed by 4d-IPr and 2-IPr All catalytic reactions were performed under the same concentration and the stock solutions were prepared in the following representative manner:

KO$^t$Bu Experiments:

KO$^t$Bu (0.650 g, 5.79 mmol), boronic acid (5.531 mmol) and naphthalene (0.3373 g, 2.632 mmol) were transferred to a 10 mL volumetric flask in a glove box. The volumetric flask was capped with a rubber septum and placed under dinitrogen on a Schlenk line. Aryl chloride (5.268 mmol)

TABLE 6

Yields$^a$ of product for the Suzuki-Miyaura reaction performed using $^i$PrOH as solvent and KO$^t$Bu as base.

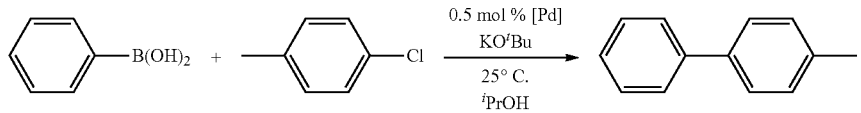

| Time (min) | % Yields for Precatalysts | |
|---|---|---|
| | 2-IPr | 4d-IPr |
| 15 | 4 | 15 |
| 30 | 10 | 35 |
| 45 | 18 | 54 |
| 60 | 29 | 78 |
| 120 | 47 | >99 |

$^a$Yields were calculated using gas chromatography with naphthalene as an internal standard and are the average of two runs.

Example 6: Experiments Involving Pd(I) Dimers

Experimental details for Equation 2; Reaction of 4d-IPr with K$_2$CO$_3$ in d$_4$-MeOH 4d-IPr (10.0 mg, 0.0144 mmol) was dissolved in 500 μL of d$_4$-MeOH. K$_2$CO$_3$ (4.0 mg, 0.0288 mmol) was added to a J. Young NMR tube. The solution was transferred to the tube at −78° C. and subsequently degassed on a Schlenk line and put under an atmosphere of dinitrogen. The heterogeneous reaction was sonicated for two hours, at which time the solvent was removed under reduced pressure on a Schlenk line. d$_6$-benzene was added to solubilize the products (although Pd black remained insoluble) and a $^1$H NMR spectrum was recorded. The only Pd containing peaks present corresponded to Pd(IPr)$_2$.

Catalysis Using 4a-IPr Under NMR Conditions:

In a glovebox, phenylboronic acid (10.0 mg, 0.082 mmol), 4-chlorotoluene (9.2 μL, 0.0781 mmol), KO$^t$Bu (9.6 mg, 0.0859 mmol) and 2,6-dimethoxytoluene (6.0 mg, 0.039 mmol) were dissolved in 400 μL of d$_4$-MeOH. 4a-IPr (2.5 mg, 0.0031 mmol) was dissolved in 100 μL of d$_8$-THF. These solutions were combined in a J. Young NMR tube and the reaction was monitored by $^1$H NMR spectroscopy for one hour at 25° C. After this time, the solvent mixture was removed on a Schlenk line and d$_6$-benzene was added. A final $^1$H NMR spectrum was recorded to identify the Pd containing products of the reaction. 7-IPr was observed as the main Pd containing product, with a yield of 85% compared to the internal standard 2,6-dimethoxytoluene.

was transferred to the volumetric flask using a 1.0 mL glass syringe. The contents were dissolved in MeOH, and the solution was diluted to 10 mL. The solution was then transferred to a flask with a Kontes valve.

K$_2$CO$_3$ Experiments:

Boronic acid (5.531 mmol) and naphthalene (0.3373 g, 2.632 mmol) were transferred to a 10 mL volumetric flask in a glove box. The volumetric flask was capped with a rubber septum and placed under dinitrogen on a Schlenk line. Aryl chloride (5.268 mmol) was transferred to the volumetric flask using a 1.0 mL glass syringe. The contents were dissolved in MeOH, and the solution was diluted to 10 mL. The solution was then transferred to a flask with a Kontes valve.

Precatalyst Stock Solutions Used in 0.1 Mol % Reactions:

0.01 mmol of 2-IPr or 4d-IPr was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

Precatalyst Stock Solutions Used in 0.2 Mol % Reactions:

0.02 mmol of 2-IPr or 4d-IPr was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

Precatalyst Stock Solutions Used in 0.5 Mol % Reactions:
0.05 mmol of 2-IPr or 4d-IPr was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

Precatalyst Stock Solutions Used in 1.0 Mol % Reactions:
2-IPr or 4d-IPr (0.1 mmol) was transferred into a 1 mL volumetric flask on the bench top. The flask was capped with a septum, and placed under dinitrogen (by cycling three times between vacuum and dinitrogen) on a Schlenk line. The precatalyst was dissolved in THF, and the solution was diluted to 1 mL. The solution was transferred to a flask with a Kontes valve.

Example 8: Tetra-Ortho Substituted Suzuki Miyaura Reactions Using IPr*$^{OMe}$

General Procedure A:

In a nitrogen filled glove box, aryl halide (0.5 mmol), if solid, boronic acid (0.75 mmol), KOH (1.0 mmol) and 4d-IPr*$^{OMe}$ (0.005 mmol, 0.5 mol % or 0.01 mmol, 1.0 mol %) were added to a 1 dram vial equipped with a magnetic stir bar. Aryl chloride (0.5 mmol), if liquid, was added by syringe, followed by THF (1 mL). The vial was sealed and stirred outside of the glove box at 80° C. for 12 hours. At this point, the vial was opened to air and diethyl ether (10 mL) and H$_2$O (10 mL) were added to the reaction mixture. The aqueous phase was extracted with diethyl ether (3×10 mL). The combined organic phases were dried over MgSO$_4$ and filtered. The supernatant was then passed through a pad of silica gel, followed by removal of the solvent under reduced pressure to give the organic product.

$^1$H NMR data for the following compounds were consistent with those published in Bastug & Nolan, 2014, Organometallics 33:1253-1258.

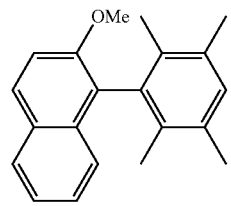 [SMILES: COc1ccc2ccccc2c1-c1c(C)c(C)cc(C)c1C]

2-Methoxy-1-(2,3,5,6-tetramethylphenyl)naphthalene. Following General Procedure A, a mixture of 1-bromo-2-methoxynaphthalene (118 mg, 0.5 mmol), 2,3,5,6-tetramethylphenyl boronic acid (133 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 94% (136 mg).

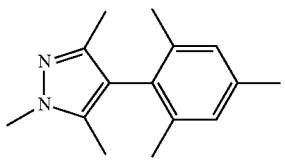

4-Mesityl-1,3,5-trimethyl-1H-pyrazole. Following General Procedure A, a mixture of 4-bromo-1,3,5-trimethyl-1H-pyrazole (92 mg, 0.5 mmol), 2,4,6-trimethylphenyl boronic acid (123 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 95% (108 mg).

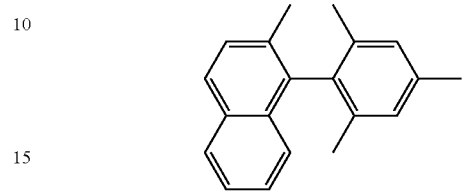

1-Mesityl-2-methylnaphthalene. Following General Procedure A, a mixture of 1-bromo-2-methylnaphthalene (78 μL, 0.5 mmol), 2,4,6-trimethylphenyl boronic acid (123 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 98% (127 mg).

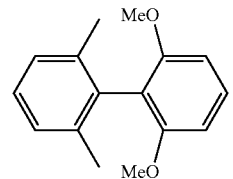 [SMILES: COc1cccc(OC)c1-c1c(C)cccc1C]

2,6-dimethyl-2',6'-dimethoxy-1,1'-biphenyl. Following General Procedure A, a mixture of 2-chloro-m-xylene (66 μL, 0.5 mmol), 2,6-dimethoxyphenyl boronic acid (137 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 94% (114 mg).

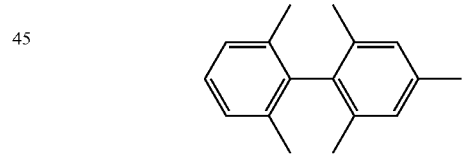

2,2',4,6,6'-pentamethyl-1,1'-biphenyl. Following General Procedure A, a mixture of 2-chloro-m-xylene (66 μL, 0.5 mmol), 2,4,6-trimethylphenyl boronic acid (123 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 82% (92 mg).

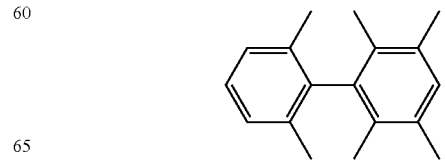

2,2',3,5,6,6'-hexamethyl-1,1'-biphenyl. Following General Procedure A, a mixture of 2-chloro-m-xylene (66 μL, 0.5 mmol), 2,3,5,6-tetramethylphenyl boronic acid (133 mg, 0.75 mmol), potassium hydroxide (56 mg, 1.0 mmol), 4d-IPr*$^{OMe}$ (3.2 mg, 0.0025 mmol) and THF (1 mL) was stirred at 80° C. for 12 hours. The average of two runs provided a yield of 92% (110 mg).

Example 9: Suzuki-Miyaura Reactions with Heterocyclic Boronic Acid Using XPhos

General Procedure B:

In a nitrogen filled glove box, aryl chloride (1.0 mmol), if solid, boronic acid (1.5 mmol), K$_2$CO$_3$ (2.0 mmol) and 4d-XPhos (0.01 mmol, 1 mol %) were added to a 4 dram vial equipped with a magnetic stir bar. Aryl chloride (1.0 mmol), if liquid, was added by syringe, followed by methanol (4 mL) and THF (2 mL). The vial was sealed and stirred outside of the glove box at room temperature or 40° C. for one hour. At this point, the vial was opened to air and diethyl ether (10 mL) and H$_2$O (10 mL) were added to the reaction mixture. The aqueous phase was extracted with diethyl ether (3×10 mL). The combined organic phases were dried over MgSO$_4$ and filtered. The supernatant was then passed through a pad of silica gel, followed by removal of the solvent under reduced pressure to give the organic product.

$^1$H NMR data (and $^{19}$F NMR data, if applicable) for the following compounds were consistent with those published in Kinzel, et al., 2010, J. Am. Chem. Soc. 2010, 132, 14073-14075; and/or Bruno, et al., 2013, Chem. Sci. 4:916-920.

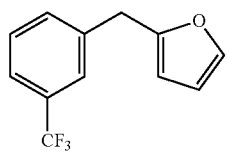

2-(3-(trifluoromethyl)benzyl)furan. Following General Procedure B, a mixture of 1-(chloromethyl)-3-(trifluoromethyl)benzene (151 μL, 1.0 mmol), 2-furan boronic acid (168 mg, 1.5 mmol), K$_2$CO$_3$ (276 mg, 2.0 mmol), 4d-XPhos (7.9 mg, 0.01 mmol), THF (2 mL), and methanol (4 mL) were stirred at 40° C. for one hour. The average of two runs provided a yield of 92% (210 mg).

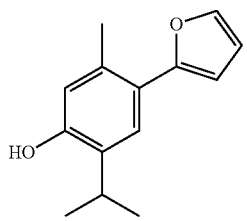 [SMILES: Cc1cc(O)c(C(C)C)cc1-c1ccco1]

4-(furan-2-yl)-2-isopropyl-5-methylphenol. Following General Procedure B, a mixture of 4-chloro-2-isopropyl-5-methylphenol (185 μg, 1.0 mmol), 2-furan boronic acid (168 mg, 1.5 mmol), K$_2$CO$_3$ (276 mg, 2.0 mmol), 4d-XPhos (7.9 mg, 0.01 mmol), THF (2 mL), and methanol (4 mL) were stirred at RT for one hour. The average of two runs provided a yield of 94% (203 mg).

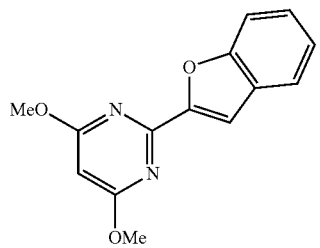 [SMILES: COc1cc(OC)nc(-c2cc3ccccc3o2)n1]

2-(benzofuran-2-yl)-4,6-dimethoxypyrimidine. Following General Procedure B, a mixture of 2-chloro-4,6-dimethoxypyrimidine (175 μg, 1.0 mmol), benzofuran-2-boronic acid (243 mg, 1.5 mmol), K$_2$CO$_3$ (276 mg, 2.0 mmol), 4d-XPhos (7.9 mg, 0.01 mmol), THF (2 mL), and methanol (4 mL) were stirred at 40° C. for one hour. The average of two runs provided a yield of 95% (244 mg).

5-(benzofuran-2-yl)-1H-indole. Following General Procedure B, a mixture of 4-chloroindole (152 μg, 1.0 mmol), benzofuran-2-boronic acid (243 mg, 1.5 mmol), K$_2$CO$_3$ (276 mg, 2.0 mmol), 4d-XPhos (7.9 mg, 0.01 mmol), THF (2 mL), and methanol (4 mL) were stirred at 40° C. for one hour. The average of two runs provided a yield of 94% (220 mg).

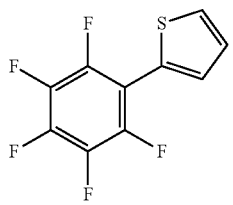 [SMILES: Fc1c(F)c(F)c(-c2cccs2)c(F)c1F]

2-(perfluorophenyl)thiophene. Following General Procedure B, a mixture of pentafluorochlorobenzene (130 μL, 1.0 mmol), 2-thiophene boronic acid (192 mg, 1.5 mmol), K$_2$CO$_3$ (276 mg, 2.0 mmol), 4d-XPhos (7.9 mg, 0.01 mmol), THF (2 mL), and methanol (4 mL) were stirred at RT for one hour. The average of two runs provided a yield of 93% (232 mg).

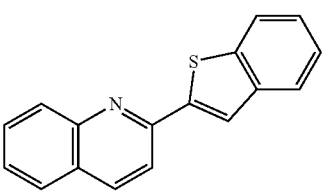 [SMILES: c1ccc2nc(-c3cc4ccccc4s3)ccc2c1]

2-(benzo[b]thiophen-2-yl)quinoline. Following General Procedure B, a mixture of 2-chloroquinoline (164 μg, 1.0 mmol), benzothiophene-2-boronic acid (267 mg, 1.5 mmol), K₂CO₃ (276 mg, 2.0 mmol), 4d-XPhos (7.9 mg, 0.01 mmol), THF (2 mL), and methanol (4 mL) were stirred at 40° C. for one hour. Dichloromethane was used for work up, instead of diethyl ether, due to factors associated with solubility. The average of two runs provided a yield of 98% (220 mg).

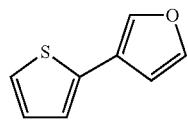

3-(thiophen-2-yl)furan. Following General Procedure B, a mixture of 2-chlorothiophene (92 µL, 1.0 mmol), 3-furan boronic acid (168 mg, 1.5 mmol), K₂CO₃ (276 mg, 2.0 mmol), 4d-XPhos (7.9 mg, 0.01 mmol), THF (2 mL), and methanol (4 mL) were stirred at 40° C. for one hour. The average of two runs provided a yield of 95% (143 mg).

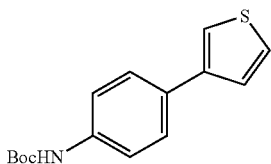 [SMILES: CC(C)(C)OC(=O)Nc1ccc(-c2ccsc2)cc1]

tert-butyl 4-(4-(thiophen-3-yl)phenyl)piperazine-1-carboxylate. Following General Procedure B, a mixture of tert-butyl-(4-chlorophenyl)-carbamate (228 mg, 1.0 mmol), 3-thiophene boronic acid (192 mg, 1.5 mmol), K₂CO₃ (276 mg, 2.0 mmol), 4d-XPhos (7.9 mg, 0.01 mmol), THF (2 mL), and methanol (4 mL) were stirred at RT for one hour. The average of two runs provided a yield of 95% (143 mg).

Example 10: Suzuki-Miyaura Reactions with Indazoles or Benzimidazoles Using SPhos General Procedure C:

In a nitrogen filled glove box, aryl chloride (1.0 mmol), boronic acid (2.0 mmol), K₂CO₃ (2.0 mmol) and 4d-SPhos (0.02 mmol, 2 mol %) were added to a 4 dram vial equipped with a magnetic stir bar. Methanol (4 mL) and 1,4-dioxane (2 mL) were added via syringe. The vial was sealed and stirred outside of the glove box in a pre-calibrated oil bath at 80° C. for 15 hours. At this time, the vial was opened to air and ethyl acetate (10 mL) and H₂O (10 mL) were added. The aqueous phase was extracted with ethyl acetate (3×10 mL) and the combined organic phase was dried over MgSO₄. After filtration, the supernatant was passed through a pad of silica gel and celite and washed with ethyl acetate. The solvent was removed under reduced pressure to give the organic product.

¹H NMR data for the following compounds were consistent with those published in Düfert, et al., 2013, J. Am. Chem. Soc. 135:12877-12885.

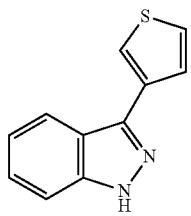 [SMILES: c1ccc2c(-c3ccsc3)n[nH]c2c1]

3-(thiophen-3-yl)-1H-indazole. Following General Procedure C, a mixture of 3-chloro indazole (153 mg, 1.0 mmol), 3-thiophene boronic acid (256 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 98% (196 mg).

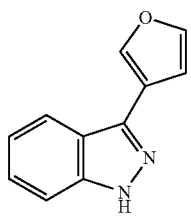 [SMILES: c1ccc2c(-c3ccoc3)n[nH]c2c1]

3-(furan-3-yl)-1H-indazole. Following General Procedure C, a mixture of 3-chloro indazole (153 mg, 1.0 mmol), 3-furan boronic acid (224 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 97% (177 mg).

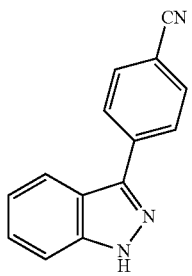 [SMILES: N#Cc1ccc(-c2n[nH]c3ccccc23)cc1]

4-(1H-indazol-3-yl)benzonitrile. Following General Procedure C, a mixture of 3-chloro indazole (153 mg, 1.0 mmol), 4-cyanophenyl boronic acid (294 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 90% (197 mg).

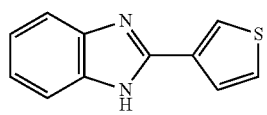 [SMILES: c1ccc2[nH]c(-c3ccsc3)nc2c1]

2-(thiophen-3-yl)-1H-benzo[d]imidazole. Following General Procedure C, a mixture of 2-chlorobenzimidazole (153 mg, 1.0 mmol), 3-thiophene boronic acid (256 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 98% (198 mg).

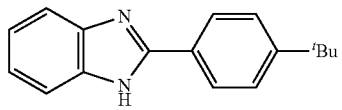 [SMILES: CC(C)(C)c1ccc(-c2nc3ccccc3[nH]2)cc1]

2-(4-tert-butylphenyl)-1H-benzo[d]imidazole. Following General Procedure C, a mixture of 2-chlorobenzimidazole (153 mg, 1.0 mmol), 4-tert-butylphenyl boronic acid (356 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 94% (236 mg).

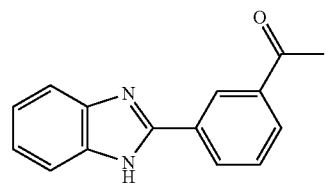 [SMILES: CC(=O)c1cccc(-c2nc3ccccc3[nH]2)c1]

1-(3-(1H-benzo[d]imidazol-2-yl)phenyl)ethanone. Following General Procedure C, a mixture of 2-chlorobenzimidazole (153 mg, 1.0 mmol), 3-acetylphenyl boronic acid (328 mg, 2.0 mmol), K₂CO₃ (276 mg, 2.0 mmol), 4d-SPhos (14.5 mg, 0.02 mmol), 1,4-dioxane (4 mL) and methanol (2 mL) were stirred at 80° C. for 15 hours. The average of two runs provided a yield of 91% (214 mg).

Example 11: Buchwald-Hartwig Reactions Using RuPhos

General Procedure D:

In a nitrogen filled glove box, aryl halide (1.0 mmol), if solid, amine (1.2 mmol), if solid, NaO^tBu (115 mg, 1.2 mmol), 4d-RuPhos (4.0 mg, 0.005 mmol) and RuPhos (2.3 mg, 0.005 mmol) were added to a 1 dram vial equipped with a magnetic stir bar. Amine (1.2 mmol), if liquid, and aryl halide (1.0 mmol), if liquid, were added via syringe along with THF (1 mL). The vial was sealed and stirred outside the glove box in a pre-calibrated heating block for 6 hours at 85° C. At this time, the vial was cooled to room temperature and ethyl acetate (10 mL) and water (10 mL) were added. The aqueous phase was extracted with ethyl acetate (3×10 mL); the organic phase was dried over MgSO₄ and subsequently filtered. The supernatant was passed through a pad of silica gel, followed by evaporation of the solvent to give the organic product.

¹H NMR data for the following compounds were consistent with those published in Bruno, et al., 2013, Chem. Sci. 4:916-920.

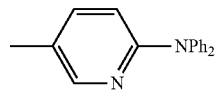

5-methyl-N,N-diphenylpyridin-2-amine. Following General Procedure D, a mixture of 2-chloro-5-methylpyridine (110 µL, 1.0 mmol), diphenylamine (203 mg, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 94% (244 mg).

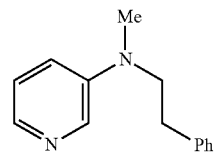 [SMILES: CN(CCc1ccccc1)c1cccnc1]

N-methyl-N-phenethylpyridin-3-amine. Following General Procedure D, a mixture of 3-chloropyridine (96 µL, 1.0 mmol), N-methylphenethyl amine (174 µL, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 96% (204 mg).

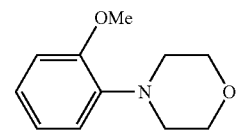 [SMILES: COc1ccccc1N1CCOCC1]

4-(2-methoxyphenyl)morpholine. Following General Procedure D, a mixture of 2-chloroanisole (122 µL, 1.0 mmol), morpholine (104 µL, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 96% (185 mg).

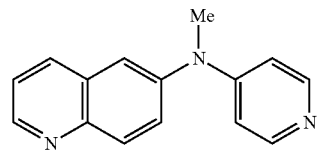 [SMILES: CN(c1ccncc1)c1ccc2ncccc2c1]

N-methyl-N-(pyridin-4-yl)quinolin-6-amine. Following General Procedure D, a mixture of 6-chloroquinoline (164 mg, 1.0 mmol), N-methyl-4-aminopyridine (130 mg, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 91% (214 mg).

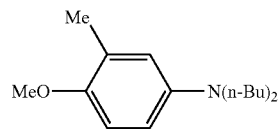

N,N-dibutyl-4-methoxy-3-methylaniline. Following General Procedure D, a mixture of 4-bromo-2-methylanisole (201 mg, 1.0 mmol), di-n-butylamine (202 µL, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 90% (224 mg).

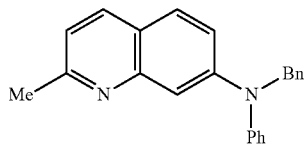 [SMILES: Cc1ccc2ccc(N(Cc3ccccc3)c3ccccc3)cc2n1]

N-benzyl-2-methyl-N-phenylquinolin-7-amine. Following General Procedure D, a mixture of 7-chloro-2-methylquinoline (177 mg, 1.0 mmol), N-benzylaniline (220 mg, 1.2 mmol), NaO^tBu (115 mg, 1.2 mmol), 4d-RuPhos (4.0 mg, 0.005 mmol), RuPhos (2.3 mg, 0.005 mmol) and THF (1 mL) were stirred at 85° C. for 6 hours. The average of two runs provided a yield of 82% (265 mg).

Example 12: Alpha-Arylation Reactions Using XPhos

General Procedure E:

In a nitrogen filled glove box, KO^tBu (112 mg, 1.0 mmol) and 4d-XPhos (4.0 mg, 0.005 mmol) were added to a one dram vial equipped with a magnetic stir bar. Aryl chloride (0.525 mmol) and aryl methyl ketone (0.5 mmol) were added to the vial via syringe. THF (1 mL) and methanol (1 mL) were added, and the vial was sealed and stirred outside of the glove box in a pre-calibrated heating block for one hour at 60° C. At this time, an aqueous solution of $NH_4Cl$ (10 mL) was added. The product was extracted with ethyl acetate (3×10 mL), which was then dried over $MgSO_4$ and filtered. The resulting supernatant was passed through a pad of silica gel, followed by removal of the solvent under reduced pressure to give the organic product.

$^1H$ NMR for the following compounds were consistent with those published in Biscoe & Buchwald, 2009, Org. Lett. 11:1773-1775.

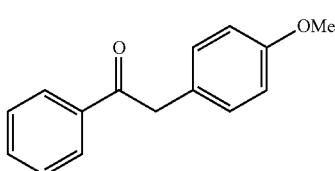

2-(4-Methoxyphenyl)-1-phenylethanone. Following General Procedure E, a mixture of acetophenone (59 μL, 0.5 mmol), 4-chloroanisole (64 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 97% (110 mg).

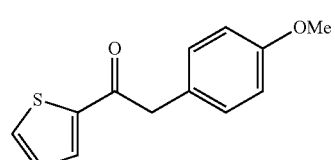

2-(4-Methoxyphenyl)-1-(thiophen-2-yl)ethanone. Following General Procedure E, a mixture of 2-acetylthiophene (54 μL, 0.5 mmol), 4-chloroanisole (64 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 90% (105 mg).

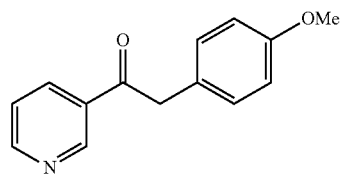 [SMILES: COc1ccc(CC(=O)c2cccnc2)cc1]

2-(4-Methoxyphenyl)-1-(pyridin-3-yl)ethanone. Following General Procedure E, a mixture of 3-acetylpyridine (55 μL, 0.5 mmol), 4-chloroanisole (64 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 93% (106 mg).

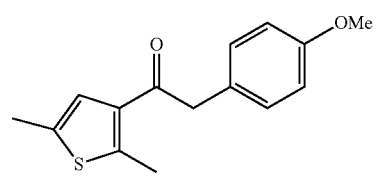 [SMILES: COc1ccc(CC(=O)c2cc(C)sc2C)cc1]

1-(2,5-Dimethylthiophen-3-yl)-2-(4-methoxyphenyl) ethanone. Following General Procedure E, a mixture of 1-(2,5-dimethyl-3-thienyl)-ethanone (72 μL, 0.5 mmol), 4-chloroanisole (64 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 95% (124 mg).

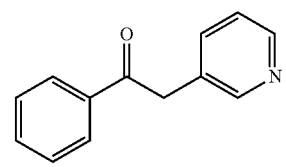 [SMILES: O=C(Cc1cccnc1)c1ccccc1]

1-Phenyl-2-(pyridin-3-yl)ethanone. Following General Procedure E, a mixture of acetophenone (59 μL, 0.5 mmol), 3-chloropyridine (50 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 94% (92 mg).

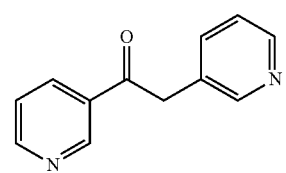 [SMILES: O=C(Cc1cccnc1)c1cccnc1]

1,2-Di(pyridin-3-yl)ethanone. Following General Procedure E, a mixture of 3-acetylpyridine (55 μL, 0.5 mmol), 3-chloropyridine (50 μL, 0.525 mmol), KO^tBu (112 mg, 1.0 mmol), 4d-XPhos (4.0 mg, 0.005 mmol), THF (1 mL) and methanol (1 mL) were stirred at 60° C. for 1 hour. The average of two runs provided a yield of 91% (90 mg).

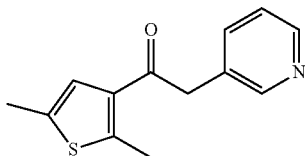

1-(2,5-Dimethylthiophen-3-yl)-2-(pyridin-3-yl)ethanone. Following General Procedure E, a mixture of 1-(2,5-dimethyl-3-thienyl)-ethanone (72 μL, 0.5 mmol), 3-chloropyridine (50 μL, 0.525 mmol), KO$^t$Bu (112 mg, 1.0 mmol), 4d-XPhos (4.0 mg, 0.005 mmol), THF (1 mL) and methanol (1 mL) were stirred at 60° C. for 1 hour. The average of two runs provided a yield of 92% (106 mg).

Example 13: Suzuki-Miyaura Reactions with Alkyl Trifluoroboronates Using P$^t$Bu$_3$ General Procedure F:

In a nitrogen filled glove box, potassium alkyl trifluoroboronate salt (0.75 mmol), K$_2$CO$_3$ (207 mg, 1.5 mmol), 4d-P$^t$Bu$_3$ (2.6 mg or 5.2 mg, 0.005 mmol or 0.01 mmol) and aryl chloride (0.5 mmol), if solid, were added to a one dram vial equipped with a magnetic stir bar. Aryl chloride (0.5 mmol), if liquid, was added via syringe, followed by addition of toluene (1 mL) and water (0.5 mL). The reaction was stirred outside of the glove box in a pre-calibrated heating block at 80° C. for 8 hours. At this time, aqueous NH$_4$Cl (10 mL) was added. Ethyl acetate (3×10 mL) was used to extract the product, which was then subsequently dried over MgSO$_4$ and filtered. The supernatant was passed through a pad of silica gel, followed by evaporation of the solvent via reduced pressure to give the organic product.

$^1$H NMR for the following compounds were consistent with those published in Li, et al., 2014, J. Am. Chem. Soc. 136:14027-14030.

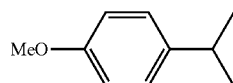

4-iso-propylanisole. Following General Procedure F, a mixture of 4-chloroanisole (61 μL, 0.5 mmol), potassium iso-propyltrifluoroborate (113 mg, 0.75), K$_2$CO$_3$ (207 mg, 1.5 mmol), 4d-P$^t$Bu$_3$ (5.2 mg, 0.01 mmol), toluene (1 mL) and H$_2$O (0.5 mL) were stirred at 80° C. for 8 hours. The average of two runs provided a yield of 95% (72 mg).

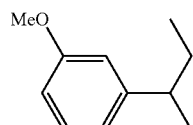

3-(sec-Butyl)-anisole. Following General Procedure F, a mixture of 3-chloroanisole (61 μL, 0.5 mmol), potassium sec-butyltrifluoroborate (123 mg, 0.75), K$_2$CO$_3$ (207 mg, 1.5 mmol), 4d-P$^t$Bu$_3$ (2.6 mg, 0.005 mmol), toluene (1 mL) and H$_2$O (0.5 mL) were stirred at 80° C. for 8 hours. The average of two runs provided a yield of 94% (77 mg).

1-Cyclopropyl-4-nitrobenzene. Following General Procedure F, a mixture of 4-chloro nitrobenzene (79 mg, 0.5 mmol), potassium cyclopropyltrifluoroborate (123 mg, 0.75), K$_2$CO$_3$ (207 mg, 1.5 mmol), 4d-P$^t$Bu$_3$ (2.6 mg, 0.005 mmol), toluene (1 mL) and H$_2$O (0.5 mL) were stirred at 40° C. for 8 hours. The average of two runs provided a yield of 97% (79 mg).

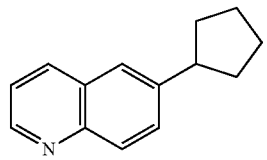 [SMILES: c1cnc2ccc(C3CCCC3)cc2c1]

6-Cyclopentylquinoline. Following General Procedure F, a mixture of 6-chloroquinoline (82 mg, 0.5 mmol), potassium cyclopentyltrifluoroborate (132 mg, 0.75), K$_2$CO$_3$ (207 mg, 1.5 mmol), 4d-P$^t$Bu$_3$ (5.6 mg, 0.01 mmol), toluene (1 mL) and H$_2$O (0.5 mL) were stirred at 80° C. for 8 hours. The average of two runs provided a yield of 89% (88 mg).

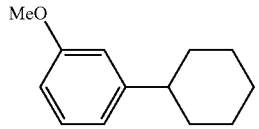 [SMILES: COc1cccc(C2CCCCC2)c1]

3-cyclohexylanisole. Following General Procedure F, a mixture of 3-chloroanisole (61 μL, 0.5 mmol), potassium cyclohexyltrifluoroborate (143 mg, 0.75), K$_2$CO$_3$ (207 mg, 1.5 mmol), 4d-P$^t$Bu$_3$ (5.6 mg, 0.01 mmol), toluene (1 mL) and H$_2$O (0.5 mL) were stirred at 80° C. for 8 hours. The average of two runs provided a yield of 86% (83 mg).

Example 14: Assorted Catalytic Reactions Using In Situ Generated Precatalysts

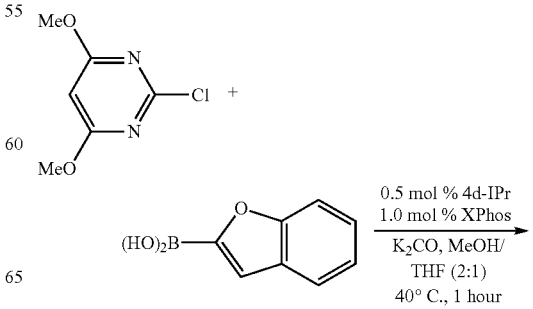

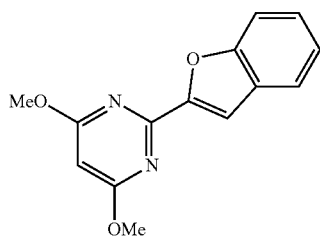

In a nitrogen filled glove box, 3d (15.5 mg, 0.025 mmol) and XPhos (24 mg, 0.05 mmol) were added to a 2 dram vial equipped with a magnetic stir bar. THF (5 mL) was added to the vial via syringe; the mixture was stirred for 10 minutes. In a 4 dram vial, 2-chloro-4,6-dimethoxypyrimidine (175 mg, 1.0 mmol), benzofuran-2-boronic acid (243 mg, 1.5 mmol) and $K_2CO_3$ (276 mg, 2.0 mmol) were added with a magnetic stir bar. THF (1 mL) and methanol (4 mL) were added to the vial via syringe, followed by 1 mL of the THF/precatalyst solution. The vial was sealed and stirred outside of the glove box in a pre-calibrated heating block at 40° C. for one hour. General Procedure B was followed to yield the product in a 95% yield (242 mg).

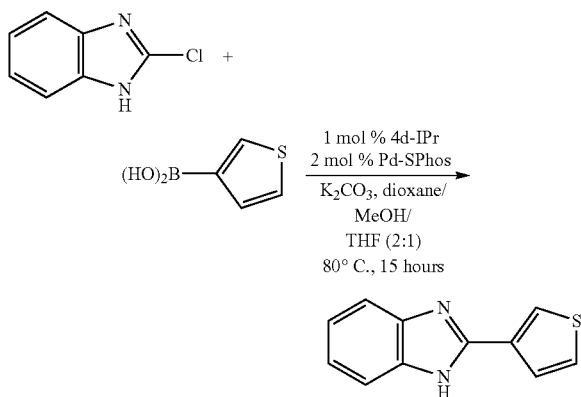

In a nitrogen filled glove box, 3d (31.0 mg, 0.05 mmol) and SPhos (41 mg, 0.1 mmol) were added to a 2 dram vial equipped with a magnetic stir bar. 1,4-dioxane (5 mL) was added to the vial via syringe; the mixture was stirred for 10 minutes. In a 4 dram vial, 2-chloro-1H-benzimidazole (153 mg, 1.0 mmol), 3-thiophene boronic acid (256 mg, 2.0 mmol) and $K_2CO_3$ (276 mg, 2.0 mmol) were added with a magnetic stir bar. 1,4-dioxane (3 mL) and methanol (2 mL) were added to the vial via syringe, followed by 1 mL of the 1,4-dioxane/precatalyst solution. The vial was sealed and stirred outside of the glove box in a pre-calibrated heating block at 80° C. for 15 hours. General Procedure C was followed to yield the product in a 95% yield (192 mg).

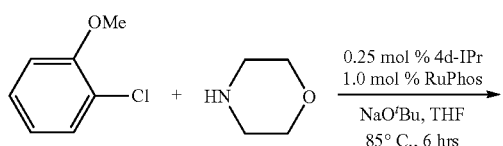

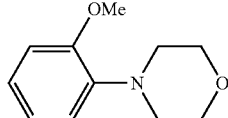

In a nitrogen filled glove box, 3d (8.0 mg, 0.0125 mmol) and RuPhos (23.5 mg, 0.025 mmol) were added to a 2 dram vial equipped with a magnetic stir bar. THF (5 mL) was added to the vial via syringe; the mixture was stirred for 10 minutes. In a one dram vial, NaO$^t$Bu (115 mg, 1.2 mmol) was added with a magnetic stir bar. 2-methoxy chlorobenzene (122 μL, 1.0 mmol) and morpholine (104 μL, 1.2 mmol) were added via syringe, followed by 1 mL of THF/precatalyst solution. The vial was sealed and stirred outside of the glove box in a pre-calibrated heating block at 85° C. for 6 hours. General Procedure D was followed to yield the product in a 94% yield (182 mg).

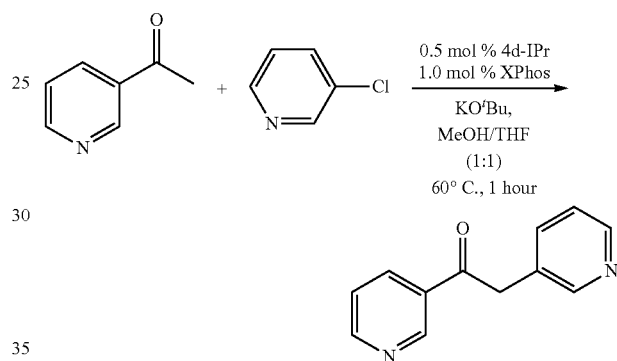

In a nitrogen filled glove box, 3d (15.5 mg, 0.025 mmol) and XPhos (24 mg, 0.05 mmol) were added to a 2 dram vial equipped with a magnetic stir bar. THF (5 mL) was added to the vial via syringe; the mixture was stirred for 10 minutes. In a 1 dram vial, KO$^t$Bu (134 mg, 1.2 mmol) was added with a magnetic stir bar; 3-acetylpyridine (50 μL, 0.5 mmol) and 3-chloropyridine (55 μL, 0.525 mmol) were added by syringe. THF (0.5 mL) and methanol (1 mL) were added to the vial via syringe, followed by 0.5 mL of the THF/precatalyst solution. The vial was sealed and stirred outside of the glove box in a pre-calibrated heating block at 60° C. for one hour. General Procedure E was followed to yield the product in a 89% yield (88 mg).

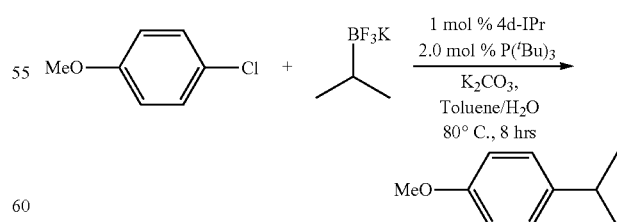

In a nitrogen filled glove box, 3d (15.5 mg, 0.025 mmol) and P($^t$Bu)$_3$ (10 mg, 0.05 mmol) were added to a 2 dram vial equipped with a magnetic stir bar. Toluene (5 mL) was added to the vial via syringe; the mixture was stirred for 30 minutes. In a 1 dram vial, potassium isopropyltrifluoroboronate (113 mg, 0.75 mmol) and K$_2$CO$_3$ (207 mg, 1.5 mmol) were added with a magnetic stir bar; 4-chloroanisole (61 µL, 0.5 mmol) was added by syringe. Water (0.5 mL) was added to the vial via syringe, followed by 1.0 mL of the toluene/precatalyst solution. The vial was sealed and stirred outside of the glove box in a pre-calibrated heating block at 80° C. for 8 hours. General Procedure F was followed to yield the product in a 97% yield (146 mg).

Example 15: In Situ Catalytic Experiments Comparing (η$^3$-Cinnamyl)$_2$(µ-Cl)$_2$Pd$_2$ and 3d as Precatalysts with IPr The MeOH stock solutions used in FIG. 3 were used. Preparation of Precatalyst Stock Solutions for 0.5 Mol % Reactions:

(η$^3$-cinnamyl)$_2$(µ-Cl)$_2$Pd$_2$ (12.5 mg, 0.0244 mmol) or 3d (15.0 mg, 0.0244 mmol) and IPr (19.0 mg, 0.049 mmol) were added to a 1 mL volumetric flask in a glovebox. THF was added and the solution was diluted to 1 mL. The homogeneous solutions were transferred to 1 dram vials equipped with flea stir bars and the solutions were stirred for one hour at 25° C. After this time, the solutions were transferred to flasks with Kontes valves. The solutions were used in catalytic experiments without further purification. Preparation of Precatalyst Stock Solutions for 1.0 Mol % Reactions:

(η$^3$-cinnamyl)$_2$(µ-Cl)$_2$Pd$_2$ (25.0 mg, 0.049 mmol) or 3d (30.0 mg, 0.049 mmol) and IPr (38.0 mg, 0.098 mmol) were added to a 1 mL volumetric flask in a glovebox. THF was added and the solution was diluted to 1 mL. The homogeneous solutions were transferred to 1 dram vials equipped with flea stir bars and the solutions were stirred for one hour at 25° C. After this time, the solutions were transferred to flasks with Kontes valves. The solutions were used in catalytic experiments without further purification.

A comparison of the performance of (η$^3$-cinnamyl)$_2$(µ-Cl)$_2$Pd$_2$ and 3d under these conditions is given is given in Table 5. The system generated from 3d is a significantly more efficient.

Example 16: One-Pot, In Situ-Catalyst Generation for Heteroaryl Cross Coupling Reaction In a nitrogen filled glove box, 3d (3.1 mg, 0.005 mmol), XPhos (4.8 mg, 0.005 mmol), 2-chloro-4,6-dimethoxyprimidine (175 mg, 1.0 mmol), benzofuran-2-boronic acid (243 mg, 1.5 mmol) and K$_2$CO$_3$ (276 mg, 2.0 mmol) were added to a 4 dram vial with a magnetic stir bar. THF (12 mL) and methanol (4 mL) were added to the vial via syringe. The vial was sealed and stirred outside of the glove box in a pre-calibrated heating block at 40° C. for one hour. General Procedure B was followed to yield the product in a 95% yield (242 mg).

Example 17: Procedures for Suzuki-Miyaura Reactions Using Monomeric Precatalysts of the Invention KO$^t$Bu Conditions:

Reactions were performed under dinitrogen in a 1 dram vial containing a flea stir bar and sealed with a septum cap. To the vial were added 950 µL of a MeOH stock solution, containing 0.5263 M aryl chloride, 0.5525 M boronic acid, 0.5789 M KO$^t$Bu and 0.2632 M naphthalene. The vial was then heated using an aluminum block heater set to 25° C. After thermal equilibration, the reaction was initiated via the addition of 50 µL of the appropriate precatalyst solution in THF (0.1 M [Pd]). Aliquots (~50-100 µL) were removed at reaction times indicated. The aliquots were purified by filtration through pipet filters containing approximately 1 cm of silica and eluted with 1-1.2 mL of ethyl acetate directly into GC vials. Conversion was determined by comparison of the GC responses of product and the internal naphthalene standard.

K$_2$CO$_3$ Conditions:

Potassium carbonate (0.75 mmol) was transferred on the benchtop into a 1 dram vial containing a flea stir bar. The vial was sealed with a septum cap, and placed under dinitrogen (by cycling three times between vacuum and dinitrogen) on a Schlenk line through a needle. To the vial was added 950 µL of a MeOH stock solution, containing 0.5263 M aryl chloride, 0.5525 M boronic acid and 0.2632 M naphthalene. The vial was then heated using an aluminum block heater set to 25° C. After thermal equilibration, the reaction was initiated via the addition of 50 µL of the appropriate precatalyst solution in THF (0.1 M [Pd]). Aliquots (~50-100 µL) were removed at reaction times indicated. The aliquots were purified by filtration through pipet filters containing approximately 1 cm of silica and eluted with 1-1.2 mL of ethyl acetate directly into GC vials. Conversion was determined by comparison of the GC responses of product and the internal naphthalene standard.

Example 18: Representative Procedures for Suzuki-Miyaura Reactions Using Dimeric Precatalysts of the Invention In a 1 dram vial equipped with a flea stir bar, 0.05 M [Pd]$_{tot}$ THF solution (KO$^t$Bu experiments) or 0.1 M [Pd]$_{tot}$ THF solution (K$_2$CO$_3$ experiments) were prepared by mixing the appropriate Pd(II) precursor with two equivalents of IPr under an atmosphere of dinitrogen. The solution was stirred for one hour at room temperature to allow for the generation of the appropriate ligated Pd(II) precatalyst. These solutions were used in catalytic experiments without any further treatment as described elsewhere herein.

Example 19: Suzuki-Miyaura Reactions Using Aryl Sulfamates

To a one dram vial equipped with a flea stir bar, N,N-dimethyl(1-naphthyl) sulfamate (32.7 mg, 0.13 mmol, 1 eq), 4-methoxyphenyl boronic acid (50.3 mg, 0.33 mmol, 2.5 eq), potassium carbonate (88 mg, 0.6 mmol, 4 eq), and palladium precatalyst (0.00325 mmol, 2.5 mol %) were added under an atmosphere of nitrogen. Toluene (1 mL) was added to start the reactions; each vial was stirred for 4 hours at 25° C. at which time it was opened to air. Conversion to product was determined using GC analysis.

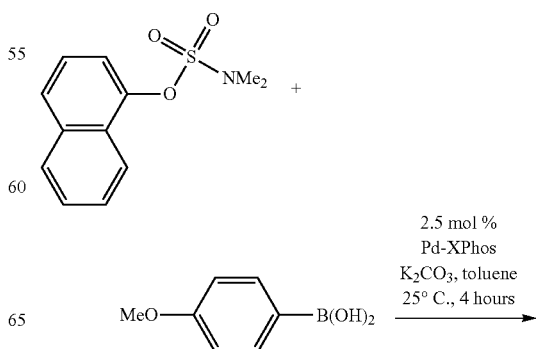

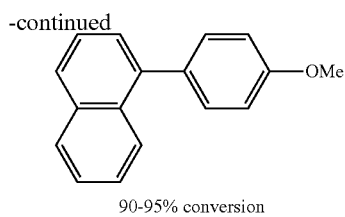

90-95% conversion

Example 20: Hiyama-Denmark Reactions Using Aryl Chlorides

In a nitrogen filled glove box, dimethyl-(4-methoxyphenyl)silanol (54 µL, 0.3 mmol, 1.5 eq) and sodium hydride (8.5 mg, 0.36 mmol, 1.8 eq) were added to a one dram vial along with toluene (1 mL). This mixture was allowed to age for 30 minutes. At this time, 4-(trifluoromethyl)-chlorobenzene (27 µL, 0.2 mmol, 1 eq) and palladium precatalyst (0.002 mmol, 1 mol %) were added in an additional 0.5 mL of toluene to start the reaction. Each vial was stirred for 18 hours at 70° C. Conversion to product was determined by GC analysis.

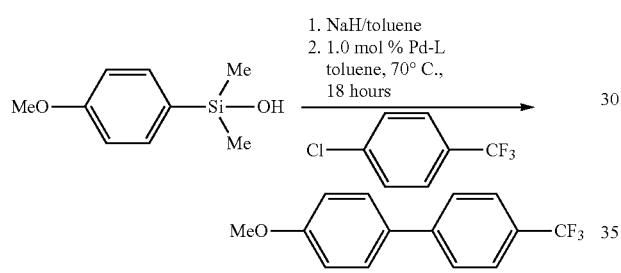

Example 21: Hiyama-Denmark Reactions Using Aryl Sulfamates

In a nitrogen filled glove box, dimethyl-(4-methoxyphenyl)silanol (54 µL, 0.3 mmol, 1.5 eq) and sodium hydride (8.5 mg, 0.36 mmol, 1.8 eq) were added to a one dram vial along with toluene (1 mL). This mixture was allowed to age for 30 minutes. At this time, N,N-dimethyl(4-[trifluoromethyl]phenyl)sulfamate (0.13 mmol, 1 eq) and palladium precatalyst (0.002 mmol, 1 mol %) were added in an additional 0.5 mL of toluene to start the reaction. Each vial was stirred for 18 hours at 70° C. Conversion to product was determined by GC analysis.

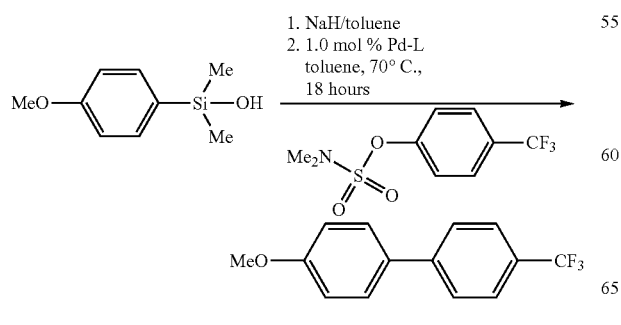

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of promoting a reaction between a first reagent and a second reagent, wherein one of the following applies:
   (a) the first reagent is an alkyl or cycloalkyl trifluoroboronate salt and the second reagent is an aromatic or heteroaromatic chloride; or
   (b) the first reagent is an aromatic or heteroaromatic boronic acid or ester and the second reagent is an aromatic or heteroaromatic halide, tosylate, triflate, mesylate, sulfamate or carbamate;
   the method comprising contacting the first reagent and the second reagent in the presence of at least one of (i) and (ii);
   (i) a ligand (L) and a precatalyst of formula (I), or a salt or solvate thereof:

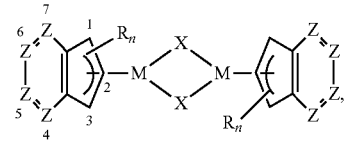
(I)

and
   (ii) a precatalyst of formula (II), or a salt or solvate thereof:

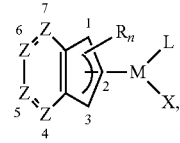
(II)

wherein:
   each occurrence of M is independently selected from the group consisting of Pd, Pt, and Ni;
   each occurrence of X is independently a ligand selected from the group consisting of halide, trifluoromethanesulfonate (triflate), tosylate, mesylate, tetrafluoroborate, tetraphenylborate, hexafluorophosphine, acetate, trifluoroacetate, acetonitrile, tetrahydrofuran, dichloromethane and water;
   each occurrence of R is independently selected from the group consisting of alkyl and substituted alkyl;
   with the proviso that each of the 5-membered rings is substituted with at least one independently selected R; and Z is CH or CR;

L is selected from the group consisting of a monodentate phosphine ligand, a bidentate phosphine ligand, and an N-heterocyclic carbene ligand; and n is 1, 2, or 3.

2. The method of claim 1, wherein each 5-membered ring is substituted with at least one R selected from the group consisting of methyl, isopropyl and tert-butyl.

3. The method of claim 1, wherein the 1- or 3-position of each 5-membered ring is substituted with R.

4. The method of claim 1, wherein L is selected from the group consisting of 1,3-bis(2,6-diisopropyl phenyl)-1,3-dihydro-2H-imidazol-2-ylidene and 1,3-bis(2,6-bis-(diphenylmethyl)-4-methoxyphenyl)imidazol-2-ylidene.

5. The method of claim 1, wherein L is a monodentate phosphine ligand, wherein the monodentate phosphine ligand is optionally selected from the group consisting of AmPhos (di-t-butylphosphino-4-dimethylaminobenzene), DavePhos (2-dicyclohexylphosphino-2'-(N,N-dimethylamino)biphenyl), $^{tBu}$DavePhos (2-Di-tert-butylphosphino-2'-(N,N-dimethylamino)biphenyl), QPhos (1,2,3,4,5-pentaphenyl-1'-(di-tert-butylphosphino)ferrocene), RuPhos (2-dicyclohexylphosphino-2',6'-diisopropoxybiphenyl), SPhos (2-dicyclohexylphosphino-2',6'-dimethoxybiphenyl), XPhos (2-dicyclohexylphosphino-2',4',6'-triisopropylbiphenyl), "BuXPhos (2-Di-tert-butylphosphino-2',4',6'-triisopropylbiphenyl), $^{Me4Bu}$XPhos (2-Di-tert-butylphosphino-3,4,5,6-tetramethyl-2',4',6'-triisopropyl-1,1'-biphenyl), BrettPhos (2-(Dicyclohexylphosphino)3,6-dimethoxy-2',4',6'-triisopropyl-1,1'-biphenyl), $^{tBu}$BrettPhos (2-(Di-tert-butylphosphino)-2',4',6'-triisopropyl-3,6-dimethoxy-1,1'-biphenyl), $^{Ad}$BrettPhos (2-(Diadamantylphosphino)-2',4',6'-triisopropyl-3,6-dimethoxy-1,1'-biphenyl), Me-DalPhos (2-(Di-1-adamantylphosphino) phenylpiperidine), Mor-DalPhos (Di(1-adamantyl)-2-morpholinophenylphosphine), Di(1-adamantyl)-1-piperidinyl-phenylphosphine, triphenylphosphine, tri(o-tolyl) phosphine, tricyclohexylphosphine and tri(t-butyl)phosphine.

6. The method of claim 1, wherein L is a bidentate phosphine ligand.

7. The method of claim 6, wherein L is selected from the group consisting of 1,1'-bis(diphenylphosphino)ferrocene (DPPF), 4,5-bis(diphenylphosphino)-9,9-dimethylxanthene (XantPhos), 4,6-bis (diphenylphosphanyl)-10H-phenoxazine (NiXantPhos), 1,2-bis(diphenylphosphino)ethane (dppe), 1,1-bis(diphenylphosphino)methane (dppm), 1,3-bis(diphenylphosphino)propane (dppp), 1,4-bis(diphenylphosphino)butane (dppb), 2,2'-bis(diphenylphosphino)-1,1'-binaphthyl (BINAP), bis[(2-diphenylphosphino) phenyl] ether (DPEPhos), 1,2-bis(dichlorophosphino) ethane, and 1,2-bis (dicyclohexylphosphino)-ethane (dcpe).

* * * * *